(12) United States Patent
Sharma et al.

(10) Patent No.: US 11,253,389 B2
(45) Date of Patent: Feb. 22, 2022

(54) FEMALE FLUID REMOVAL DEVICE

(71) Applicant: CM Technologies, Inc., San Diego, CA (US)

(72) Inventors: Amit Kumar Sharma, New Delhi (IN); Nishith Chasmawala, Gujarat (IN); John Everett Martin, Gainesville, FL (US); Shreyas Dighe, Maharashtra (IN); Geetika Garg, Uttar Pradesh (IN)

(73) Assignee: CM Technologies, Inc., San Diego, CA (US)

( * ) Notice: Subject to any disclaimer, the term of this patent is extended or adjusted under 35 U.S.C. 154(b) by 0 days.

(21) Appl. No.: 17/320,061

(22) Filed: May 13, 2021

(65) Prior Publication Data

US 2021/0353450 A1    Nov. 18, 2021

Related U.S. Application Data

(63) Continuation of application No. 17/235,853, filed on Apr. 20, 2021.

(30) Foreign Application Priority Data

May 14, 2020    (IN) .............................. 202011020467

(51) Int. Cl.
  *A61F 5/445*    (2006.01)
  *A61F 5/44*    (2006.01)
  *A61F 5/455*    (2006.01)
(52) U.S. Cl.
  CPC ............ *A61F 5/455* (2013.01); *A61F 5/4401* (2013.01); *A61F 5/4408* (2013.01)

(58) Field of Classification Search
  CPC combination set(s) only.
  See application file for complete search history.

(56) References Cited

U.S. PATENT DOCUMENTS

| 3,349,768 A | 10/1967 | Xavier |
| 3,511,241 A * | 5/1970 | John ...................... A61F 5/453 604/352 |
| 3,512,185 A | 5/1970 | Ells |

(Continued)

FOREIGN PATENT DOCUMENTS

| EP | 0032138 B1 | 11/1984 |
| GB | 1571657 A | 7/1980 |

(Continued)

OTHER PUBLICATIONS

Sharma et al.; U.S. Appl. No. 17/235,853 entitled "Fluid removal device," filed Apr. 20, 2021.

*Primary Examiner* — Guy K Townsend
(74) *Attorney, Agent, or Firm* — Shay Glenn LLP

(57) ABSTRACT

A urine removal device includes a plurality of layers suitable to capture and transfer urine. A conduit system is disposed inside of the device and extends from the proximal portion of the device, where it interfaces via an outlet conduit member, to the distal end of the device where it draws in urine from the device. The device allows air flow through the device to support suction that is applied. The fluid layer system has at least one conduit configured to draw urine from the distal portion of the device up to the proximal end of the device, and into the outlet conduit where it exits the urine removal device.

22 Claims, 37 Drawing Sheets

(56) References Cited

U.S. PATENT DOCUMENTS

| | | | |
|---|---|---|---|
| 3,881,486 A * | 5/1975 | Fenton | A61F 5/4405 604/335 |
| 4,020,843 A * | 5/1977 | Kanall | A61F 5/453 604/351 |
| 4,022,213 A * | 5/1977 | Stein | A61F 5/453 604/350 |
| 4,084,589 A * | 4/1978 | Kulvi | A61B 10/007 604/73 |
| 4,178,934 A * | 12/1979 | Forman | A61F 5/44 24/54 |
| 4,246,901 A | 1/1981 | Frosch et al. | |
| 4,257,418 A | 3/1981 | Hessner | |
| 4,281,655 A * | 8/1981 | Terauchi | A61F 5/451 4/305 |
| 4,387,726 A | 6/1983 | Denard | |
| 4,457,314 A | 7/1984 | Knowles | |
| 4,466,888 A * | 8/1984 | Verkaart | A61M 1/0001 210/232 |
| 4,622,981 A * | 11/1986 | Sherlock | A61B 5/208 600/575 |
| 4,625,734 A * | 12/1986 | Sherlock | A61B 5/208 600/575 |
| 4,692,160 A | 9/1987 | Nussbaumer | |
| 4,747,166 A | 5/1988 | Kuntz | |
| 4,795,449 A | 1/1989 | Schneider et al. | |
| 4,799,928 A | 1/1989 | Crowley | |
| 4,804,377 A * | 2/1989 | Hanifl | A61F 5/44 4/144.2 |
| 4,886,508 A | 12/1989 | Washington | |
| 4,889,533 A | 12/1989 | Beecher | |
| 4,941,878 A * | 7/1990 | Petrik | A61F 5/442 604/105 |
| 5,141,504 A * | 8/1992 | Herweck | A61M 1/61 604/317 |
| 5,300,052 A * | 4/1994 | Kubo | A61F 5/453 4/144.1 |
| 5,401,262 A * | 3/1995 | Karwoski | A61M 1/0001 604/321 |
| 5,735,837 A * | 4/1998 | Ishikawa | A61F 5/453 604/385.09 |
| 5,827,257 A * | 10/1998 | Fujioka | A61F 13/471 604/385.19 |
| 6,129,715 A * | 10/2000 | Cunningham | A61F 5/445 128/885 |
| 6,311,339 B1 | 11/2001 | Kraus | |
| 6,464,674 B1 * | 10/2002 | Palumbo | A61F 5/443 604/317 |
| 6,530,909 B1 * | 3/2003 | Nozaki | A61F 13/471 604/349 |
| 6,569,133 B2 | 5/2003 | Cheng et al. | |
| 6,585,720 B2 | 7/2003 | Lapcevic | |
| 6,635,038 B2 * | 10/2003 | Scovel | A61F 5/453 604/347 |
| 6,732,384 B2 | 5/2004 | Scott | |
| 6,857,137 B2 | 2/2005 | Otto | |
| 7,186,245 B1 * | 3/2007 | Cheng | A61F 5/44 604/349 |
| 7,390,320 B2 | 6/2008 | Machida et al. | |
| 7,755,497 B2 | 7/2010 | Wada et al. | |
| 7,927,320 B2 | 4/2011 | Goldwasser et al. | |
| 8,075,538 B2 * | 12/2011 | Vernon | A61F 5/4404 604/322 |
| 8,196,230 B2 * | 6/2012 | Nakamura | A61G 7/02 4/321 |
| 8,287,508 B1 | 10/2012 | Sanchez | |
| 8,303,554 B2 | 11/2012 | Tsai et al. | |
| 8,357,105 B2 * | 1/2013 | Fontaine | A61F 5/4404 600/580 |
| 9,173,799 B2 * | 11/2015 | Tanimoto | A61F 5/451 |
| 9,445,934 B2 * | 9/2016 | Ugarte | A61F 5/453 |
| 9,788,992 B2 * | 10/2017 | Harvie | A61M 25/0017 |
| 10,064,774 B2 * | 9/2018 | Onoda | A61F 5/451 |
| 10,226,376 B2 | 3/2019 | Sanchez et al. | |
| 10,376,406 B2 | 8/2019 | Newton | |
| 10,376,407 B2 | 8/2019 | Newton | |
| 10,390,989 B2 | 8/2019 | Sanchez et al. | |
| 10,426,654 B2 * | 10/2019 | Ugarte | A61F 5/453 |
| 10,857,025 B2 | 12/2020 | Davis et al. | |
| 10,952,889 B2 | 3/2021 | Newton et al. | |
| 10,973,678 B2 * | 4/2021 | Newton | A61M 1/0023 |
| 11,026,829 B2 * | 6/2021 | Harvie | A61F 5/455 |
| 2002/0087131 A1 | 7/2002 | Wolff et al. | |
| 2003/0163120 A1 | 8/2003 | Harvie | |
| 2004/0006321 A1 * | 1/2004 | Cheng | A61F 5/44 604/349 |
| 2006/0111681 A1 * | 5/2006 | Vernon | A61M 1/69 604/326 |
| 2006/0218709 A1 | 10/2006 | Langford | |
| 2006/0253091 A1 * | 11/2006 | Vernon | A61F 5/4405 604/353 |
| 2008/0004560 A1 * | 1/2008 | Miskie | A61F 5/4408 602/75 |
| 2008/0091153 A1 * | 4/2008 | Harvie | A61F 5/451 604/318 |
| 2008/0281284 A1 * | 11/2008 | Garfield | A61F 5/4404 604/327 |
| 2009/0193571 A1 * | 8/2009 | Nakamura | A61G 7/02 4/300 |
| 2009/0270910 A1 * | 10/2009 | Hargens | A61H 9/005 606/201 |
| 2010/0160881 A1 * | 6/2010 | Lin | A61M 1/962 604/327 |
| 2010/0298789 A1 * | 11/2010 | Santimaw | A61F 5/451 604/319 |
| 2011/0060300 A1 * | 3/2011 | Weig | A61M 1/743 604/319 |
| 2011/0092892 A1 | 4/2011 | Nitsan et al. | |
| 2012/0029485 A1 | 2/2012 | Tan | |
| 2012/0103347 A1 | 5/2012 | Wheaton et al. | |
| 2012/0116336 A1 * | 5/2012 | Sharma | A61M 1/84 604/328 |
| 2014/0157499 A1 * | 6/2014 | Suzuki | A47K 11/00 4/144.3 |
| 2014/0182051 A1 * | 7/2014 | Tanimoto | A61G 9/006 4/144.3 |
| 2014/0276494 A1 * | 9/2014 | Cisko | A61M 1/602 604/319 |
| 2015/0135423 A1 * | 5/2015 | Sharpe | A61F 5/453 4/471 |
| 2016/0051395 A1 * | 2/2016 | Ugarte M.D. | A61F 5/4408 604/544 |
| 2016/0367226 A1 | 12/2016 | Newton et al. | |
| 2017/0000642 A1 * | 1/2017 | Cisko | A61F 5/44 |
| 2017/0007438 A1 * | 1/2017 | Harvie | A61M 25/0017 |
| 2017/0042724 A1 * | 2/2017 | Ugarte | A61F 5/4556 |
| 2017/0252202 A9 | 9/2017 | Sanchez et al. | |
| 2017/0312405 A1 | 11/2017 | Newton | |
| 2019/0038451 A1 * | 2/2019 | Harvie | A61F 5/453 |
| 2019/0247222 A1 * | 8/2019 | Ecklund | A61F 5/443 |
| 2019/0247566 A1 | 8/2019 | Hassidov et al. | |
| 2019/0358075 A1 * | 11/2019 | Scharich, III | A61G 7/0503 |
| 2019/0365561 A1 | 12/2019 | Newton et al. | |
| 2020/0046544 A1 * | 2/2020 | Godinez | A61F 5/455 |
| 2020/0085610 A1 | 3/2020 | Cohn et al. | |
| 2020/0315838 A1 | 10/2020 | Eckert | |
| 2020/0390591 A1 | 12/2020 | Glithero et al. | |
| 2021/0113130 A1 * | 4/2021 | Tran | A61F 5/453 |

FOREIGN PATENT DOCUMENTS

| | | |
|---|---|---|
| GB | 2260907 B | 5/1995 |
| JP | H08117329 A | 5/1996 |
| WO | WO93/09736 A2 | 5/1993 |
| WO | WO2004/026194 A1 | 4/2004 |
| WO | WO2007/005851 A2 | 1/2007 |
| WO | WO2016/103242 A1 | 6/2016 |
| WO | WO2019/212949 A1 | 11/2019 |
| WO | WO2019/212950 A1 | 11/2019 |

(56) References Cited

FOREIGN PATENT DOCUMENTS

| WO | WO2019/212951 A1 | 11/2019 |
| WO | WO2019/212955 A1 | 11/2019 |
| WO | WO2019/212956 A1 | 11/2019 |

\* cited by examiner

FIBERS
ALIGNED AT 0°

FIBERS
ALIGNED AT 90°

SECTION C-C

SECTION D-D

FEMALE FLUID REMOVAL DEVICE

CROSS REFERENCE TO RELATED APPLICATIONS

This application claims the benefit of Indian Provisional Patent Application Ser. No. 202011020467, filed May 14, 2020 (DAS Access Code: 9E9E), and to International Patent Application No. PCT/US2021/031926 filed on May 12, 2021 and titled "URINE COLLECTION DEVICE." This application also claims priority as a continuation of U.S. patent application Ser. No. 17/235,853 filed on Apr. 20, 2021, and titled "FLUID REMOVAL DEVICE." Each of these applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Urine management systems are some of the most commonly used products in a variety of healthcare settings. Though typically associated with urinary incontinence in bedridden patients, the need extends further. For example, patients may require accurate monitoring of urine output for clinicians to evaluate their fluid-levels or assess vital functions of the body. Urine management systems may be used to reduce the burden of frequent urination in those who are semi-ambulatory, or may be used to reduce the risk of wound development by keeping the perineal and sacral skin dry. As the range of clinical needs is broad, all care settings, from ICU to home, may incorporate an assortment of urine management products.

One of the most common devices used for urine management in such patients is the indwelling urinary catheter, which may be designed for intermittent or extended use. These devices are low profile latex or silicon tubes inserted through the urethra, all the way into the bladder, where they are anchored using a balloon, to continually drain urine into a collection bag or container. Since the invention of the Foley catheter nearly a century ago, the extended use of indwelling catheters has continuously risen, until recently.

Placement of any product into the human body involves risks, especially when the target anatomy is sensitive or sterile. In the case of urinary catheters, the risk of patient harm during insertion and use is significant enough to require trained care providers such as nurses or physicians to perform the insertion, removal, and management of the devices. Even when caution is taken, indwelling catheters can cause significant impairment to urethral tissues during placement. Furthermore, maintaining catheter sterility is difficult. Patients often experience pain and bleeding during insertion and are faced with the possibility of bacteria being introduced into the bladder and renal system. Ultimately, there is a risk of patients developing injuries or urinary tract infections leading to subsequently bladder, kidney, or blood-stream infections.

To reduce these risks and improve clinical outcomes, care providers are transitioning away from indwelling catheters and increasingly using external management systems. These external management systems typically include a collection member to receive urine and an anchoring mechanism, sometimes in the form of an adhesive or strap to secure the collection member in-place. Some of these systems are designed using soft and flexible materials for the collection member and include a drainage tube to remove accumulated fluid.

Using soft and flexible materials for the collection member, as well as other components of such a system, such as a drainage tube that may be used in a genital or perineal region, is important for multiple reasons. One reason is that skin and tissues in the genital and perineal regions are more sensitive than other areas of the body, meaning they are often at increased risk of injury. In clinical settings, it is not uncommon for patients to experience skin maceration, dermatitis, and pressure injuries. These complications may be due to tissue swelling exacerbating skin weakness, from improper movement along with extended exposure to moisture, or the use of devices/products in the area that become lodged between the skin and another surface. Furthermore, soft and flexible materials allow patients to move with less discomfort, and more flexible parts allow movement of a part of the product without the adhesive (used to secure the collection member) becoming pulled on or stressed.

Drainage tubes used for these types of devices often have shortcomings such as kinking, which will either significantly decrease or completely block the flow of fluids through the lumen. The interface between the drainage tube and the collection member can be another key point of weakness, for example, movement of the drainage tube can cause kinking, bending, or twisting of the flexible tube at the connection point, resulting in reduced or blocked fluid flow.

Recently developed suction based collection/protection devices that are external to the body rely on an absorbent material, which is a relic of diapers and pads. The use of the absorbent materials may lead to wetness on the skin, bulkiness, and dislodgement or peeling-off of the device. Retaining absorbed urine may also lead to inefficient suction, reduced air flow and other clinical complications. Furthermore, these devices do not perform effectively when the patient is in a lateral position.

Thus, there is a need for a low-cost urine removal device that enables urine to be conveniently and hygienically removed from the region surrounding a female patient's genitalia while simultaneously resisting kinking and folding, and that provides a relatively dry contact region with little or no pooled or residual urine in all patient configurations.

SUMMARY OF THE DISCLOSURE

In general, described herein are apparatuses (e.g., devices, system, etc.) and method for removal of urine from a subject (e.g. a patient). In particular, these apparatuses and methods may be used to remove urine from a female subject.

The apparatuses described herein may include a frame that includes a base region (also referred to herein as a "base") from which a fluid collection region extends distally. The frame may also include at least one branch extending from the base region along a proximal to distal length of the device. The at least one branch (also referred to herein as an "arm" or "extension") may be integrally formed with the base region or it may be separately formed, and attached to the base region. The at least one branch generally extends distally from the base region and may be curved to conform to the body of the user. In some examples the one or more branches are biased by a spring force so that it assumes the curved shape (e.g., "C-shape") as it extends from the base region. The at least one branch may support the fluid collection region and/or may underlie, overlie or be at least partially enclosed within the fluid collection region.

The fluid collection region may be a layered structure that is configured to fit against the subject's vulval region. The layers of the fluid collection region may include an inner layer that is permeable to fluid (e.g., urine), an outer layer that is substantially impermeable to urine, and a transfer layer that is disposed between the inner layer and the outer layer. The patient-facing side of the fluid collection region may be held in the inner (concave) portion of the C-shape formed by the one or more branches in some examples. The inner layer (which may also be referred to as the patient-contacting layer or collection layer) may be exposed on one side of the fluid collection region. The fluid collection region may include one or more suction conduits extending from the base region distally, e.g., towards the bottom of the fluid collection region. The one or more (in some examples two) suction conduits may be configured to support the fluid collection region. For example, the one or more suction conduits may be configured to form a separation (e.g., an air gap) between two or more of the layers, such as the outer layer and the transfer layer, and/or the transfer layer and the inner layer. The suction conduits may also be referred to herein as suction tubes, suction channels, or simply tubes.

Any of the fluid collection regions described herein may also include an overhang layer that at least partially overlaps the periphery of the inner layer. The overhang layer may form an annuls around the periphery of the inner layer. In some examples the overhang layer is formed of the outer layer (e.g., doubled/folded back over the inner layer) or may be formed of the same material as the outer layer, and is typically not fluid permeable (e.g. urine permeable). The overhang layer may prevent urine from spilling out of the fluid collection region.

In some examples the one or more suction conduits may provide support in the distal-to-proximal direction, and may be biased to bend or curve to help conform the fluid collection region to the patient anatomy. In variations including the one or more branches, the one or more fluid collection conduits may be configured to bend or flex along their length with the one or more branches. The one or more suction conduits may be coupled to the one or more branches. For example, the one or more suction conduits (e.g., suction tubes) can be integrated into the frame. Alternatively, in some examples, the apparatus may include a relatively stiff and/or curved (or biased to curve) suction conduit instead of one or more branches. In general, the suction conduits may be resistant to kinking or bending, including by integrating or coupling to the frame as described herein.

Any of these apparatuses may include a suction source tube that extends (e.g., extends proud of) the base region, to which a suction (vacuum) source may be fluidly coupled, to provide negative pressure to the apparatus. The suction source tube may be fluidly continuous with the one or more suction conduits. For example, a first suction conduit extends from the base region (e.g., from a suction source tube in the base) along a right side of the fluid collection region between the inner layer and the outer layer, and a second suction conduit may extend along a left side of the fluid collection region between the inner layer and the outer layer. The suction source tube may be configured to prevent kinking, twisting, folding or collapse of the suction source tube, and/or may be pivotally isolated from the suction conduits. For example, any of the suction source tubes may include a flex joint configured to prevent the suction source tube from being kinked, twisted, folded or collapsed, and may help maintain patency of the lumen of the suction source tube between the fluid inlets and the outlet. In general the one or more suction conduits may include one or more fluid inlets, including at their distal ends. For example, a first suction conduit may end in a first fluid inlet at the distal end region of the fluid collection region and a second suction conduit may end in a second fluid inlet at the distal end region of the left side of the fluid collection region.

The base region may generally include an adhesive layer (in some cases with a protective, removably backing) to secure the apparatus to the patient (e.g., above the pubic region) so that the fluid collection region is positioned over and/or against the vulval region of the patient. In some cases the fluid collection region (including the overhang layer) may not include any adhesive; alternatively in some examples the fluid collection region may also include an adhesive material (e.g., on or adjacent to the overhang layer).

In general, the fluid collection regions include a non-absorbing, porous, fluid permeable and hydrophobic inner layer (e.g., the patient-facing layer). The outer layer may be a breathable yet substantially impermeable to liquid, non-absorbing, hydrophobic layer. The fluid collection region may also typically include a flow directing middle layer, and in any of these examples a non-absorbing overhang layer, as described herein.

These apparatuses and methods may operate to remove urine (and prevent spillage of urine onto bedding and/or patient close) regardless of the position the patient is lying in (e.g., supine, on the left side, on the right side, etc.). Thus, these apparatuses may work in a lateral (flat) position, and a vertical (on the side) position. In some cases the inlets (e.g., coupled to the one or more suction conduits) may be positioned on the right and left side, and the apparatus may be prevented from folding or obstructing the inlet and one or more suction conduits. In some examples the apparatus may include one or more valves to direct the majority of the negative pressure to one or the other (e.g., left or right) side of the fluid collection region based on the orientation that the fluid collection region is being held, further enhancing the ability of the apparatus to operate both when the patient is in supine position as well as in lateral position.

As mentioned, the fluid collection region may be configured to contour to the patient's body, and may be biased to comfortably maintain the contact and configuration. For example, any of these apparatuses may be configured to include a biasing (e.g. spring) force because of the frame and/or suction conduits may hold the curved configuration of the fluid collection region. In some examples the frame (e.g., the one or more branches) may be configured as a spring, e.g., leaf spring, to contour the fluid collection region to the patient by applying a torsional force from the base region of the device helps keep the device in constant contact with the anatomy. The spring force applied by the frame (e.g., the one or more branches as well as the base) can be modulated or auto-adjusted based on patient size and anatomy.

As mentioned, in some examples the apparatus may include one or more gravity (and therefore position) activated self-regulated flow valves. The flow valves may include check valves that direct the flow to one side (e.g., left side, right side, etc.) of the apparatus based on the orientation/position. For example, the one or more valves may be flow regulation valves that are activated (open) when the position of the apparatus (as worn by the patient) in gravity indicates that the patient is on one side or the other. If the patient is on the left side, the left side valve may be open while the right side valve is closed, allowing most of the negative pressure to more forcefully and/or quickly withdraw fluid from the left side; if the patient is on their right side, the right side valve may be open while the left side valve is closed, allowing most of the negative pressure to be more forcefully and/or quickly withdraw fluid from the right side. If the patient is lying substantially supine, both left and right valves may be open. Thus, these valves may operate based on a combination of gravity and position, as described herein. These valves may be configured to limit the vacuum from one of the suction channels to improve suction efficiency from the other suction channel.

In general, the fluid collection region may be air permeable, e.g., all of the layers of the fluid collection region may be air permeable, including the fluid impermeable outer layer. This may significantly help in keeping the anatomy and device dry.

For example, described herein are apparatuses (e.g., devices, systems, etc.) for removing urine discharged from a body of a user. A device may include: a frame comprising a base region and at least one branch extending from the base region along a proximal to distal length of the device, wherein the at least one branch is curved to conform to the body of the user; a fluid collection region extending distally from the base region, the fluid collection region comprising: an inner layer that is permeable to urine, an outer layer that is substantially impermeable to urine, and a transfer layer disposed between the inner layer and the outer layer; a first suction conduit extending along a right side of the fluid collection region between the inner layer and the outer layer and ending in a first fluid inlet at a distal end region of the right side of the fluid collection region; and a second suction conduit extending along a left side of the fluid collection region between the inner layer and the outer layer and ending in a second fluid inlet at the distal end region of the left side of the fluid collection region.

For example, a device for removing urine discharged from a body of a user may include: a base region comprising an adhesive patch to secure to the device to the user; a fluid collection region extending proximally to distally from the base region, the fluid collection region comprising: an inner layer that is permeable to urine, an outer layer that is substantially impermeable to urine, and a transfer layer disposed between the inner layer and the outer layer; a first suction conduit extending from the base region and extending along a right side of the fluid collection region between the inner layer and the outer layer and ending in a first fluid inlet at a distal end region of the right side of the fluid collection region; a second suction conduit extending from the proximal end region of the device and extending along a left side of the fluid collection region between the inner layer and the outer layer and ending in a second fluid inlet at the distal end region of the left side of the fluid collection region; and at least one branch extending distally from the base region along a proximal to distal length of the device and curved to conform to the body of the user.

The at least one branch may have a variable thickness and/or stiffness along its length. In some examples, the at least one branch has a stepped thickness along its length. For example, each branch of the at least one branch may taper laterally along the length. In any of these apparatuses, the at least one branch of the frame may be biased with a spring force to curve in a C-shape to conform to the body of the user. For example, the at least one branch of the frame may be configured as a leaf spring comprising a plurality of curved layers that are coupled together.

In any of these apparatuses, the inner layer and the outer layer may be attached at an outer periphery of the fluid collection region. Any of these apparatuses may include an overhang layer extending over a periphery of the inner layer, wherein the overhang layer is at least partially unattached where it overlaps the inner layer.

The transfer layer may comprise a plurality of flow directors oriented substantially longitudinally along the fluid collection region. In some examples, the transfer layer is formed of a polymeric material having a thickness 0.5 mm or less. The fluid collection region mat taper distally such that a width of the distal end is narrower than a width of the proximal end.

In some examples, the frame is positionable, and may be bent to a desired shape, which it may hold. For example, the frame may comprise a malleable material capable of being conformably fit to the user's anatomy.

Any of these apparatuses may include a finger strap. For example, a finger strap may be attached near the distal end of the device configured to encircle one or more of the fingers of a hand installing the device.

In any of these apparatuses, the apparatus may include an adhesive patch attached to the base region for attaching to the device to a patient.

In some examples the apparatus includes a suction source tube in fluid communication with the first and second conduits. Alternatively, the first and second conduits may be separately attached to a source of negative pressure (e.g., vacuum), either directly or indirectly.

Any of these apparatuses may include an air gap between the outer layer and the transfer layer.

In general, the inner layer may comprise a non-absorbing, porous, urine-permeable, hydrophobic layer. The outer layer may be breathable, substantially impermeable to urine, non-absorbing, and hydrophobic. The inner layer, outer layer and transfer layer may generally be air permeable.

For example, a device for removing urine discharged from a body of a user may include: a frame comprising a base region and at least one branch extending from the base region along a proximal to distal length of the device, wherein the at least one branch is curved to conform to the body of the user; a fluid collection region extending distally from the base region and supported by the at least one branch, the fluid collection region comprising: an inner layer that is permeable to urine, an outer layer that is substantially impermeable to urine, and a transfer layer disposed between the inner layer and the outer layer; a first suction conduit extending from a suction source tube on the base region and extending along a right side of the fluid collection region between the inner layer and the outer layer and ending in a first fluid inlet at a distal end region of the right side of the fluid collection region; and a second suction conduit extending from the suction source tube and extending along a left side of the fluid collection region between the inner layer and the outer layer and ending in a second fluid inlet at the distal end region of the left side of the fluid collection region.

As mentioned, any of the urine collection apparatuses described herein may include an overhang layer that may help protect against spilling or soiling of the patient, clothing and/or bedding. For example, a device for removing urine discharged from a body of a user may include: a fluid collection region comprising: an inner layer that is permeable to urine, an outer layer that is substantially impermeable to urine, a transfer layer disposed between the inner layer and the outer layer, and an overhang layer that at least partially overlaps the periphery of the inner layer; a first suction conduit extending from a proximal end region (e.g., the base region) of the device and along a right side of the fluid collection region between the inner layer and the outer layer and ending in a first fluid inlet at a distal end region of the right side of the fluid collection region, and a second suction conduit extending from the proximal end region of the device (e.g., the base region) and extending along a left side of the fluid collection region between the inner layer and the outer layer and ending in a second fluid inlet at a distal end region of the left side of the fluid collection region.

The overhang layer may form an annulus over the inner layer on an outside of the fluid collection region. The overhang layer may be at least partially unattached where it overlaps the inner layer. The overhang layer may be formed of a material that does not absorb urine.

Any of these apparatuses may include a frame having a base and at least one branch extending from the base along a substantial length of the device wherein the at least one branch is curved to conform to the body of the user.

As mentioned, any of these apparatuses may include an adhesive patch attached to the base for attaching to the device to a patient.

The least one branch may have a variable thickness and/or stiffness along its length. The at least one branch may have a stepped thickness along its length. Each branch of the frame may taper laterally along the length. The first and second suction conduits may each comprise a gravity activated valve. The gravity activated valve may comprise a ball check valve and/or a flap valve.

The suction conduits may be curved to conform with a vaginal region.

Any of these apparatuses may include an adhesive patch, e.g., attached to at least one layer of the fluid collection region. Each suction conduit may form a sidewall of the fluid collection region with an air gap between the first suction conduit and the second suction conduit. The inner layer and the outer layer may be joined together around a periphery of the fluid collection region so that the first suction conduit and the second suction conduit are inside of the fluid collection region.

For example, a device for removing urine discharged from a body of a user may include: a frame comprising a base region and at least one branch extending from the base region along a proximal to distal length of the device, wherein the at least one branch is curved to conform to the body of the user; a fluid collection region extending distally from the base region and supported by the at least one branch, the fluid collection region comprising: an inner layer that is permeable to urine, an outer layer that is substantially impermeable to urine, a transfer layer disposed between the inner layer and the outer layer, and an overhang layer that is impermeable to urine, the overhang layer forming an annulus around the periphery of the inner layer, wherein the overhang layer is at least partially unattached where it overlaps the inner layer; a first suction conduit extending from a proximal end region of the device and along a right side of the fluid collection region between the inner layer and the outer layer and ending in a first fluid inlet at a distal end region of the right side of the fluid collection region, and a second suction conduit extending from the proximal end region of the device and extending along a left side of the fluid collection region between the inner layer and the outer layer and ending in a second fluid inlet at a distal end region of the left side of the fluid collection region.

As mentioned above, any of these apparatuses may include a valve (or multiple valves) that may detect the position of the apparatus and/or the orientation of the apparatus and direct negative pressure in order to drain urine preferentially from regions where it may otherwise pool and overflow from the device. For example, described herein are devices for removing urine discharged from a body of a user that include: a fluid collection region comprising: an inner layer that is permeable to urine, an outer layer that is substantially impermeable to urine, a transfer layer disposed between the inner layer and the outer layer, and an overhang layer that at least partially overlaps the periphery of the inner layer; a first suction conduit extending from a proximal end region of the device (e.g., a base region) and along a right side of the fluid collection region between the inner layer and the outer layer and ending in a first fluid inlet at a distal end region of the right side of the fluid collection region; a second suction conduit extending from the proximal end region of the device (e.g., a base region) and extending along a left side of the fluid collection region between the inner layer and the outer layer and ending in a second fluid inlet at a distal end region of the left side of the fluid collection region; and a first gravity activated valve in fluid communication with the first suction conduit and configured to close when the first fluid inlet is held laterally above the second fluid inlet; and a second gravity activated valve in fluid communication with the second suction conduit and configured to close when the second fluid inlet is held laterally above the first fluid inlet.

One and/or both of the first and second gravity activated valves may comprise a ball check valve. One and/or both of the first and second gravity activated valves may comprise a flap valve.

As mentioned above, the overhang layer may form an annulus over the inner layer on an outside of the fluid collection region. The overhang layer may be at least partially unattached where it overlaps the inner layer. The overhang layer may not absorb urine (e.g., may be fluid impermeable).

Any of these apparatuses (e.g., devices, systems, etc.) may include a frame having a base region and at least one branch extending from the base region along a substantial length of the device wherein the at least one branch is curved to conform to the body of the user. An adhesive patch may be attached to the base region for attaching to the device to a patient.

The at least one branch may have a variable thickness and/or stiffness along its length. The at least one branch may have a stepped thickness along its length. Each branch of the frame may taper laterally along the length. The suction conduits may be curved to conform with a vaginal region.

For example, a device for removing urine discharged from a body of a user may include: a frame comprising a base region and at least one branch extending from the base region along a proximal to distal length of the device, wherein the at least one branch is curved to conform to the body of the user; a fluid collection region extending distally from the base region and supported by the at least one branch, the fluid collection region comprising: an inner layer that is permeable to urine, an outer layer that is substantially impermeable to urine, a transfer layer disposed between the inner layer and the outer layer, and an overhang layer that is impermeable to urine, the overhang layer forming an annulus around the periphery of the inner layer, wherein the overhang layer is at least partially unattached where it overlaps the inner layer; a first suction conduit extending from a proximal end region of the device and along a right side of the fluid collection region between the inner layer and the outer layer and ending in a first fluid inlet at a distal end region of the right side of the fluid collection region; a second suction conduit extending from the proximal end region of the device and extending along a left side of the fluid collection region between the inner layer and the outer layer and ending in a second fluid inlet at a distal end region of the left side of the fluid collection region; a first gravity activated valve in fluid communication with the first suction conduit and configured to close when the first fluid inlet is held laterally above the second fluid inlet; and a second gravity activated valve in fluid communication with the second suction conduit and configured to close when the second fluid inlet is held laterally above the first fluid inlet.

Also described herein are urine removal apparatuses (e.g., devices, system, etc.) that include a layered fluid collection region. In some examples this fluid collection region may be supported by a frame, including some of the examples described above. For example, a device for removing urine discharged from a body of a user may include: a fluid collection region comprising: an inner layer that is permeable to urine, an outer layer that is substantially impermeable to urine, and a transfer layer disposed between the inner layer and the outer layer; at least one suction conduit extending from a proximal end region of the device and disposed between the inner layer and the outer layer and ending in one or more fluid inlets at a distal end region of the fluid collection region, and a frame comprising a base region and at least one branch extending from the base region along a length of the device and curved to conform to the body of the user.

The at least one suction conduit may include a first suction conduit extending from a suction source tube at the base to a first fluid inlet of the one or more fluid inlets, wherein the first fluid inlet is on a right side of the fluid collection region, further wherein the at least one suction conduit comprises a second suction conduit extending from the suction source tube to a second fluid inlet of the one or more fluid inlets, wherein the second fluid inlet is on a left side of the fluid collection region. In some examples, the apparatus includes a first gravity activated valve in fluid communication with the first suction conduit and configured to close when the first fluid inlet is held laterally above the second fluid inlet; and a second gravity activated valve in fluid communication with the second suction conduit and configured to close when the second fluid inlet is held laterally above the first fluid inlet.

Alternatively, in some examples the at least one suction conduit comprises a bifurcated joint at a distal end having a first gravity-activated valve and a second gravity-activated valve therein, wherein the first gravity-activated valve is configured to close when the device is tilted laterally in a first direction and wherein the second gravity-activated valve is configured to close when the device is tilted laterally in a second direction that is opposite to the first direction. In some examples the at least one of the first and second gravity-activated valves comprises a ball check valve. The at least one of the first and second gravity-activated valve may include a flap valve.

For example, a device for removing urine discharged from a body of a user may include: a base region comprising an adhesive patch to secure to the device to the user; a fluid collection region extending distally from the base region, the fluid collection region comprising: an inner layer that is permeable to urine, an outer layer that is substantially impermeable to urine, and a transfer layer disposed between the inner layer and the outer layer; at least one suction conduit extending from a proximal end region of the device and disposed between the inner layer and the outer layer and ending in one or more fluid inlets at a distal end region of the fluid collection region, and at least one branch extending distally from the base region along a length of the fluid collection region and biased to curve in a C-shape to conform to the body of the user.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which.

DETAILED DESCRIPTION

Figure 1A:
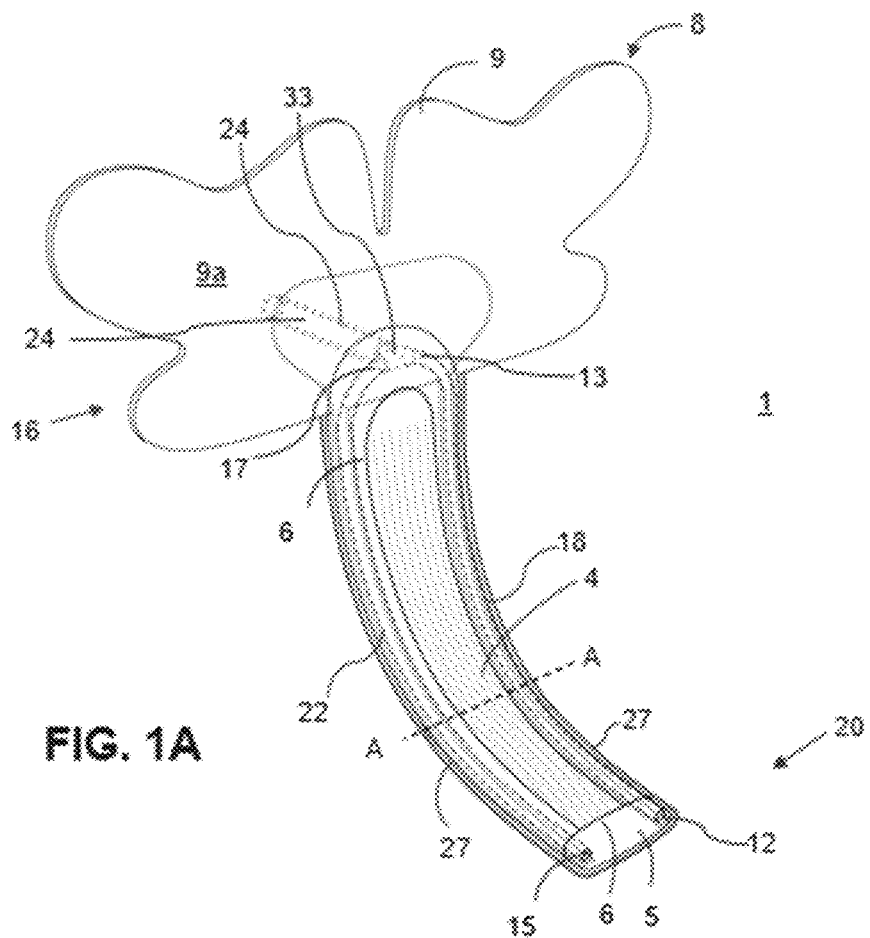
FIGS. 1A and 1B, illustrate a perspective view and an exploded view of an example embodiment of a urine removal device.

Described herein are urine removal devices that are suction-assisted and enable urine to be conveniently and hygienically removed from the region surrounding a female patient's genitalia area.

The term "proximal" and "distal" are used with reference to the length of the urine removal device; that is, "proximal" denotes the first end of the device toward the suprapubic region where it engages with (or is positioned in the vicinity of) the lower abdomen and "distal" denotes the opposed second end of the device toward the end where it resides between the legs of the patient positioned or located in the vicinity of perineum. For the purposes of this disclosure, the terms "inner" and "outer" are used with reference to upper and lower surfaces of the urine removal device or components thereof. That is, "inner" denotes a surface or direction that is coincident with or is in the direction adjacent to or toward the genitalia. In contrast, "outer" denotes a surface or direction that is coincident with or is in the direction away from the body.

As used herein, the term "permeable" refers to a material that allows air and liquid to pass through it to some extent, and not necessarily freely. "air permeable" refers to a material that allows air to pass through it but is at least somewhat impermeable (or in some cases substantially impermeable) to liquid.

Described herein are urine removal device examples that enable urine discharged from a female patient's urethra to be captured by a collection device and drawn out of the device and away from the genital region of the patient by application of suction or negative pressure. The device may be formed of one or more layers of materials, some of which may be hydrophilic, that is tending to attract liquid and others that may be hydrophobic, that is tending to repel liquid. In addition, the layers may all be semi-permeable or at least one layer may be fluid-tight, that is impermeable or substantially impermeable.

The urine removal device may include one or more fasteners or anchors and supports to the respective fasteners or anchors such that enable the device to be removably attached to the region around the female genitalia.

In some examples, a device includes one or more suction conduit members. Each of the one or more suction conduits (which may also be referred to as conduit members) comprise a conduit shaft having one or more fluid inlets, one or more fluid outlets, and a lumen connecting each of the inlet(s) and outlet(s). The one or more fluid inlets of the suction conduit member(s) are positioned within or in fluid communication with the various layers. The one or more fluid outlets of the suction conduit are configured for direct or indirect coupling with a suction source (for example, a vacuum supply). The one or more fluid inlets, one or more fluid outlets and the lumen(s) connecting the two, together define one or more fluid passageways between the layers to the one or more fluid outlet(s) (or a receptacle to which the one or more fluid outlet(s) are connected).

The conduit shaft of the one or more conduits may comprise a rigid, partially rigid, or partially flexible conduit shaft and may be positioned within or affixed to the layers in a manner that provides a rigid or semi-rigid frame that reinforces the device.

The device may include a separate frame that comprises a rigid, partially rigid, or partially flexible structure and may be positioned between or outside of the layers to provide a stiffening structure. The stiffening structure may be shaped such that it flexes when attached to the body, thus forming a preload against the body ensuring that it seats against the anatomy to aid in comfort and preventing leaks.

The one or more conduits may be configured to provide at least a first and a second fluid inlet between two of the layers wherein the first and second inlets are positioned on opposite sides of device. In an example, the first and second inlets are respectively positioned on opposite sides of a longitudinal axis connecting the proximal end and the distal end of the device.

In some examples, one or more of the conduits are provided with an occlusion resistant feature or an anti-kinking feature, comprising one or more accordion pleats or bellows folds at one or more regions of the conduit members. The accordion pleats or bellows folds enable the conduits to resist being kinked, twisted, folded, or collapsed, which maintains the patency of the lumen defined between the fluid inlet(s) and fluid outlet(s) of the conduit member(s) and prevents blockage of the fluid passageway between the fluid inlet(s) and fluid outlet(s). In an example, the occlusion resistant feature or anti-kinking feature may be on the one or more on the conduit shaft(s) of the conduits at a location outside of region between the layers, and, in some examples, may be located between the distal end of the device and a suction source tube, or on the suction source tube.

One or more of the layers may be permeable to air such that air can be drawn through the layer into the device. In some examples, there may be one or more air inlets on at least one of the layers. The inlets may be positioned relatively closer to the proximal end of the device and relatively further from the distal end of the device to help entrain air flow from the proximal end to the distal end of the device. In a specific example, the one or more air inlets are positioned near the proximal end where the layers meet the adhesive patch.

When the urine removal device is disposed on a patient (i.e., when the inner layer lays in contact with the vaginal region), urine released from the urethra moves through the inner layer and onto the middle layer and is drawn (by the application of suction) into the fluid inlet(s) and through the lumen(s) connecting the fluid inlet(s) and the one or more fluid outlet(s) of the conduit member(s), and out of the one or more fluid outlet(s) (for example, into a receptacle to which the one or more fluid outlet(s) are connected). As a result of the application of suction through the conduit member(s), urine released or pooled into the device is readily and hygienically removed from the device and the vicinity of the patient's vagina. Additionally, as a result of the application of suction through the conduit member(s), negative pressure is created and air is drawn through the inner layer or the outer layer as long as suction is applied. The air flow thus generated additionally serves to draw urine and other resident moisture and fluids away from the body and in the direction of the fluid inlet(s). Maintaining the suction and consequent air flow results in urine within the device being quickly drawn out and resultant dehumidification/drying of the device.

Additionally, in the configuration where the one or more conduits are configured to provide at least a first and a second fluid inlet within the device, and the first and second inlets are respectively positioned on opposite sides of a longitudinal axis connecting the proximal end and the distal end of the device, it has been found that the urine removal device proves to work while tilted. When a patient is lying on a side, the device tends to be aligned such that one side is higher than an opposite side, and as a result, urine released from the user anatomy will pool on or at the lower internal side wall. Having multiple fluid inlets distributed on opposite sides of the longitudinal axis ensures that, regardless of which side of the device is positioned lower, there is at least one fluid inlet that is in the vicinity of the pooling urine and through which the urine can be drawn out of the device. Some configurations comprise valves to block the upper conduit, when tilted, to prevent the upper conduit from sucking in air and reducing the suction on the lower conduit that is exposed to fluid.

The fluid collection devices disclose herein are configured to collect fluids from a user. The fluids collected by the fluid collection devices include urine. The fluids collected by the fluid collection devices can also include vaginal discharge, reproductive fluids, blood, sweat, or other bodily fluids.

Specific examples of the invention are now described in connection with the accompanying figures in which like reference characters refer to the same parts throughout the different views. The drawings are not necessarily to scale, emphasis instead being placed upon illustrating examples of the present invention.

In some examples, the device cross-section is relatively flat and elongate and can have a curved shape. The urine removal device can be placed between the patient's legs adjacent to the urethral opening with the flat surface adjacent the urethral opening of the patient and oriented with distal end proximal to the user's anus and the outlet disposed near a proximal adhesive patch that attaches to the patient's abdomen.

Figure 1B:
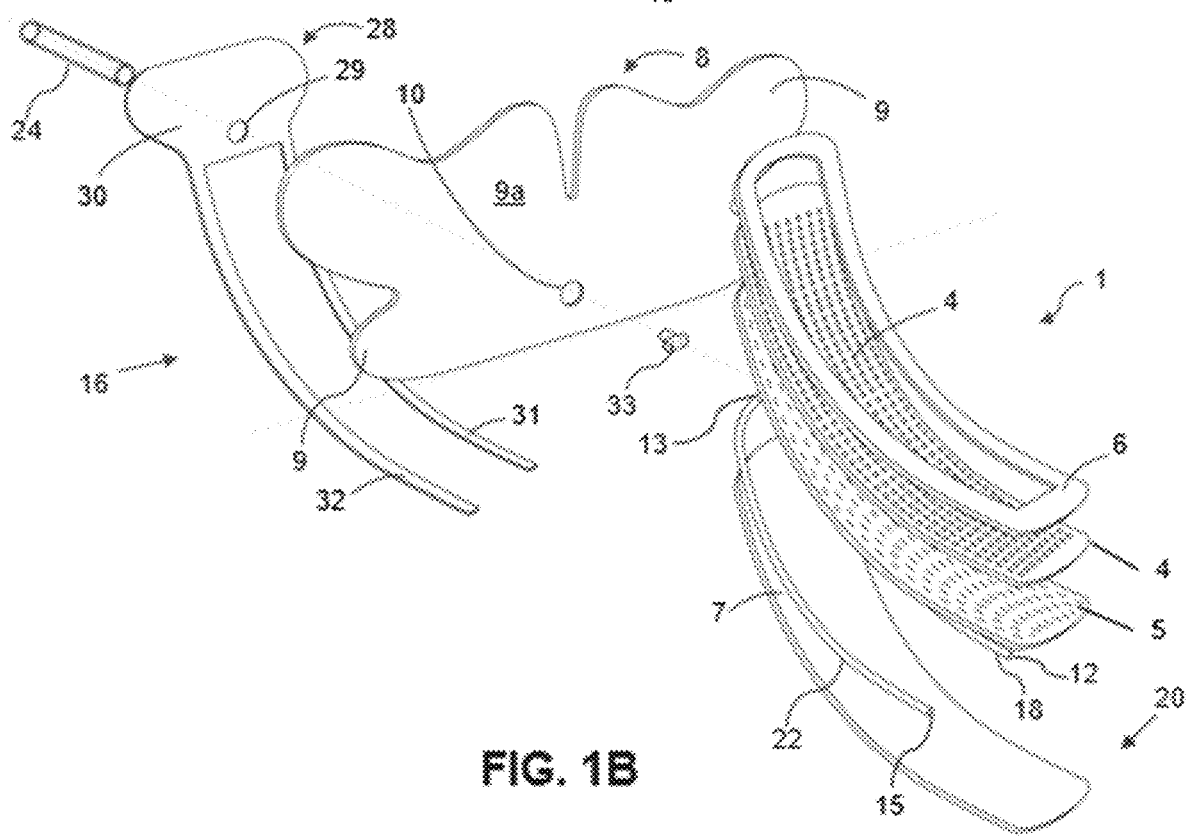
Figure 2A:
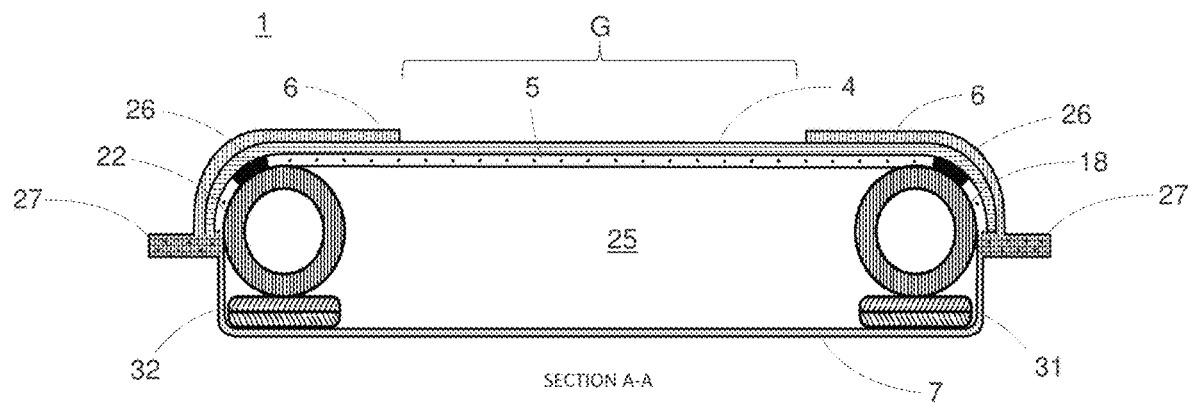
FIGS. 2A-2C illustrate a cross section of a urine removal device in various states.
Figure 2B:
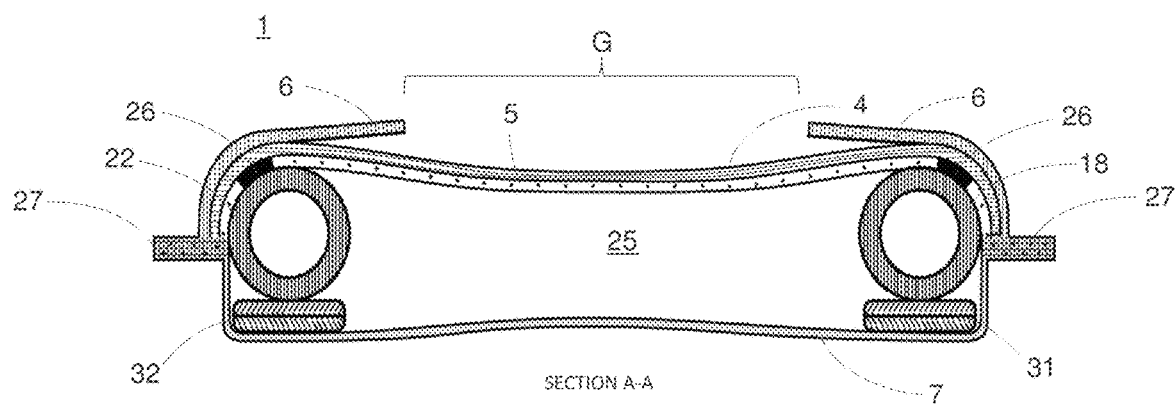
Figure 2C:
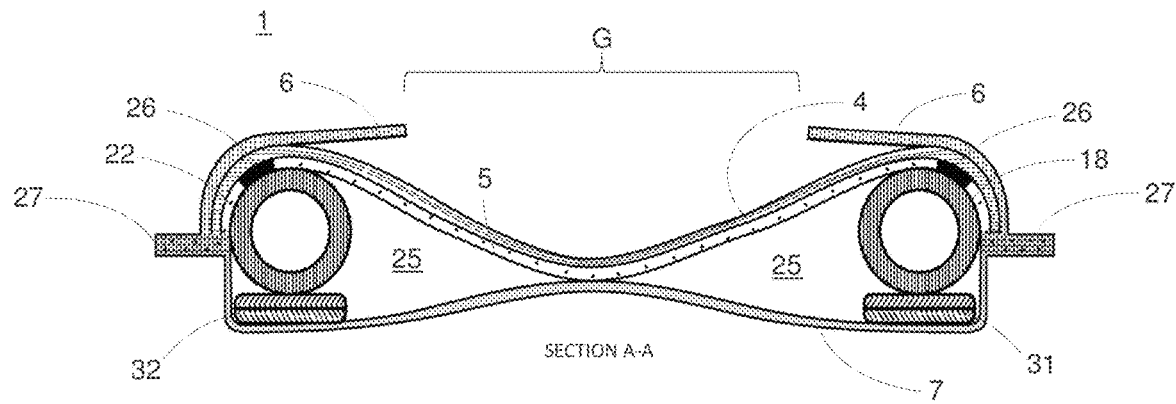

Referring to FIGS. 1A-2C, a urine removal device 1 is shown according to an example. FIG. 1A shows a perspective view of the device 1 while FIG. 1B shows an exploded perspective view of the device 1 to illustrate the interaction of the components more clearly. FIGS. 2A-2C provide a cross-sectional view of the device of FIGS. 1A-1B at section A-A in FIG. 1A.

As shown in FIG. 1A, the example device has an inner layer 4 disposed to contact the patient and an outer layer 7 on the opposite (bottom) side of the device. A flow director layer 5 resides between the inner layer 4 and outer layer 7. It would be understood that in other examples, the device 1 may include any number of layers between the inner layer 4 and outer layer 7. In some examples, the device 1 may have an overhang layer 6 located on the periphery of the inner layer 4. In the illustrated example, the aforementioned layers are joined at least around most of their periphery such that they form an internal compartment between them for collecting and transporting the urine that is captured. In some examples, the overhang layer 6 may be joined to the outer layer 7 while the flow director layer 5 is captive, or in other examples, all of the layers may be joined together.

In some examples, one or more conduits may be located between the inner 4 and outer 7 layers to facilitate the transfer of urine away from the device. For example, FIG. 1A shows a first conduit 18 and a second conduit 22 as hidden lines, extending from the proximal end 16 of the device 1 to near the distal end 20. While the Figures illustrate conduits 18 and 22 as two separate members, in certain examples, the two could be integrated within a single conduit (for example, a u-shaped, c-shaped, V-shaped, or wishbone-shaped conduit having two ends each lying on opposite sides of a longitudinal axis that connects the proximal and distal ends of the device 1. As shown in the figures, each of conduits 18 and 22 respectively has fluid inlet openings 12 and 15, respectively, and fluid outlet openings 13 and 17, respectively, and each conduit 18 and 22 has an internal lumen connecting the respective fluid inlet openings 12, 15 and fluid outlet openings 13 and 17 such that fluid can be drawn from fluid inlet openings 12, 15 through the internal lumen of the conduit 18 and 22 and out of fluid outlet openings 13 and 17.

As illustrated in FIGS. 1A and 1B, the one or more such conduits may be configured such that (i) the one or more fluid inlets 12 and 15 are positioned between the inner 4 and outer 7 layers of the device 1, and (ii) at least a first part of the conduits 18 and 22 is positioned near the distal end 20 of the device 1, and at least a second part of the conduits 18 and 22 is positioned near the proximal end 16 of the device 1. In some examples, a second end of the conduits 18 and 22 may extend out of the layers 4 and 7 and may terminate at a position near the proximal end 16 of the layers 4 and 7, or may terminate at a position beyond the layers 4 and 7 adjacent to the adhesive patch 8. As further described below, where the conduits 18 and 22 terminate proximally, they are in fluid communication with the outside of the device 1 through another conduit (e.g., the suction source tube 24).

In some examples, and as illustrated in FIGS. 1A-1B, a suction source tube 24 resides near the proximal end 16 of the device 1 for connecting to a vacuum supply. The suction source tube 24 connects to the fluid outlet openings 13 and 17 of the first conduit 18 and the second conduit 22, respectively, to draw fluid (urine) from the distal portion 20 of the device 1 and out of the device 1 so that the various layers of the device may be kept relatively dry, and to prevent urine stasis and pooling between the layers. A fastener or anchor such as an adhesive patch 8 may be attached to an external surface of any of the layers or to the base 30 (e.g., base region) of a frame 28 to secure the device 1 to the patient's abdomen, vaginal region, or suprapubic region. The adhesive patch 8 may be a single layer, or it may be comprised of several layers, as described in more detail below.

The device 1 of FIG. 1A is shown in an exploded view in FIG. 1B to further illustrate the relationship of the components and features. The first and second conduits 18 and 22 may connect to an adapter 33, which connects both conduits 18 and 22 to the suction source tube 24. One skilled in the art would recognize that adapter 33 may be a variety of devices to serve the purpose of connecting multiple tubes to one or more outlets; examples include a Y-connector, T-connector, or a manifold. Alternatively, the first and second conduits 18 and 22 may be made integral to the suction source tube 24 so that a connector is not required. The conduits 18 and 22 may be retained by one or more attachments 26 (further described below).

The one or more conduits 18 and 22 may be rigid or flexible, and are positioned in a manner that can stiffen the device 1 depending on the stiffness of the conduits 18 and 22. In some examples, the conduits 18 and 22 are highly flexible such that they contribute negligible bending stiffness to the device 1. Furthermore, in some examples, a frame 28 is attached within or outside of layers 4 and 7 to provide stiffness and a preformed shape to the device 1. The frame 28, formed by one or more branches 31 and 32 attached to a base 30, enables the device 1 to resist deformation or kinking in a manner to resist the occlusion of fluid flow between the sides or ends of the device 1 while providing a pre-set shape to the device 1 which may be deformable or malleable. The frame 28 may be attached to the front or back side of the adhesive patch 8 and both the adhesive patch 8 and the base 30 of the frame 28 may have apertures 10 and 29, respectively, through which the suction source tube 24 or the adapter 33 that connects the suction source tube 24 to the conduits 18 and 22 passes. In this sense, the frame extends from the layer portion of the device to the patch providing a structural link to the patient's body and providing stiffness to the device 1. The base 30 acts as a reinforcement to the adhesive patch 8 so that the branches 31 and 32 have a relatively strong root so that they can behave like beams. Finally, the frame 28 may reduce deformation of the device that may lead to a vacuum lock as described below.

Further considering FIG. 1B, the adhesive patch 8 may be comprised of single or multiple layers that include a substrate layer 9 having an outer surface 9a, which is attached at least one layer. Alternatively, the adhesive patch outer surface 9a may attach to the base 30, which in turn attaches to at least one layer. The inner layer 4 functions to contact the patient and pass urine through to the device for transport out of the device which may help to maintain the device surface proximal to the patient anatomy dry over an extended period of time. As such, the inner layer 4 should be soft and relatively dry to the touch much like a sanitary pad. The inner layer 4 may be perforated and substantially non-absorbing, such as made of a hydrophobic material. The inner layer 4 may be made of any suitable material that is highly flexible, i.e., low in flexural modulus and/or thin-walled. In addition, the material may be chosen in some examples so that the resulting wall has a thickness of about 5-100 µm, or in some examples the thickness may be up to 1 mm. The inner layer 4 is liquid permeable and may be heat weldable, or may otherwise be laminated, bonded, or solvent bonded, to another flexible wall. Examples of suitable materials may include but are not limited to, perforated or unperforated woven or non-woven fabrics, polyurethane, ethylene vinyl acetate, polyethylene, silicone, rubber, latex, polyolefin, or any other suitable thermoplastic polymer or natural material. Furthermore, the layer may be made fully or partially of an odor-blocking material such as a polyamide, polyvinylidene dichloride, biaxially oriented polypropylene, natural rubber latex, silicone rubber, coated or uncoated synthetic or natural fabrics, ethylene vinyl alcohol or EVOH or similar materials, or alternatively, the odor-blocking material may comprise one or more films coextruded with other suitable materials or otherwise attached to the layer. In some examples, a material may be treated with an additive or coating to make it hydrophobic to a degree desired for the function of the layer.

The flow director layer 5 aids in transporting fluid to the suction inlets when under vacuum, thus the flow director layer 5 may be considered an "acquisition distribution layer" (ADL). In some examples it can be a hydrophobic material that is non-absorbant. The flow directing layer may be made of a polymeric material, including any of the polymeric materials described herein. The flow director layer 5 materials are described in more detail with respect to FIGS. 7A-7C below. The outer layer 7 functions to retain fluid within the layup and is configured to prevent urine flow from the inner layer(s) to the environment. In some examples, it is made of air-permeable, non-woven fabric, that is liquid-impermeable, hydrophilic and non-absorbent. The liquid-impermeable, hydrophilic, non-absorbent properties of this layer help it to mitigate wetting of the outer layer 7, allow fluid retention within the internal chamber of the device and to facilitate suction. In use, the device may keep the patient feeling dry because the vacuum operates to remove moisture from the device 1 continuously or periodically. In some examples, the outer layer 7 may be made of a material that is permeable to air (i.e., breathable) but substantially impermeable to liquids. This allows the layer 7 to draw in air to accelerate drying. Two properties that can be used to improve performance of the outer layer 7 are hydrophobicity of the layer or the pore size of the layer. If the layer is hydrophobic, it will repel water thus not allowing it to permeate or it can have small pore size that will let air pass through while retaining liquid. This material may be described as spunlaid, flashspun, melt-blown, air-laid or staple nonwovens. The fibers may be made of a single, or multiple materials which may be extruded together in base/ binder configuration, or as distinct fibers. The ratio of materials may be varied to achieve desired properties. The final fabric may have a sheet weight of about 5-1000 gsm and a thickness of approximately 5-1000 microns, in some example embodiments. Example materials include those that are hydrophobic and non-woven or other membranes or sheets such as, for example, PTFE membrane used in gas release filters—these membranes have small pores that let the air through but retains liquids. Other examples of suitable thermoplastics include but are not limited to: polyethylene, polypropylene, polyethylene terephthalate, polyamide, polyvinyl chloride, polyester, polyether, polyurethane, polytetrafluoroethylene, block-copolymer elastomers, polyamid. Examples of suitable thermosets/rubbers include but are not limited to: butyl, chloroprene, epichlorohydrin, ethylene/acrylic, ethylene-propylene, fluorocarbon, fluorosilicone, silicone rubber, natural rubber, nitrile, hydrogenated nitrile, perfluoroelastomer, polyacrylate, polysulfide, styrene butadiene. Examples of suitable natural fibers include but are not limited to: linen, silk, and wool.

Now with reference to FIG. 2A, which shows SECTION A-A, a cross section taken through the device 1 at the location designated in FIG. 1A, illustrating the layup and attachment configuration in this example. One skilled in the art would recognize that there are many ways to attach various layers including thermal bonding (heat staking) or adhesives such as epoxy, glue, UV cure adhesive, etc., all of which are within the scope of this disclosure. The overhang layer 6 spans the outboard regions of the outer surface of the device 1 leaving a gap G where the inner layer 4 is exposed so that it may interface with the anatomy to collect fluid. The overhang material may be made of the same material as the outer layer 7 or other sheet materials made of polymers or natural materials. The overhang layer 6 may be made of a semi-permeable material or a material that is breathable yet substantially impermeable to liquids. The overhang layer 6, the inner layer 4, and the flow director layer 5 all pass over the conduits 18 and 22 to where they are joined together with the outer layer 7 at the seam 27. The seam 27 may extend laterally as shown and during manufacturing it may be trimmed to remove it as flash. A plurality of attachments 26 may connect the conduits 18 and 22 to the device 1 to locate them at the lateral portions of the layers, as shown. The attachments 26 may be formed via heat staking (thermal bonding), adhesive bonding, or any other method for joining polymeric materials.

FIG. 2A shows a configuration wherein the layers 4, 5, and 7 are taut (e.g., are under tension), and, as such, shown straight in the figure. In use, the first conduit 18 and second conduit 22 are flexible and may flex inward, due to pressure from the user's legs. As a result, the layers may not be in a taut configuration in use, and may be loose as shown in FIGS. 2B and 2C. Notably, the configurations shown in FIGS. 2B and 2C may be as-manufactured. In FIG. 2B, the layers 4, 5, and 7 are curved inward, somewhat reducing the void 25 (or cavity) inside of the device. FIG. 2C shows a more pronounced bowed configuration where the flow director layer 5 is actually in contact with the outer layer 7. In both FIGS. 2B and 2C, the overhang layer 6 is shown separated away from the inner layer 4 which may occur at times because the layers 4 and 6 are not fully attached to each other. The lack of attachment may allow the overhang layer 6 to act as a gutter to catch fluid that otherwise may drip off of the side of the inner layer 4. In each of FIGS. 2A-2C, the void 25 that exists inside of the device between the layers is different, and in FIG. 2C there are multiple voids arising from the contact region between the layers. In use, as the device 1 lays up against the anatomy and various forces act on different parts of the device 1, therefore, the void 25 may take various shapes along the length of the device 1 and it may be quite variable from relatively open to substantially closed. The device 1 does not require a significant void to operate because suction draws urine distally both through the void 25 and along the surfaces of the various layers. Even if the layers are in contact, a viable flow path still exists for the wetted layers to channel flow to the suction conduits.

The void 25 provides for a light-weight and dry device in contrast to a device with a filler that tends to hold moisture, even as it is being evacuated. The thin walled, light weight, low mass structure of the device examples disclosed herein provide a structure that evacuates fluid quickly.

In some examples, the conduits 18 and 22 may be located more inboard, or in the center, or there may be a single conduit in some examples. The attachments 26 may join the conduits 18 and 22 to any of the layers or the support frame. In some examples, one or more of the layers may terminate at the attachment 26 and do not extend laterally to the seam 27. In some examples, and as shown in FIGS. 2A-2C, the overhang layer is not attached to the inner layer 4 for at least of portion of its inboard span. This allows the overhang layer 6 to catch some fluid residing within or on the inner layer 4 that may drip to the side when the device 1 is tilted during use. The device 1 is supported by the frame, and in FIG. 2A, the first branch 31 and second branch 32 of the frame are shown adjacent to the conduits 18 and 22, respectively. In this example, the branches 31 and 32 are within the outer layer 7 and inner layer 4, but in some examples, they may be outside of the outer layer 7 or above or within the conduits 18 and 22 and below or above any of the layers 4,5, and 6.

As shown in FIGS. 2A-2C, the branches 31 and 32 may have multiple layers, as shown in this example where each branch has two layers. In general, the branches may be comprised of multiple layers of beams that may have different lengths, or shapes, as described further below and illustrated in FIGS. 8A-19. Thus, the stiffness of the frame may be tailored to have, for example, a decreasing stiffness along the branches by staggering beams, tapering them, or otherwise affecting the cross-section to achieve the desired compliance.

The conduit attachments 26 hold the conduits 18 and 22 in place relative to the layers, thus creating the void 25 within the device 1. As described above, due to the lateral flexibility of the device 1, the void 25 may not be uniformly shaped in some circumstances. For example, as the anatomy squeezes the device (between the legs) the layers may be come loose and even touch, however, the vacuum and/or capillary action of the layers will still facilitate near drying of the device. One skilled in the art will recognize that there are many other alternative methods to locate and hold the conduits, such as bonding a small spacer between the walls adjacent to the conduit members, or forming the walls in a manner to create a feature protruding into the space between the walls deep enough to retain the conduit members. The layers may be joined (seam 27) and the conduit attachment 26 may be created by any method for connecting polymers such as, for example, bonding with an adhesive, solvent bonding, or thermal bonding (heat staking). In other examples, the conduits may be directly joined to the inner layer 4, the flow director layer 5, or the outer layer 7, or all layers, using a suitable joining process. In some examples, the conduits may be located external to the layers except at the distal tip of each conduit where they enter into the void 25 to provide suction at the distal portion of the device. The conduit attachments 26 hold conduits in place against the layers to prevent the undesired movement which may cause the device 1 to assume a folded or kinked configuration, resulting in occlusion of the fluid inlet openings 12 and 15 of the conduits 18 and 22, respectively, or in blockage of a fluid flow path between a region in which urine has accumulated within device 1 and one or more of the fluid inlet openings 12 and 15. In some examples, the conduits 18 and 22 may be preloaded outward such that they bear against the outer region at the seam 27 thus applying tension to the layers 4,5, and 7. In such examples, the conduits may not need any attachments to the layers.

Figure 3:
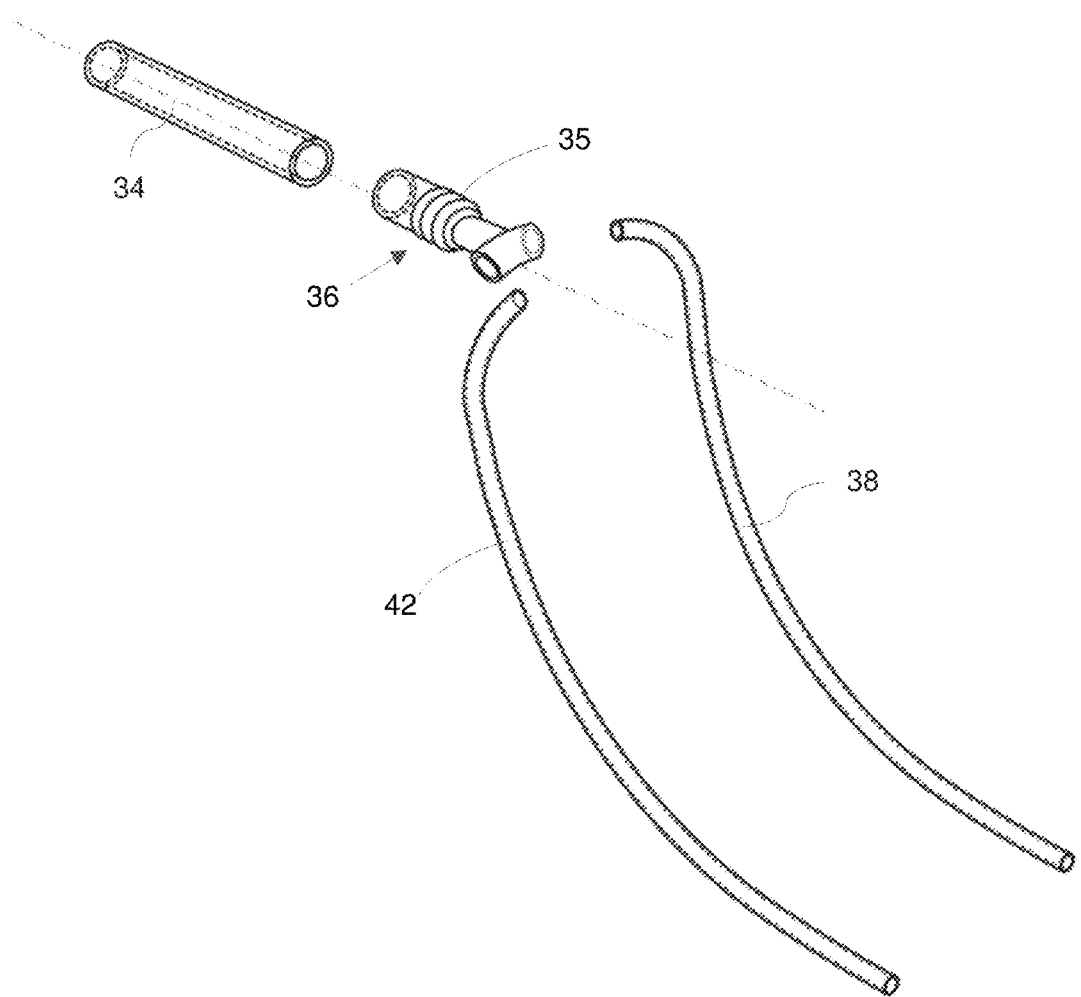
FIG. 3 illustrates a conduit system for a urine removal device.

Now with reference to FIG. 3, which shows an alternative conduit system having a connector 36 comprising a flex joint 35 that serves as an occlusion resistant feature or an anti-kinking feature located on or near the suction source tube 34. The flex joint 35 prevents the suction source tube 34 and conduits 38 and 42 from being kinked, twisted, folded or collapsed, thus maintaining the patency of the lumen defined between the fluid inlets and fluid outlets of the conduits 38 and 42. As shown in FIG. 3, the flex joint 35 may be located on the connector 36 which joins the suction source tube 34 with the conduits 38, and 42. The flex joint 35 may comprise one or more accordion pleats or bellows folds or other features creating a joint or strain relief that enables the suction source tube 34 or any of conduits 38 and 42 on which it is provided to resist being kinked, twisted, folded, or collapsed. In an example, the flex joint 35 is provided either (i) at a junction between suction source tube 34 and conduits 38 and 42, or (ii) proximal to the junction between suction source tube 34 and conduits 38 and 42, toward the suction source. The flex joint 35 provides a strain relief to isolate the device (layers and fluid containment region) from forces on the suction source tube 34 or other tubes connected thereon. For example, when the patient is treated, the suction source tube 34 may be bumped or pulled causing it to pull on the device, and in particular the adhesive patch that is attached to a sensitive area on the patient. As such, the flex joint 35 tends to reduce these forces transferred to the patient.

The various components of the conduits systems shown herein may not be discrete pieces. In some examples, the conduit system may be contiguous such that the conduits, the connector, and the suction source tube are made from one contiguous part. In other examples, the connector may be integral to the suction source tube and attached to the conduits, for example.

One skilled in the art will recognize that there are many implementations of a conduit system that reduces the likelihood of kinking or folding. For example, in some examples, the conduit or channel may be integral to a layer. In other examples, the device may be reinforced in the area where the conduits or suction source tube attaches, or the suction source tube may protrude far enough between the layers to reduce the likelihood of a pinch point at the joint.

Figure 4A:
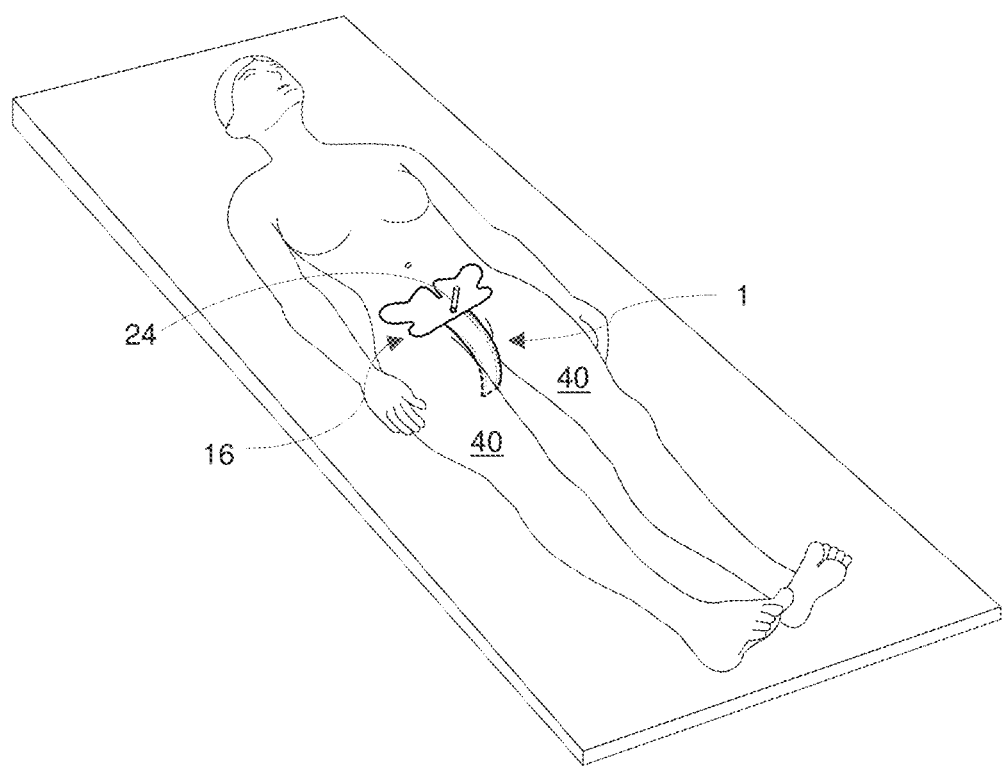
FIG. 4A illustrates a prone patient wearing a urine removal device according to an example embodiment.
Figure 4B:
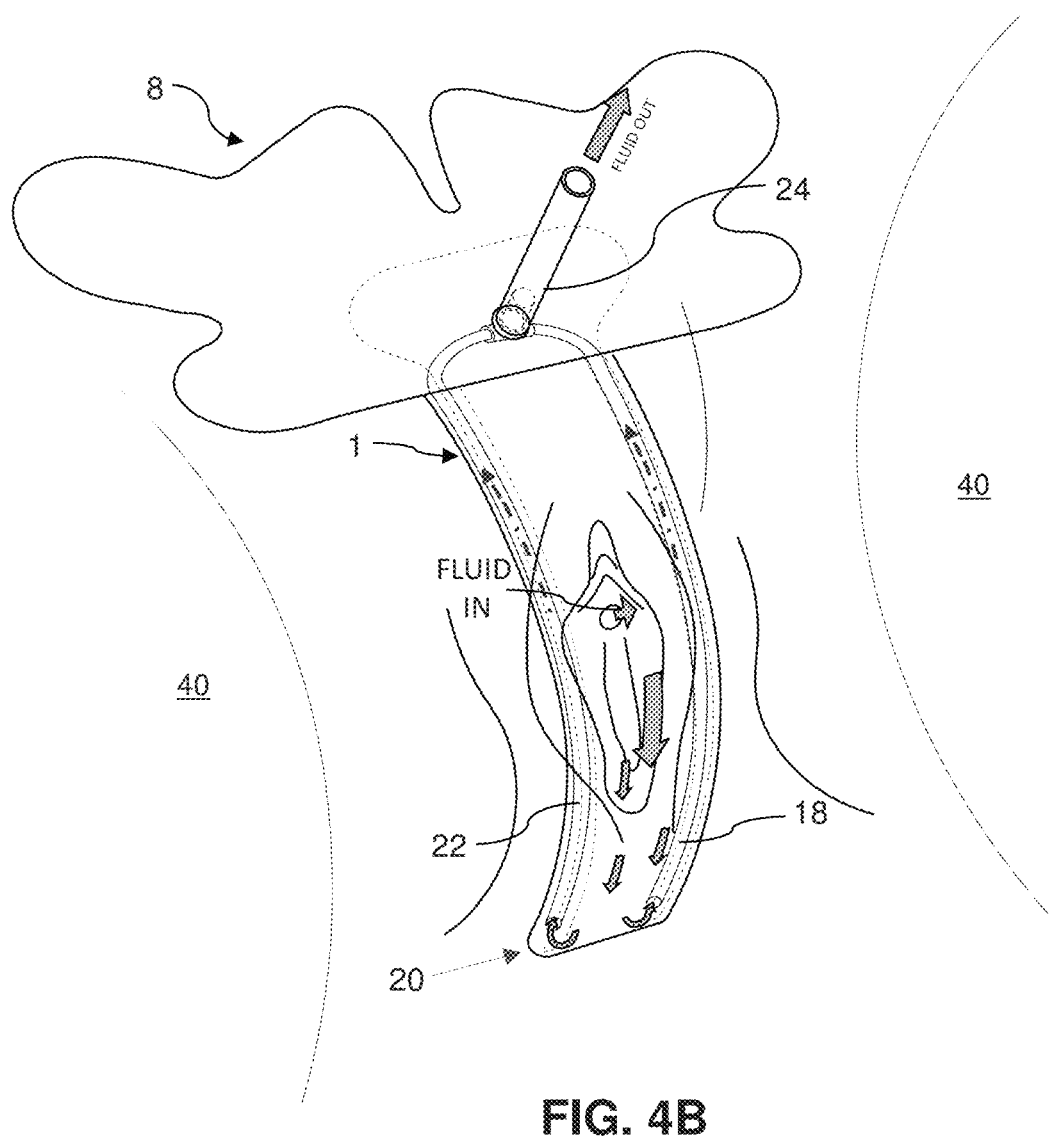
FIG. 4B illustrates a close-up view of the urine removal device of FIGS. 1A-1B placed on a patient with urine flow paths designated.
Figure 4C:
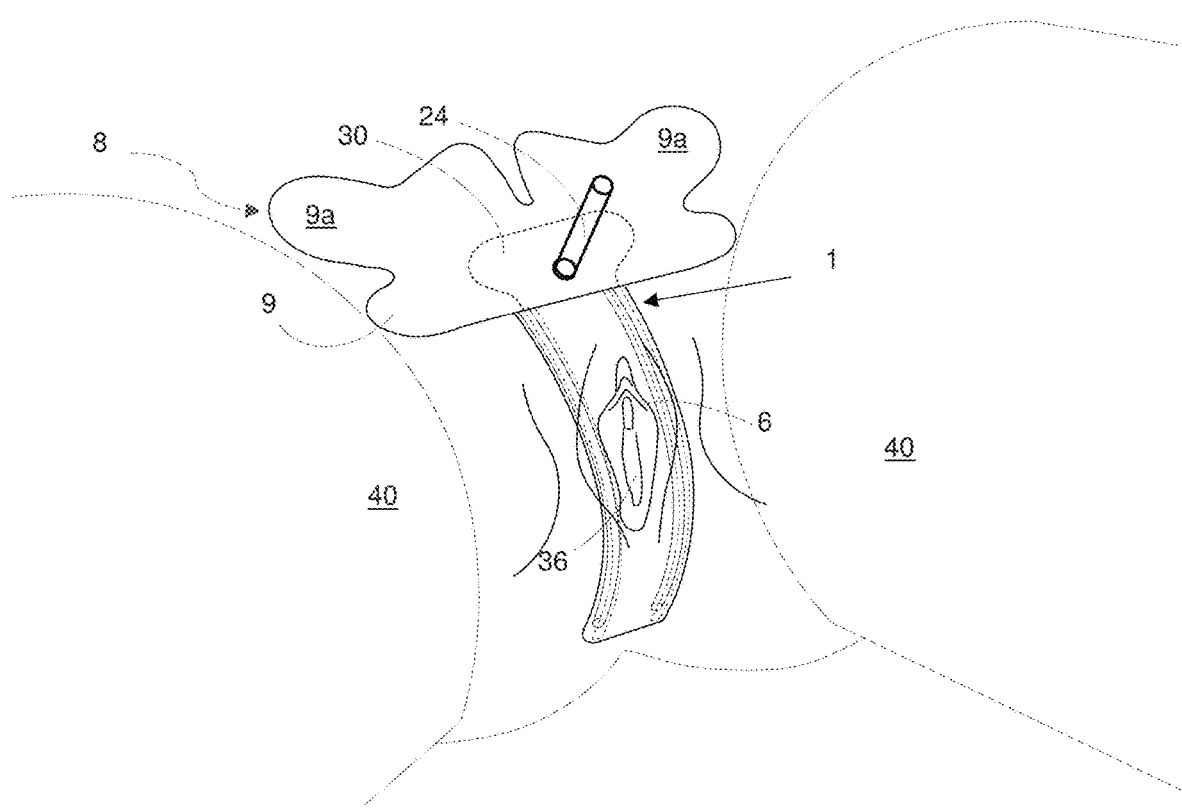
FIG. 4C illustrates a close-up view of the urine removal device of FIGS. 1A-1B placed on a patient detailing the orientation with respect to the vagina.

One example of a urine removal device is shown in an exemplary patient use scenario in FIGS. 4A-4C. As illustrated in FIG. 4A, the patient is shown laying supine with the urine removal device 1 attached. In this example, the device 1 sits between legs 40 such that the suction source tube 24 resides near the lower abdomen rather than between the legs, as is the case with commonly used urinary incontinence devices. This arrangement addresses the problems of the tube contacting the patient's legs and the associated discomfort, pressure point injuries, kinking, leakage, and tangling because no hoses or tubes are residing on or between the legs.

Now with reference to FIG. 4B, the urine collection device 1 is attached to the body via the adhesive patch 8, through which the suction source tube 24 passes; the suction source tube 24 is in fluid communication with a vacuum source, which provides suction pressure to the conduits 18 and 22 such that they extract urine from the distal end 20 of the device 1. FIG. 4B illustrates the manner in which urine released into the urine removal device 1 as indicated by the "FLUID IN" arrow (by a user's urethra when it is positioned proximate to the device 1). The urine is drawn by negative pressure applied by a vacuum source, along the device in the direction of the arrows, into conduits 18 and 22 and out of suction source tube 24. The urine removal device draws in air while under suction pressure and one or more of the layers may be permeable to air either due to the material composition of the layer or due to holes through the layer, or a combination of both. To facilitate continued suction and the flow of urine, one or more air ports may be located on at least one layer to allow air into the device 1. Ingress of air helps to prevent a vacuum lock condition which may reduce or stop the flow of urine into the conduits. As used herein, the term "vacuum lock" refers to a condition wherein when vacuum is applied to a cavity with flexible walls, the walls may be sucked into contact, thus restricting or preventing a liquid or gas from flowing through the cavity because the approximated walls reduce or eliminate viable flow paths. One skilled in the art will recognize that air ports and air-permeable layers may be located at alternative locations to provide an air conduit into the interior of the device.

Now with reference to FIG. 4C, which illustrates how, in some examples, the adhesive patch 8 may attach to the body. This view shows the outer surface 9a of the substrate layer 9, which attaches to the base 30 of the frame 30 and optionally to at least one of the layers (e.g., inner layer, flow director layer, or outer layer) of the device 1. The inner layer (hidden) of the adhesive patch 8 contacts the body and comprises an adhesive that allows it to adhere to the pelvic/lower abdomen region, even overtop hair follicles, skin folds, wrinkles, as well as the sweat and moisture that may precipitate in the groin area, while being painless to remove from the body. One skilled in the art would recognize that there are many appropriate adhesives including porous and nonporous silicones. Adhesive patch examples are described in further detail below.

Figure 5A:
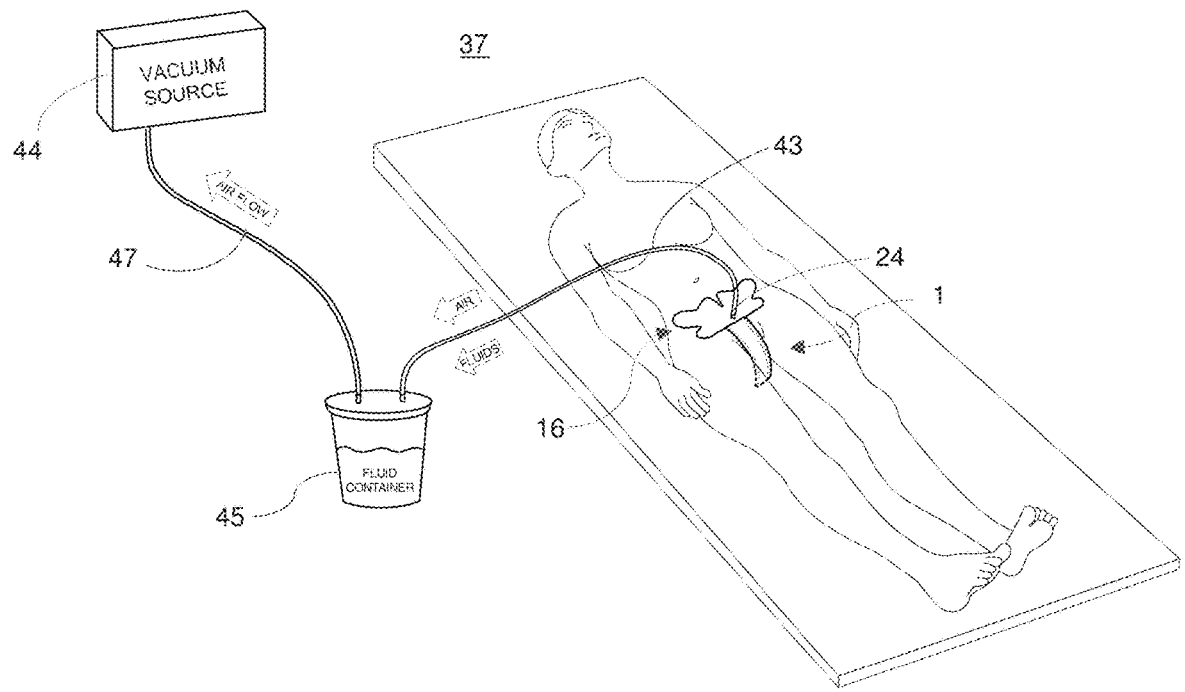
FIG. 5A illustrates a urine management system according to an example embodiment.
Figure 5B:
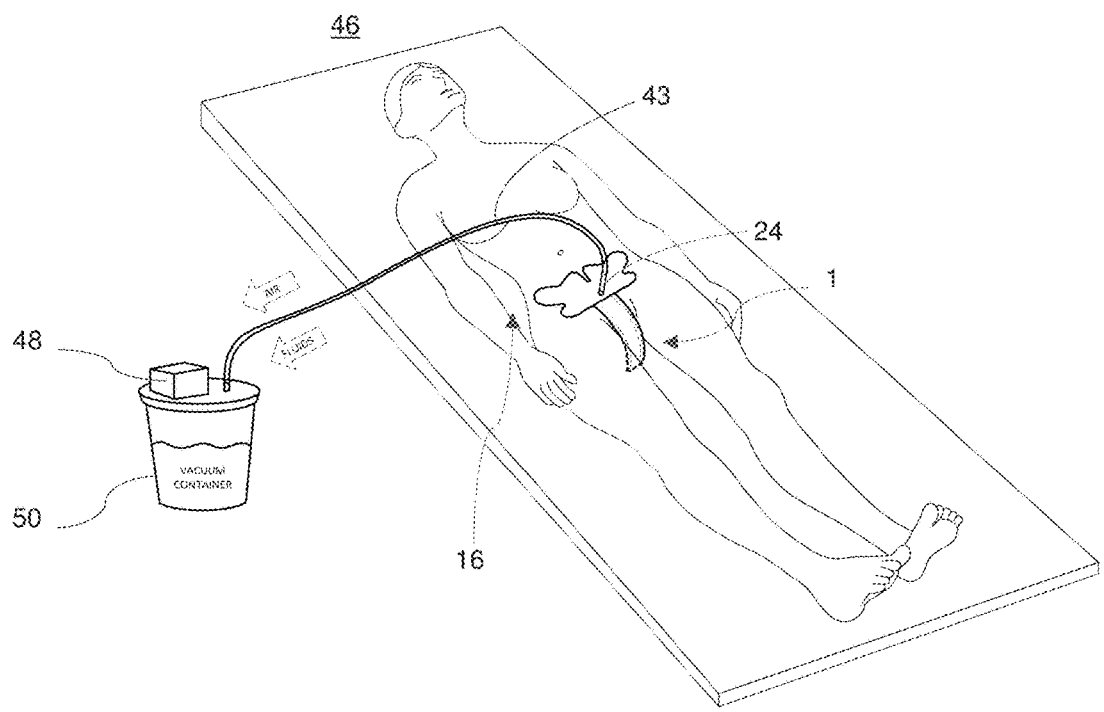
FIG. 5B illustrates a urine management system according to another example embodiment.

Vacuum-assisted urine collection systems typically have a suction tube that runs from the outlet tubing, across the patient, to an external collection system. Conventional effluent collection systems for urine and stool have drainage tubing connection points between the legs, which may lead to leg-entanglement or obstruction from a limb or bedding, and is a known risk factor pressure point injuries and skin breakdown. Placing the access point in the suprapubic region and draping the tubing over the pelvis, hips, or midsection reduces these risks. FIGS. 5A and 5B illustrate simplified schematics of urine management systems for collecting urine according to example examples. As shown in FIG. 5A, the urine management system 37 includes the urine removal device 1 described above, a drain tube 43, a urine collection reservoir 45, a vacuum source tube 47, and a vacuum source 44.

The proximal end 16 of the urine removal device 1 is coupled to the drain tube 43, which interfaces with the suction source tube 24. Any type of connector know by those in the art may be used to connect the drain tube 43 to the suction source tube 24 while being within the scope of this disclosure; examples include a Luer lock, thread, step, or other connector with or without one-way valve. Alternatively, the drain tube 43 and the suction source tube 24 may be one contiguous tube. The drain tube 43 may be a flexible tube that can be manipulated by the practitioner and draped over or under the arm. Notably, the drain tube 43 attaches to the proximal end 16 of the device 1 such that it passes over the abdomen rather than between the legs, where it is directed away from the body (e.g., off of the bed). This arrangement reduces entanglement with the legs and bed sheets covering the legs and reduces accidental pulling of the drain tube 43 from the suction source tube 24, thus preventing leakage when the patient moves and turns in bed while reducing the discomfort of having a tube winding amongst the legs. Having the drain tube 43 accessible across the middle of the body also provides easy access for healthcare practitioners as they do not have to search for the drain tube 43 between or underneath the legs and bedding.

The opposite end of the drain tube 43 is coupled to the urine collection reservoir 45 which contains the urine drawn from the drain tube 43. The urine collection reservoir 45 may be a urine collection bag, such as a leg bag or drainage bag, or another container such as a bottle, bucket or canister. The urine collection reservoir 45 may be a sealed device to reduce spillage; in some examples, it may be a disposable unit, or it may be a reusable unit that may be washable and/or sterilizable.

The urine collection reservoir 45 connects to the vacuum source 44, which applies vacuum pressure to the vacuum source tube 47 and drain tube 43 to assist in directing the urine from the suction source tube 24 to the urine collection reservoir 45. The vacuum source 44 may be a wall vacuum integrated into a room of a medical facility to its central vacuum generation unit. In other examples, the vacuum source 44 can be integrated with the patient's bed. In general, the urine collection reservoir 45 may include a filter or valve system to prevent urine from transiting up the vacuum source tube 47 and into the vacuum source 44. The urine management system 37 may also include a clip or valve for shutting off the supply of urine from the drain tube 43 so that the urine collection reservoir 45 may be emptied or changed.

Another example of a urine management system 46 is illustrated in FIG. 5B; this example differs from the urine management system 37 of FIG. 5A in that the urine collection reservoir 50 has an onboard vacuum generating unit 48 to create vacuum independently of any hospital or facility vacuum source. Thus, the second end of the drain tube 43 connects into the collection reservoir 50, which has a vacuum generating unit 48 to draw urine into the collection reservoir 50. Since there is no requirement for hospital/facility wall suction, this urine management system 46 offers more flexibility for use in the home, hospice, or long-term care, for example. Additionally, in some examples, the onboard vacuum generating unit 48 may be powered by onboard batteries, obviating the need for a power plug and a wall power source, thus providing more flexibility for use in different locations and settings such as a mobile platform, mobile bed, or wheelchair. The urine collection reservoir 50 may be fully reusable, or disposable, or in other examples, the urine collection portion may be disposable while the onboard vacuum generating unit 48 may be disposable or reusable.

Figure 6A:
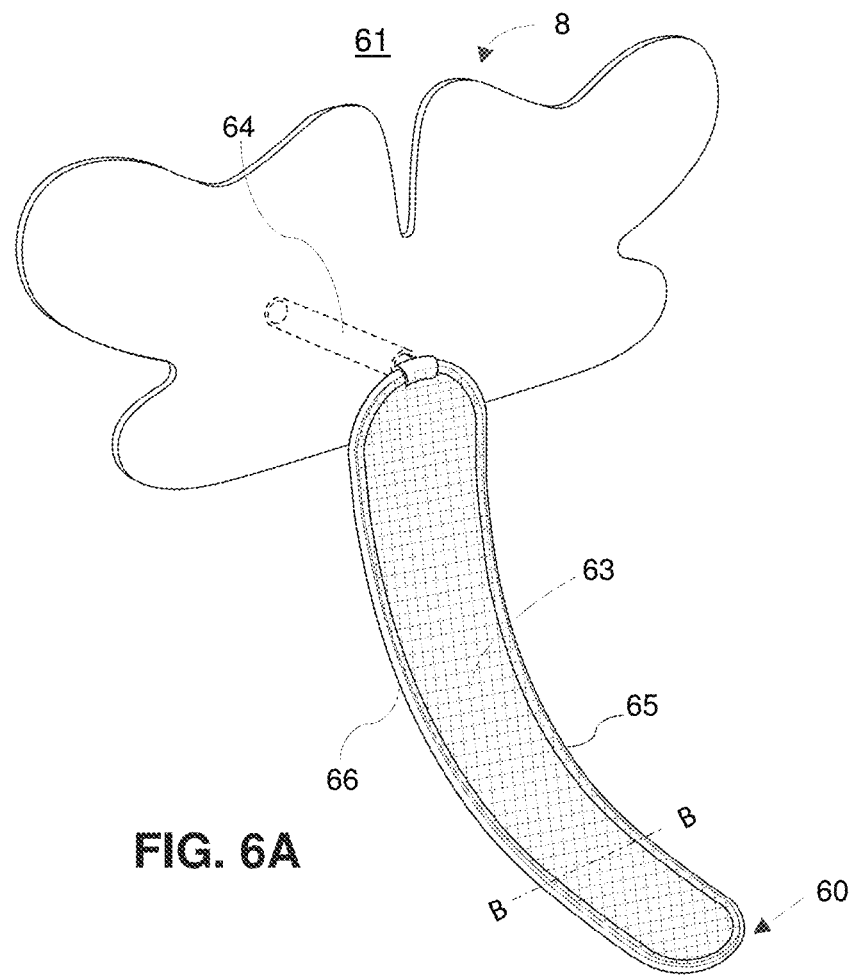
FIGS. 6A and 6B illustrate a perspective view and a cross-sectional view of an example embodiment of a urine removal device.
Figure 6B:
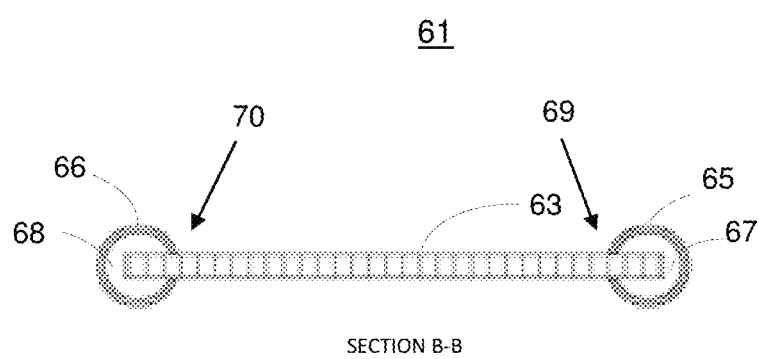

FIGS. 6A-6B illustrate another example of a urine removal device having one or more layers embedded into a conduit. The urine removal device 61, as shown in FIG. 6A, has a layer 63 disposed to contact the patient and configured to divert urine toward conduits 65 and 66 disposed at the sides of the device 61. In some examples, the layer 63 may be a flow director layer (similar to that shown in FIG. 1A and described elsewhere in this disclosure) or an acquisition distribution layer (ADL). Although only shown as one layer in FIGS. 6A-6B for simplicity, the layer may comprise multiple layers such as, for example, an inner layer, flow director layer, and outer layer as shown in FIG. 1A; wherein the flow director layer resides between the inner layer and outer layer. It would be understood that in other examples, the device 61 may include any number of layers. In the illustrated example, the layer 63 is joined at least around most of the periphery with the first conduit 65 and the second conduit 66.

FIG. 6B is a cross-sectional view taken from FIG. 6A showing the interface between the layer 63 and the conduits 65 and 66. The layer 63 is embedded into the conduits 65 and 66 via slits 69 and 70, respectively, in the conduits 65 and 66. The slits 69 and 70 provide access into the lumens 67 and 68 of the conduits 65 and 66 respectively so that the urine or within the layer 63 can be drawn into the conduits by vacuum. This arrangement provides a suction all along the sides of the layer 63 to draw urine across the relatively short width of the layer 63 to extract the urine quickly. Urine may be extracted more efficiently if the layer 63 (or one or more layers) has flow directing features oriented such that they channel flow laterally into the conduits 65 and 66.

The conduits 65 and 66 are connected to each other at the distal end 60, as shown in FIG. 6A, and comprise one contiguous conduit as shown. In other examples, the conduits on each side may each terminate at the distal end 60 having a blocked end condition that does not draw in air. As in other examples presented herein, the conduits 65 and 66 may be connected to, or integrated with, a suction source tube 64, and the device 61 may have an adhesive patch 8 and a frame (not shown).

Figure 7A:
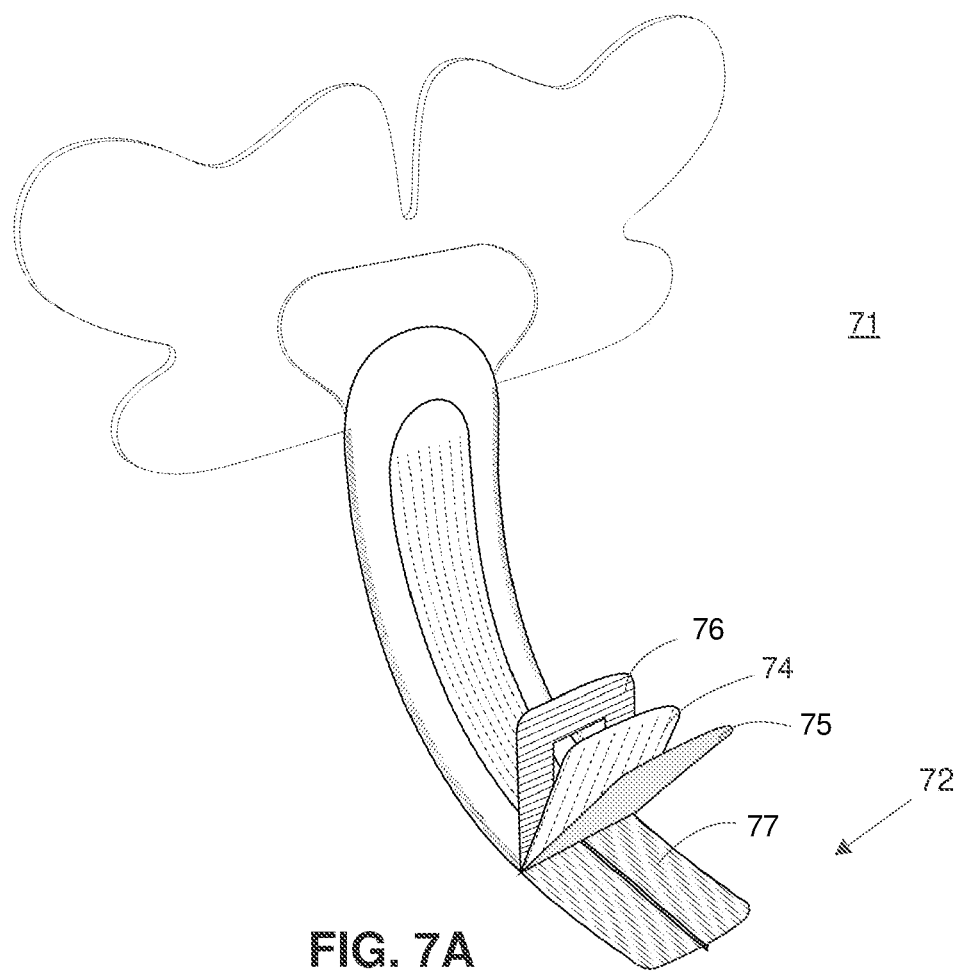
FIG. 7A illustrates a perspective view of a device having oriented flow directors on a layer according to an example embodiment.
Figure 7B:
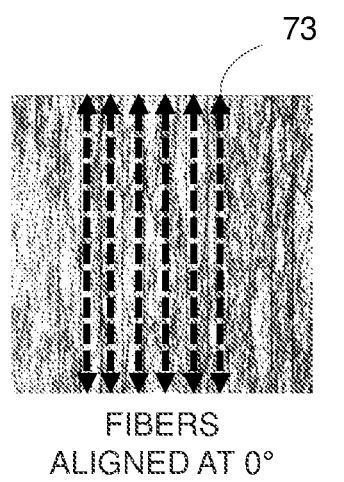
FIGS. 7B and 7C illustrate fibers oriented on a surface at angles of 0 deg. and 90 deg, respectively.
Figure 7C:
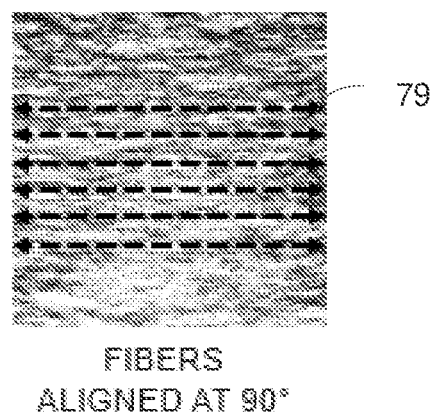

Referring now to FIGS. 7A-7C, a simplified device 71 is shown to illustrate examples of a flow director layer, i.e., the device 71 may have conduits, etc. as shown in the device 1, but these features are not shown. The device 71 has an outer layer 77, a flow director layer 75, an inner layer 74, and an overhang layer 76. The flow director layer 5 is configured to capture and divert urine received from patient anatomy, down and towards the suction inlet(s) disposed within the device. This layer, for example, may be made of a non-absorbent, super wicking, non-woven material that is configured to have high wicking rate along the length of the device, when compared to the wicking rate along the width of the device. The flow director layer 75 may have features that tend to direct the flow in a desired direction for faster evacuation and drying. For example, the device of FIGS. 1A-1B has conduit inlets at the distal end 72 of the device, so flow directors oriented longitudinally may be beneficial. In contrast, the device of FIGS. 6A-6B has conduits that are in fluid communication with one or more layers along their length, so flow directors oriented laterally may be beneficial to enhance flow across the short lateral distance to the conduits. Flow directors may be either molded, hot-rolled, deposited, bonded, spray-coated, etched, formed or embossed or attached as a laminate on one or both sides of the flow director layer 75 which is disposed between the outer layer 77 and the inner layer 74. The flow director layer 75 resides may be floating, that is not directly attached, or it may be attached to one or both layers 77 or 74 by, for example, lamination, bonding or heat staking. One skilled in the art will recognize that there are many types of flow directors and concomitant manufacturing and attachment methods that serve to separate the walls and provide small channels for fluid to pass, and several examples will be described in more detail below.

As noted above, flow directors may be located on any one or more of the layers of the device 71. In some examples, the flow directors may be any type of texture that tends to keep the layers separate in at least some areas of the inside internal compartment of the device so that liquid (urine) and air may flow without having a partial or total vacuum lock condition—a condition wherein the layers stick together due to the air suction and/or capillary or stiction forces between the layers. As described above, the flow directors may have some preferential orientation, either entirely across the surface, or on average, such that urine is channeled from one end to the other end of the device as it is drawn by the tips of the conduit members.

The orientation of the flow directors is further emphasized in FIGS. 7B-7C, which show various orientations of the directors with respect to the longitudinal (proximal to distal) axis of a device. FIG. 7B shows a section of a layer with directors indicated by shaded striations oriented along 0 degree vectors 73 indicating alignment with the device longitudinal axis, as described below in more detail. FIG. 7C shows a section of a layer with directors indicated by shaded striations oriented along 90 degree vectors 79 indicating orthogonality with the device longitudinal axis. Depending on the structural features used to create the flow directors, they may or may not be fully aligned homogenously. That is, a distribution of channels, fibers, or whiskers may have a net orientation along the 0 degree vector 73 orientation, but there may be a distribution of angles due to manufacturing processes such that the average angle of these features aligns approximately with the vector 73 orientation (approximately 0 deg.).

In some examples fibers may serve as flow directors, and they may be attached to any of the layers described above, or the fibers may be attached to a substrate that is, in turn, attached to one of the layers. The manufacturing process to create such a flow director layer may involve having the fibers of the non-woven fabric laid down along a moving conveyor belt, predominantly oriented along the length of the conveyor, and then blown with hot air to melt them together. This fabric may then be described as melt-blown, air-laid, or hot air through. The fibers may be made of a single, or multiple materials, for example, wherein two materials (e.g., PE and PP) are joined together in small extruders such that each strand has both materials in a base/binder configuration, or in their distinct formats. The base/binder ratio may vary, for example, from 1:50 up to 50:1. The final fabric (sheet) that contains the fibers may have a sheet weight of about 5-1000 gsm and a thickness of approximately 5-1000 microns, in some examples. The fibers may be continuous along the length of the layer or discrete, having many smaller lengths that overlap, and the size may be lightweight, such as 1-10 denier, or heavy weight in some applications, up to 50 denier or heavier. The height of the fibers should be high enough to allow the fibers to create a channel for fluids to flow between the fibers as the layers are brought together by force or under suction. That is, the height should be large enough to allow urine to flow between the layers without incurring a vacuum lock. In general, the flow director layer 5 provides for more oriented flow so as not to disperse fluid in all directions, but instead directs it toward the suction region. Therefore hydrophobic materials having fibers or channels oriented longitudinally are candidate materials.

The flow director layer 5 may be made of a thermoplastic polymer, a thermoset polymer, or combination thereof, or a natural fiber. Examples of suitable thermoplastics include but are not limited to: polyethylene, polypropylene, polyethylene terephthalate, polyamide, polyvinyl chloride, polyester, polyether, polyurethane, polytetrafluoroethylene, block-copolymer elastomers, polyamide. Examples of suitable thermosets/rubbers include but are not limited to: butyl, chloroprene, epichlorohydrin, ethylene/acrylic, ethylene-propylene, fluorocarbon, fluorosilicone, silicone rubber, natural rubber, nitrile, hydrogenated nitrile, perfluoroelastomer, polyacrylate, polysulfide, styrene butadiene. Examples of suitable natural fibers include but are not limited to: linen, silk, and wool.

In some examples, the fibers 87 are hydrophobic either because the underlying fiber material is inherently hydrophobic, or it is treated with a hydrophobic compound making it non-wicking. Hydrophobicity tends to prevent attraction (wetting or wicking) of the urine to the surface. However, depending on the nature, size, and orientation of the fibers, a neutral or hydrophilic material may be similarly functional. Additionally or alternatively, the fibers may be constructed of a nonwoven material.

Figure 8A:
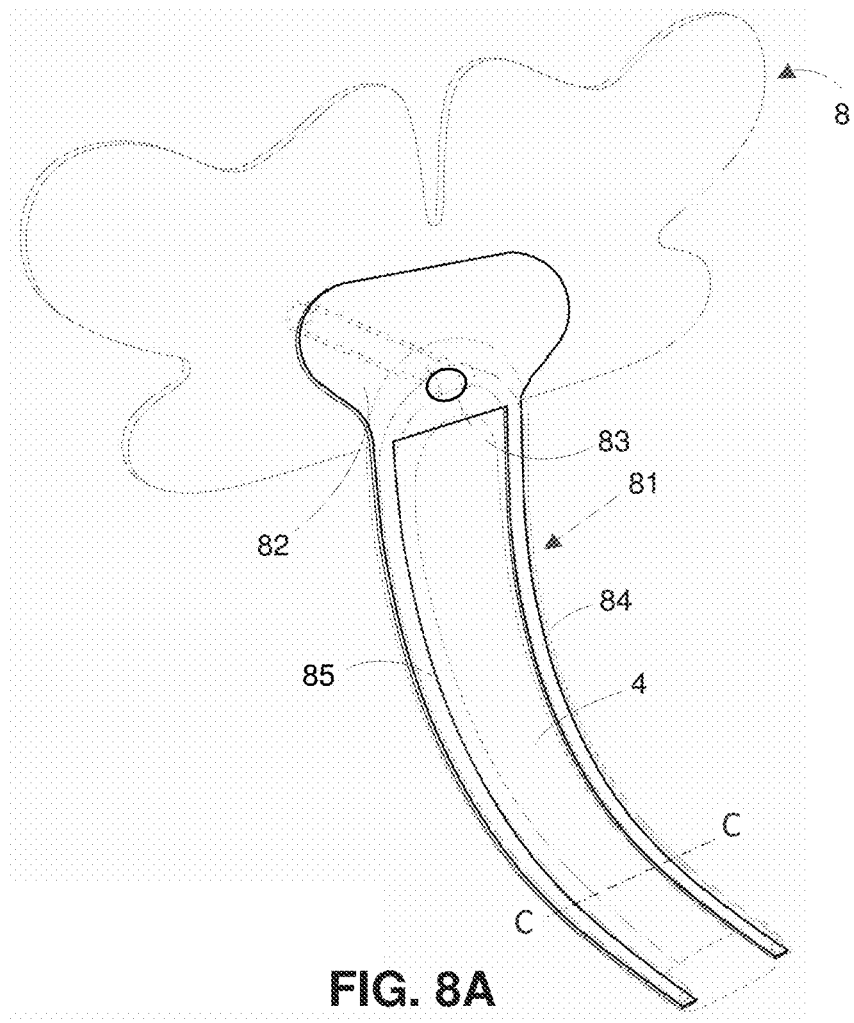
FIGS. 8A and 8B illustrate a perspective view and a cross-sectional view of an example embodiment of a frame of a urine removal device.
Figure 8B:
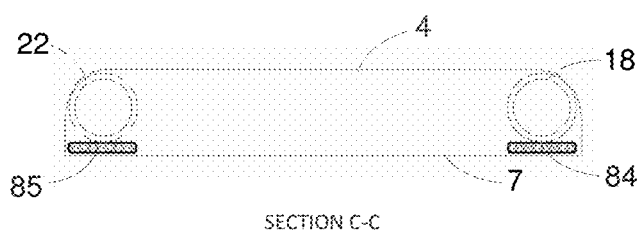

One skilled in the art would recognize that there are many frame configurations that provide different levels of support/ stiffness for a urine removal device. Various configurations are illustrated in FIGS. 8A-19 by way of nonlimiting example. FIGS. 8A-8B illustrate a frame 81 having a branch 84 and 85 comprised of a single layer. Similar to the other frames disclosed herein, the frame 81 may have an aperture 83 for passage of a suction tube, and a base 82 for connecting to an adhesive patch 8 and optionally to any of the layers of the device. A cross-sectional view is shown in FIG. 8B, which illustrates the location of the branches 84 and 85 adjacent to the conduits 18 and 22, respectively. In this example, the branches 84 and 85 are located inside of the outer layer 7, but they may reside in other locations, such as outside of all of the layers, or on top of the conduits 18 and 22, for example. The frame 81 may be made of a polymer or a metal or other suitable material by any of those methods known by one skilled in the art.

Figure 9:
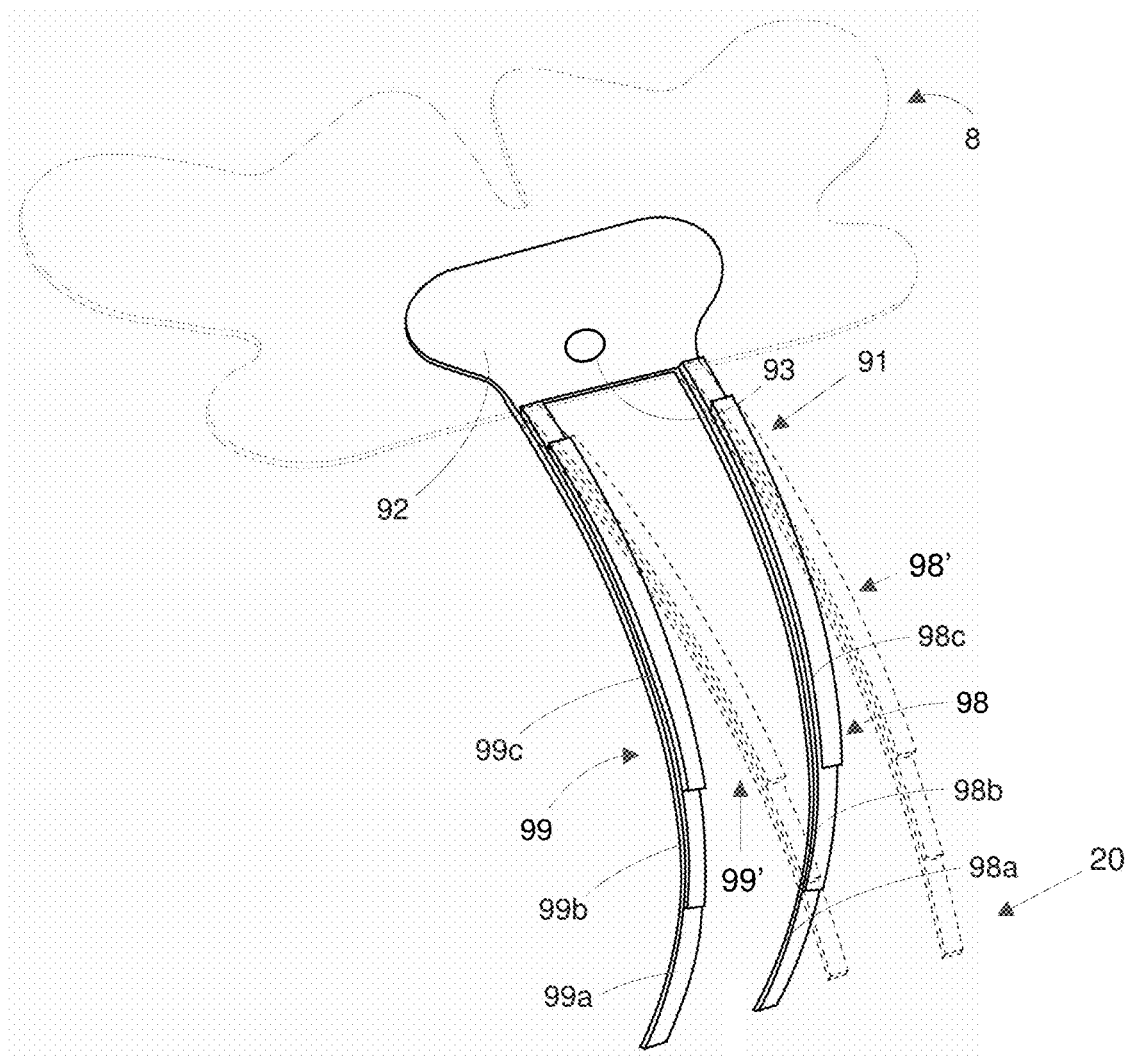
FIG. 9 illustrates a perspective view of an example embodiment of a frame of a urine removal device.

Another example of a frame is illustrated in FIG. 9 as shown in a view from the bottom of the device, that is, toward the outer layer to illustrate the structure of the frame. The frame 91 comprises an aperture 93 and a base 92, like previously disclosed examples, but differs in that it has multiple layers along each branch, each layer having a different length similar to a leaf spring arrangement. The first branch 98 has an inner beam 98*a*, a longer middle beam 98*b*, and an outer beam 98*c* that is longer than the middle beam 98*b*. Similarly, the second branch 99 has an inner beam 99*a*, a longer middle beam 99*b*, and an outer beam 99*c* that is longer than the middle beam 99*b*. This arrangement allows the designer to tune the stiffness along the frame, such that, for example, the decreasing thickness provides a decreasing bending stiffness along the branches 98 and 99 from the base 92 to the distal end 20. The frame may be made of a polymer or a metal or other suitable material by any of those methods known by one skilled in the art. For example, the frame may be molded in one piece with a stepped configuration as shown in FIG. 9, or it may be molded in a tapered configuration with a gradually tapering shape that narrows in a linear or nonlinear fashion from the base 92 to the distal end 20. Alternatively, the layers (e.g., beams 98*a*, 98*b*, and 98*c*) may be separate members that are joined by bonding, heat staking (thermal bonding), radio frequency or ultrasonic welding for example. In other examples, the frame may be made of a metal such as high-carbon steel, oil-tempered low-carbon, chrome silicon, chrome vanadium, and stainless steel, stainless steel, titanium, copper, aluminum, or various alloys like beryllium copper alloy, phosphor bronze, etc. that provides the required flexibility. The overall base and inner beam 98a may be made of a single stamped or laser cut metal form while the other metal layers (e.g., layers 98b, and 98c) may be joined to the inner beam 98a by bonding, laser welding, spot welding, or any other method for joining or fastening sheets of metal. In other examples, the frame may be made of a combination of two or more materials including metals, polymers or natural materials such as wood, bamboo, cellulose, etc.

A frame, being the stiffest member, generally dictates the overall shape of the urine removal device. The shape of the frames disclosed herein are generally curved to fit between the legs in the region extending from the lower abdomen to the perineum in the groin area. In order to effectively seat in this area, a frame may be shaped in way that preloads the device against the user's (patient's) skin in this region to aid it staying seated against the anatomy. A frame may be shaped such that it is pre-set more than it will be when placed in the anatomy such that it is preloaded when fit onto the anatomy, and any of the frames disclosed herein may have this feature. For example, the dashed lines in FIG. 9 illustrate the shape of the frame 98' when it is in place on the body while the solid lines represent the shape of the frame 91 as manufactured. The base 92 serves as a datum because it is mounted to the suprapubic area via the adhesive patch 8—this region tends to react any forces applied along the branches 98 and 99 of the frame, much like a cantilever beam, although there will be some compliance of the skin where the adhesive attaches. The amount of preload that the device exerts on the anatomy is related to the difference in deflection between the unloaded state and the loaded state (dashed) and the stiffness of the branches. The first branch 98 deflects from 98 to 98' as shown, while the second branch 99 deflects from 99 to 99' as shown. Thus, the designer can tune the amount of preload against the body by the shape and stiffness of the frame 91. Furthermore, in some examples, the frame may be malleable, such that the frame can be deformed while it is placed against the anatomy resulting in a shape that conforms to the anatomy.

Figure 10A:
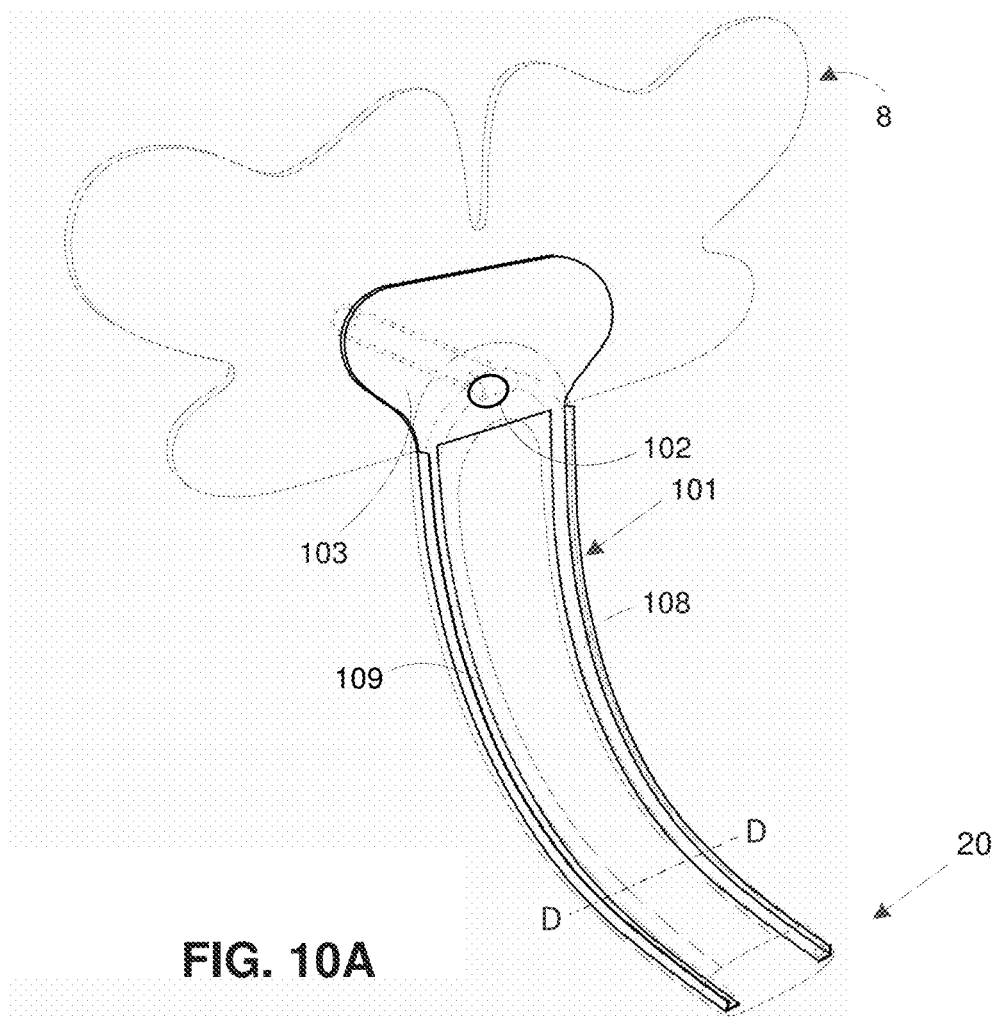
FIGS. 10A and 10B illustrate a perspective view and a cross-sectional view of an example embodiment of a frame of a urine removal device.
Figure 10B:
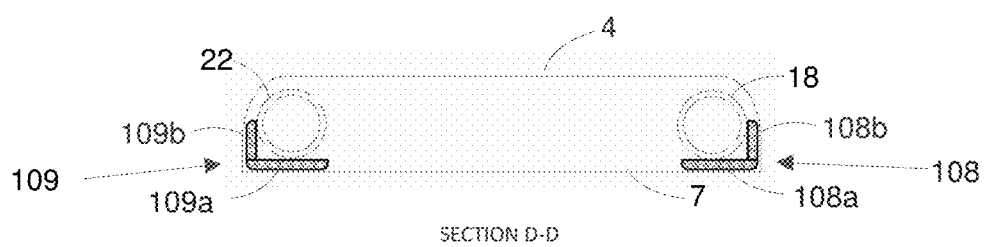

FIGS. 10A-10B illustrate a frame 101 having branches 108 and 109 comprised of a single layer having an outboard wall. Similar to the other frames disclosed herein, the frame 101 may have an aperture 102 for passage of a suction tube, and a base 103 for connecting to an adhesive patch 8 and optionally to any of the wetting layers of the device. A cross-sectional view is shown in FIG. 10B, which illustrates the orientation of the branches 108 and 109 adjacent to the conduits 18 and 22, respectively. The branches 108 and 109 each have a vertical outer wall 108b and 109b, respectively, forming an "L" section with the outer walls 108a and 109a, respectively. This "L" section adds stiffness to the frame 101 particularly in the lateral direction. In this example, the branches 108 and 109 are located inside of the outer layer 7, but they may reside in other locations, such as outside of all of the layers, or on top of the conduits 18 and 22, for example.

Figure 11A:
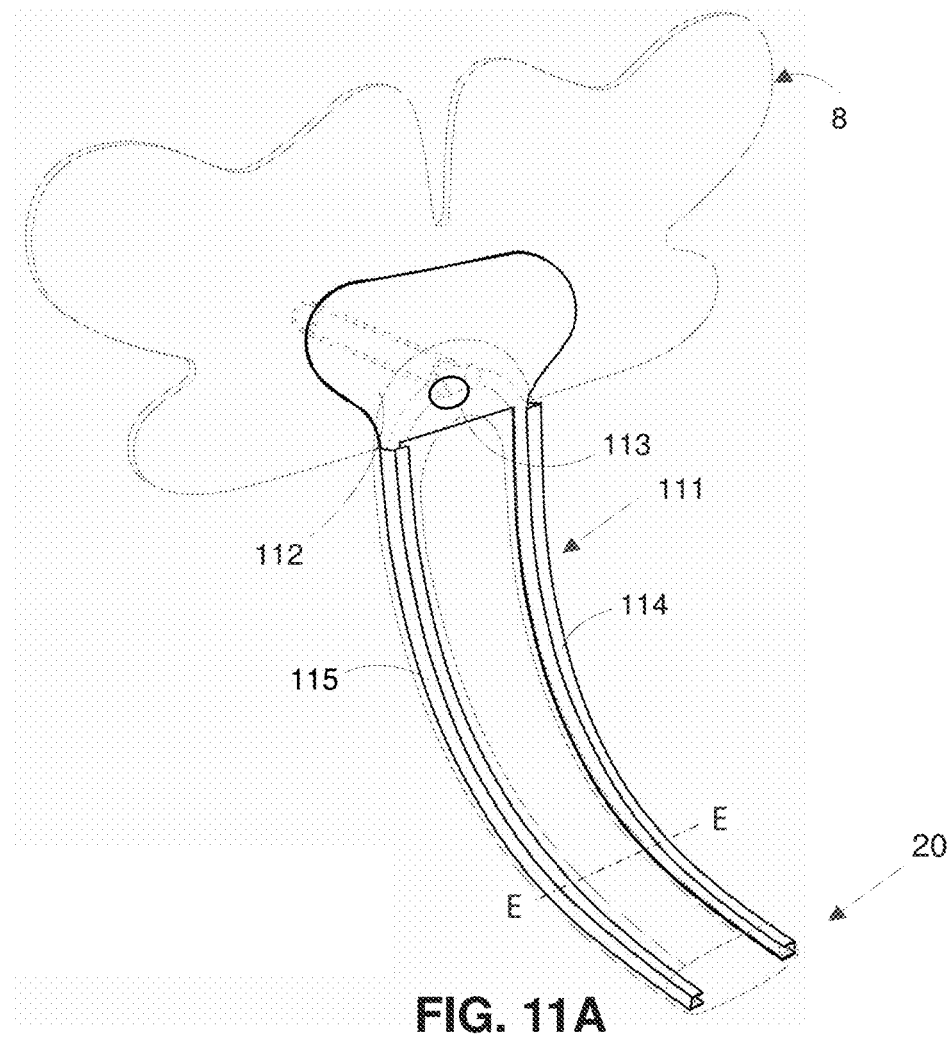
FIGS. 11A and 11B illustrate a perspective view and a cross-sectional view of an example embodiment of a frame of a urine removal device.
Figure 11B:
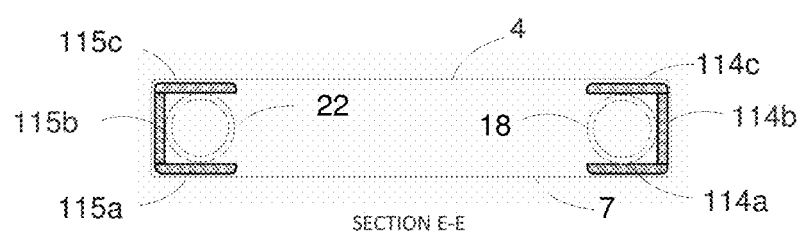

FIGS. 11A-11B illustrate a frame 111 having branches 114 and 115 comprised of a single layer having an outboard wall and an inner wall. Similar to the other frames disclosed herein, the frame 111 may have an aperture 113 for passage of a suction tube, and a base 112 for connecting to an adhesive patch 8 and optionally to any of the wetting layers of the device. A cross-sectional view is shown in FIG. 11B, which illustrates the orientation of the branches 114 and 115 adjacent to the conduits 18 and 22, respectively. The branches 114 and 115 each have a horizontal wall 114a and 115a, and a vertical outer wall 114b and 115b, respectively, similar to the example shown in FIG. 10B. However, the present example also has inner walls 114c and 115c on each branch 114 and 115 respectively, forming a "C" section. This "C" section adds stiffness to the frame 111 both in the lateral and vertical directions as well as protecting the conduits 18 and 22 from external forces, potentially allowing them to be made of thinner walled, weaker sections. The "C" section also serves to catch urine when the device tilted, acting as a gutter to catch excess urine from flowing over the side of the device. As with previous examples, in this example, the branches 114 and 115 are located inside of the outer layer 7, but they may reside in other locations, such as outside of all of the layers, or on top of the conduits 18 and 22, for example.

The examples shown in FIGS. 8A-8B, and 10A-11B may be made of any suitable polymer, metal, or natural material. Examples include, high-carbon steel, oil-tempered low-carbon, chrome silicon, chrome vanadium, and stainless steel, stainless steel, titanium, copper, aluminum, or various alloys like beryllium copper alloy, phosphor bronze, etc. that provides the required flexibility. The overall base and inner beam may be made of a single stamped, molded, die cut, or laser cut form. Polymeric frame material examples include nylon, polyethylene, polypropylene, ABS, or other suitable polymers. Alternatively, natural materials such as wood, bamboo, cellulose, may be used.

Figure 12:
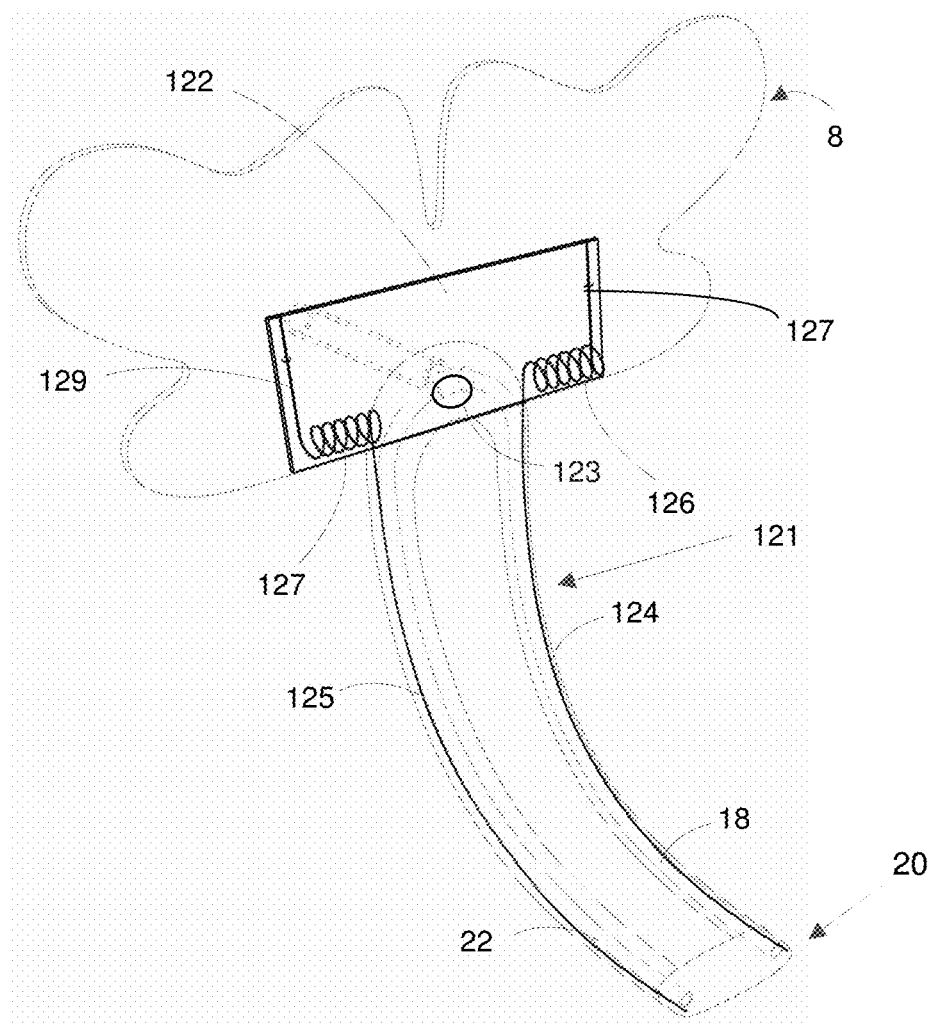
FIG. 12 illustrates a perspective view of an example embodiment of a frame of a urine removal device.

FIG. 12 illustrates a frame having torsional springs that provide some of the elasticity. A first torsional spring 126 has a first leg 127 that is mounted to the base 122 of the frame 121. The second leg 124 of the first torsional spring 126 forms an arcuate branch along the first conduit 18. Similarly, a second torsional spring 127 has a first leg 129 that is mounted to the base 122 of the frame 121. The second leg 125 of the second torsional spring 127 forms an arcuate branch along the second conduit 22. Together, the second legs 124 and 125 of the torsion springs 126 and 127, respectively, provide the desired shape of the urine removal device and flexibility is achieved from the bending compliance of the legs 124 and 125 and the deflection of the torsion springs 126 and 127. Similar to the other frames disclosed herein, the frame 121 may have an aperture 123 for passage of a suction tube, and a base 122 for connecting to an adhesive patch 8 and optionally to any of the wetting layers of the device. Each spring may be made of a wireform that comprises a metal such as stainless steel, spring steel, or other metals or alloys suitable for springs. In some examples, the first spring and second spring may be fabricated as one single wireform that is connected along the base 122 or at the distal end 20 or both.

Figure 13:
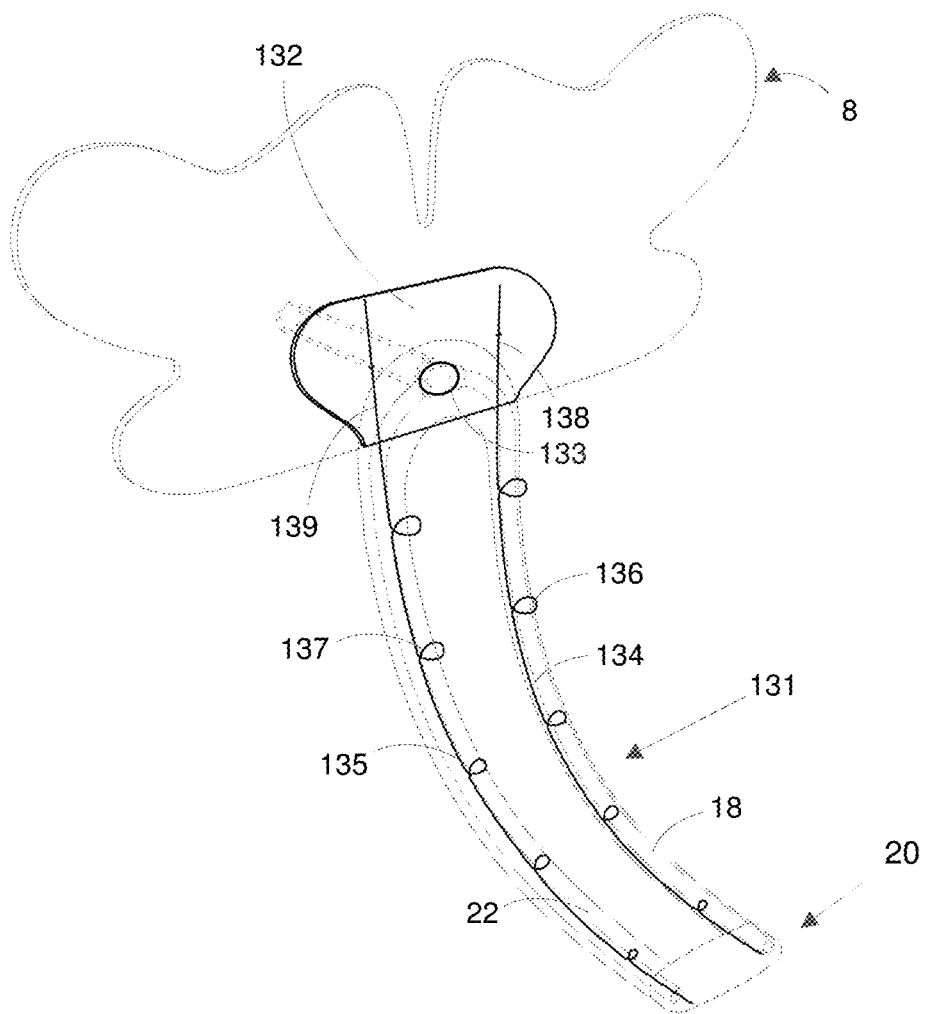
FIG. 13 illustrates a perspective view of an example embodiment of a frame of a urine removal device.

Now with reference to FIG. 13, which illustrates a frame 131 having wireform branches with periodic loops. A first branch 134 is mounted to a base 132 in an overlap section 138 which provides the cantilever base for the branch 134. The first branch 134 has periodic loops 136 running along its length (only one loop is labeled). The first branch 134, and hoops 136, reside adjacent to the first conduit 18 and the hoops 136 may become smaller towards the distal end 20. A second branch 135 also has hoops 137 arranged in a similar manner and an overlap section 139 which mounts to the base 132. Together, the branches and the hoops provide several design variables for tuning the stiffness of the branches including the wire gage, the hoop diameters, the number of hoops, and the spacing between the hoops. Similar to the other frames disclosed herein, the frame 131 may have an aperture 133 for passage of a suction tube, and a base 132 for connecting to an adhesive patch 8 and optionally to any of the wetting layers of the device. Each wireform may be made of a metal such as stainless steel, spring steel, or other metals or alloys suitable for springs. In some examples, the first spring and second spring may be fabricated as one single wireform that is connected along the base 132. The base 132 may be made of a polymer or a metal by any of those methods known by one skilled in the art. By way of nonlimiting example, the branches may be attached to a metal base by welding, brazing, or bonding and they may be attached to a polymeric base by bonding or being captured between layers. Alternatively, the branches 134 and 135 may connect at their proximal end 16 comprising one contiguous wireform, the base of such wireform attaches either to a base layer or directly to the adhesive patch 8.

Figure 14:
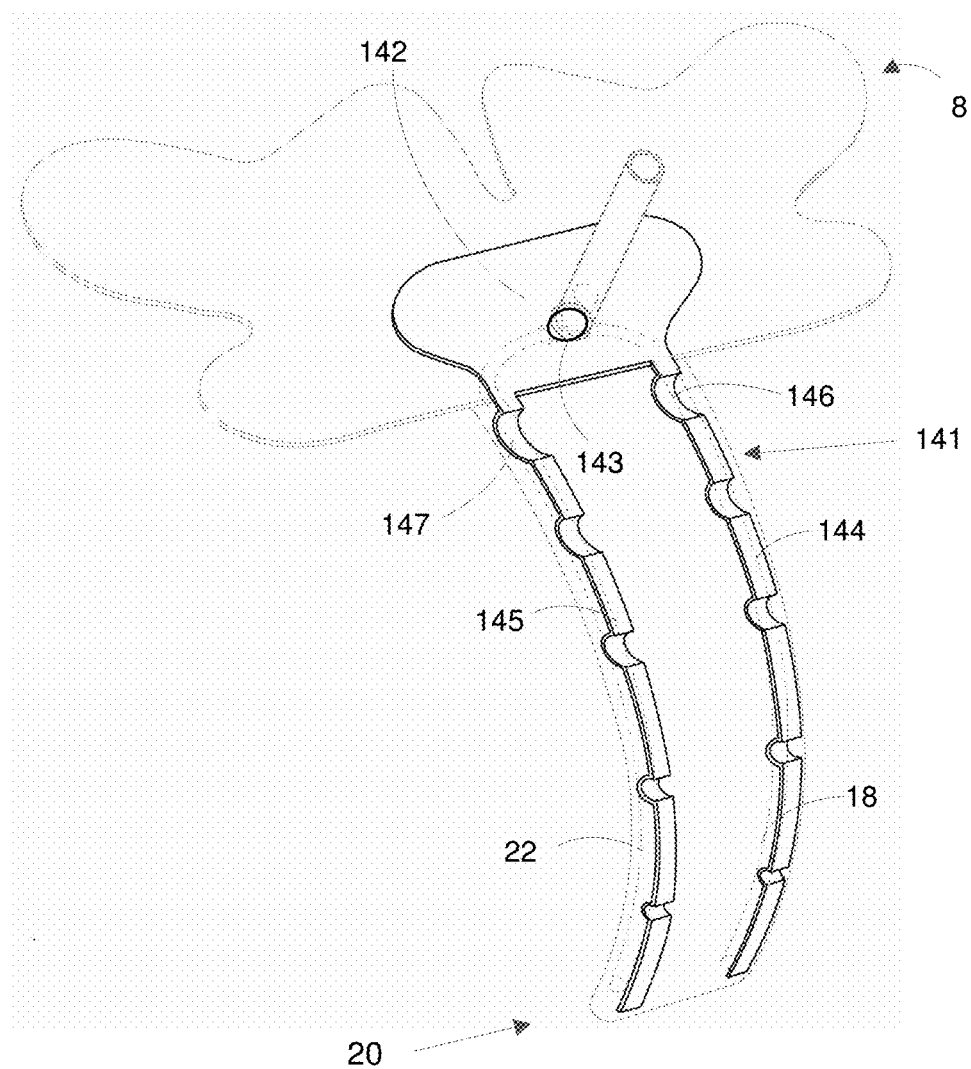
FIG. 14 illustrates a perspective view of an example embodiment of a frame of a urine removal device.
Figure 15:
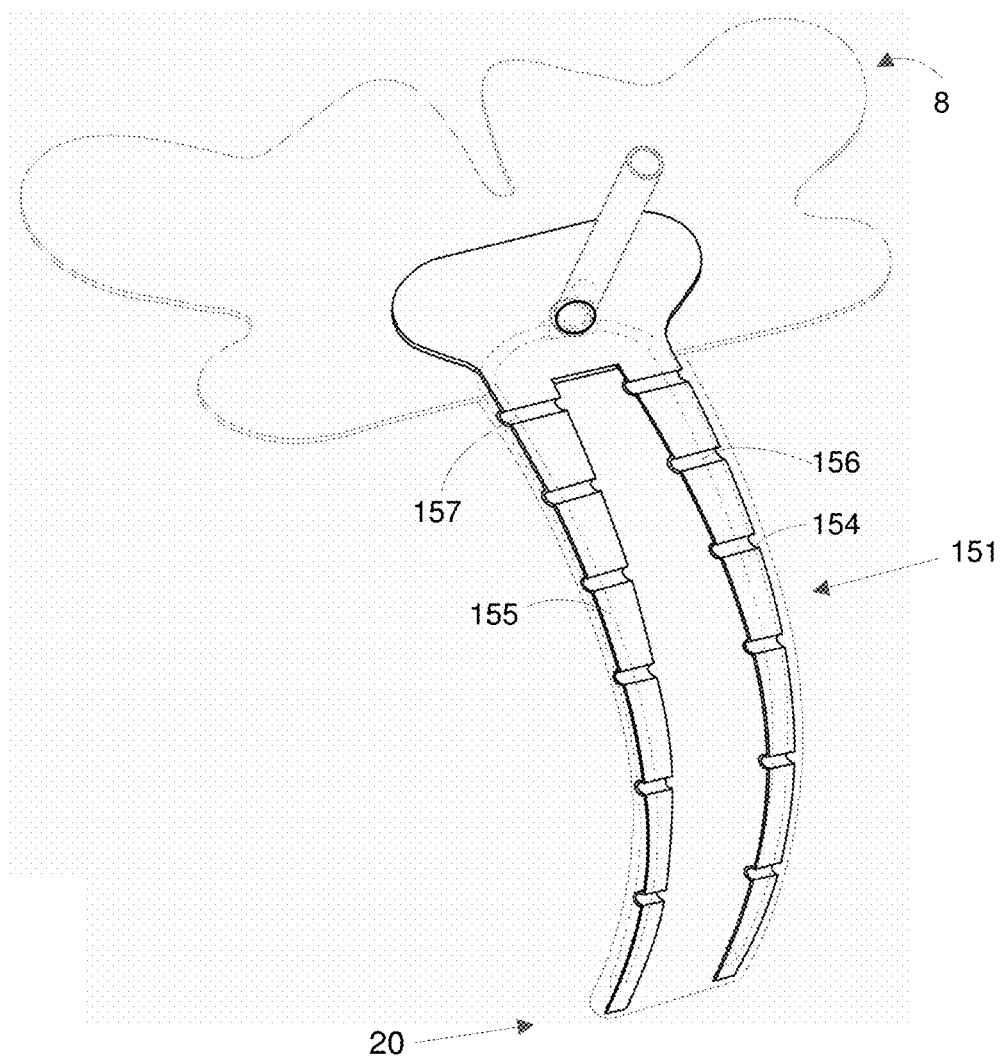
FIG. 15 illustrates a perspective view of an example embodiment of a frame of a urine removal device.
Figure 16:
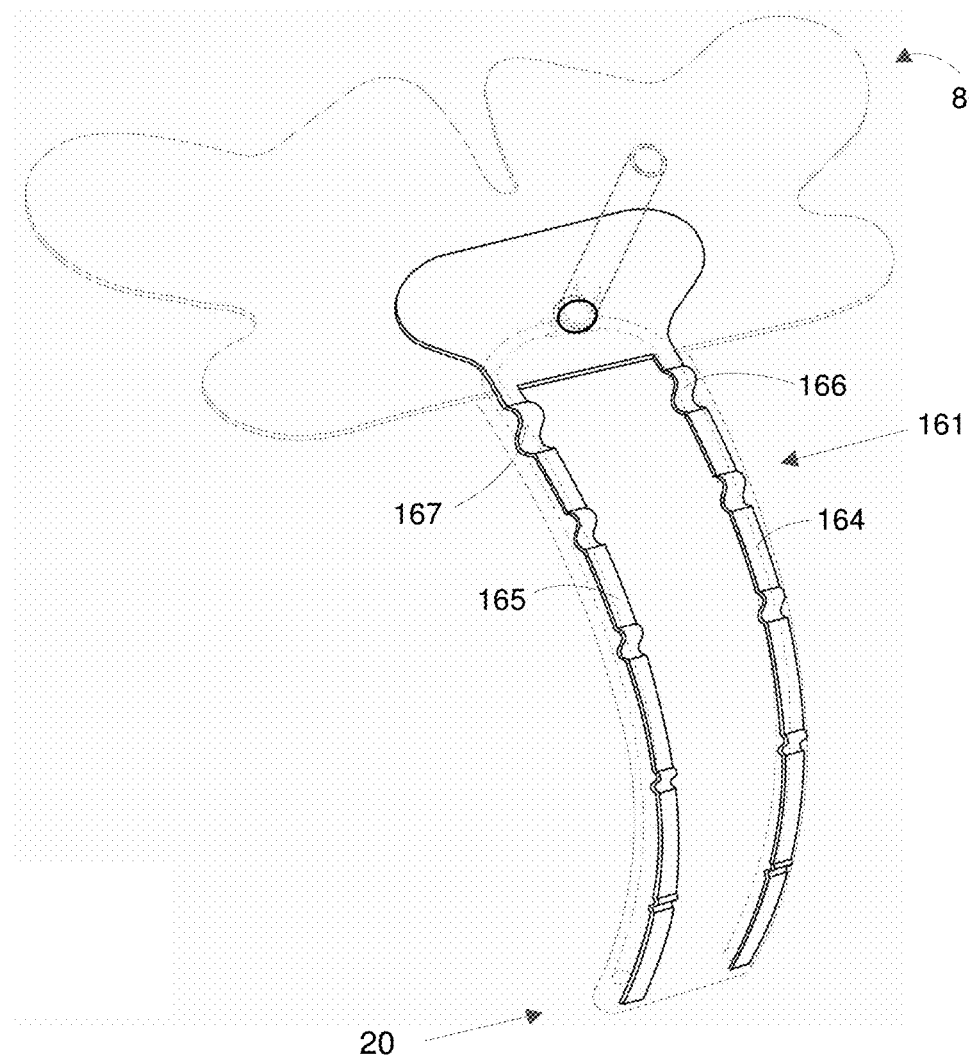
FIG. 16 illustrates a perspective view of an example embodiment of a frame of a urine removal device.

Frame examples with periodic reliefs are shown in FIGS. 14-16. For example, an example of a frame is illustrated in FIG. 14 and is shown in a view from the bottom of the device, that is toward the outer layer to illustrate the structure of the frame. The frame 141 comprises an aperture 143 and a base 142, and a pair of branches 144 and 145 with periodic reliefs 146 and 147 along the branches 144 and 145 respectively. FIG. 15 illustrates a similar example of a frame 151 having a pair of branches 154 and 155 with periodic reliefs 156 and 157 along the branches 154 and 155 respectively. The branches 154 and 155 taper toward the distal end 20 to provide more compliance. FIG. 16 illustrates yet another similar example of a frame 161 having a pair of branches 164 and 165 with periodic zig-zag or "S" shaped reliefs 166 and 167 along the branches 164 and 165 respectively. In frames 141, 151, and frame 161, the branches and reliefs provide additional design variables for tuning the stiffness of the branches, e.g., the shapes and sizes of the reliefs, the number of reliefs, and the spacing between the reliefs. The frames 141, 151, and 161 may be made of a polymer or a metal or a natural material or a combination by any methods known by one skilled in the art. For example, the frames may be molded in one piece with the reliefs as shown in FIGS. 14-16. Alternatively, the frames may be made of a metal and stamped in the configurations shown. That is, the overall base and branches may be made of a single stamped or laser cut metal form. Example materials include, high-carbon steel, oil-tempered low-carbon, chrome silicon, chrome vanadium, and stainless steel, stainless steel, titanium, copper, aluminum, or various alloys like beryllium copper alloy, phosphor bronze, etc. that provides the required flexibility. The overall base and inner beam may be made of a single stamped, molded, die cut, or laser cut form. Polymeric frame material examples include nylon, polyethylene, polyprphelene, ABS, or other suitable polymers. Alternatively, natural materials such as wood, bamboo, cellulose, may be used.

Figure 17:
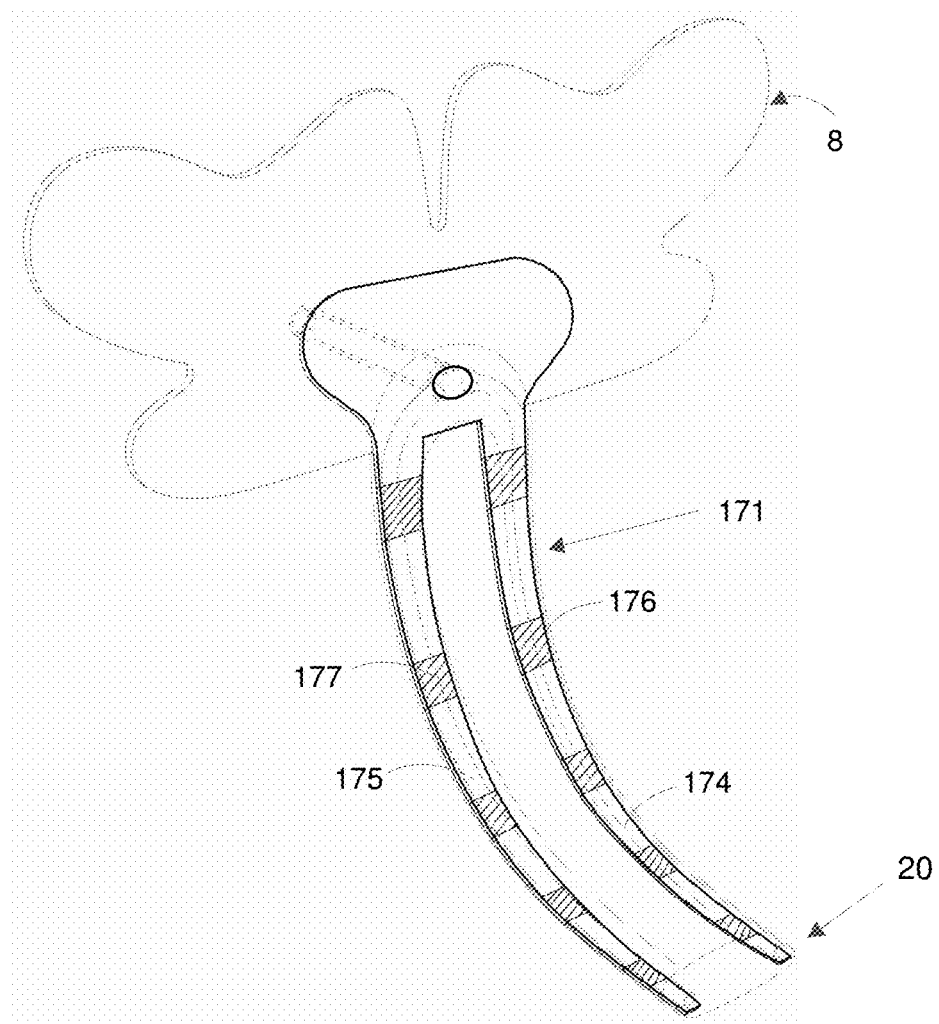
FIG. 17 illustrates a perspective view of an example embodiment of a frame of a urine removal device.

FIG. 17 illustrates a frame 171 having branches with periodic material changes along the length. The branches 174 and 175 have periodic segments 176 and 177 respectively running along the length (only one patch is labeled). The segments 176 and 177 represent sections with different material properties. For example, the segments may be made of a more compliant material (lower young's modulus). In general, each of the segments need not be of the same material, thickness, or stiffness. The segments provide several design variables for tuning the stiffness of the branches, e.g., the material, thickness, and length of the segments. Similar to the other frames disclosed herein, the frame 132 may have an aperture 133 for passage of a suction tube, and a base 132 for connecting to an adhesive patch 8 and optionally to any of the wetting layers of the device. In some examples, the segments may be attached to an underlying stamped or molded frame to provide zones with additional stiffness. In other examples, the segments may be bonded to sections of the branches, forming bridges between sections of the branch by way of mechanical (e.g., fasters, joints, rivets, etc.), chemical (e.g. adhesives, solvents, etc.) or physical (e.g., welding, co-molding, over-molding, etc.).

Figure 18:
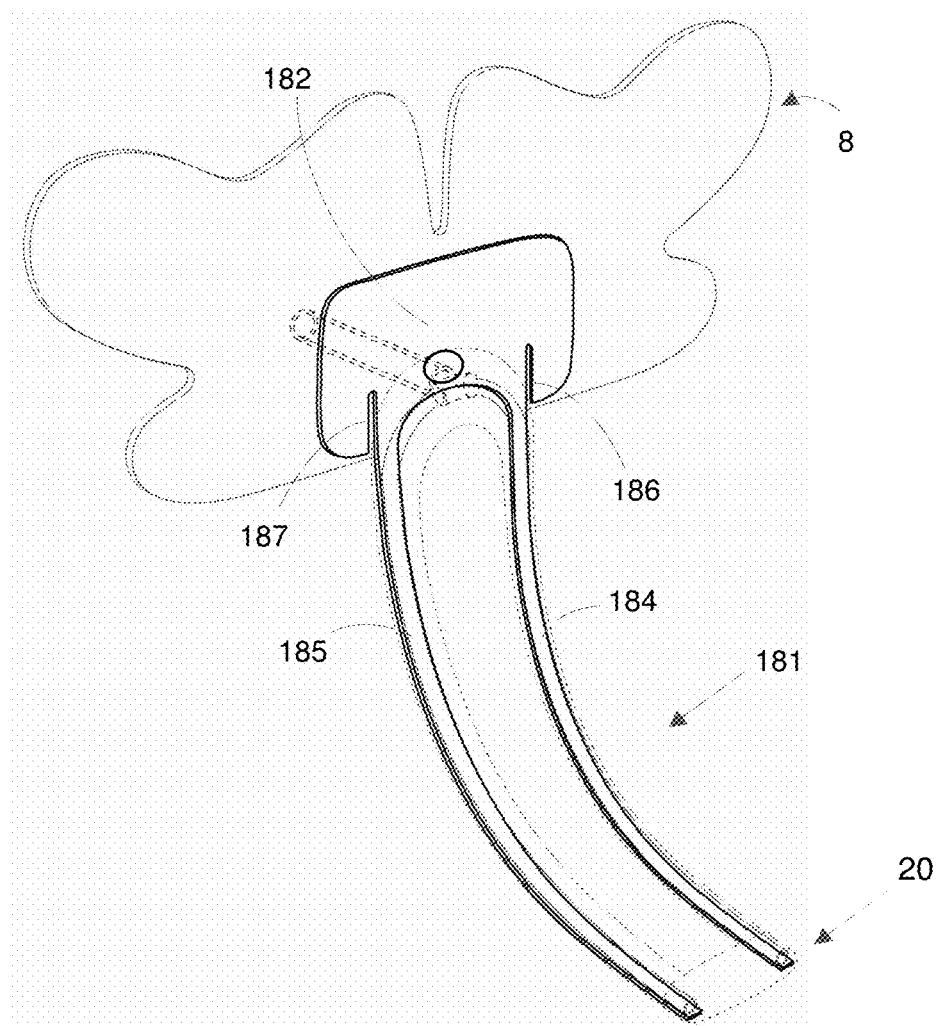
FIG. 18 illustrates a perspective view of an example embodiment of a frame of a urine removal device.
Figure 19:
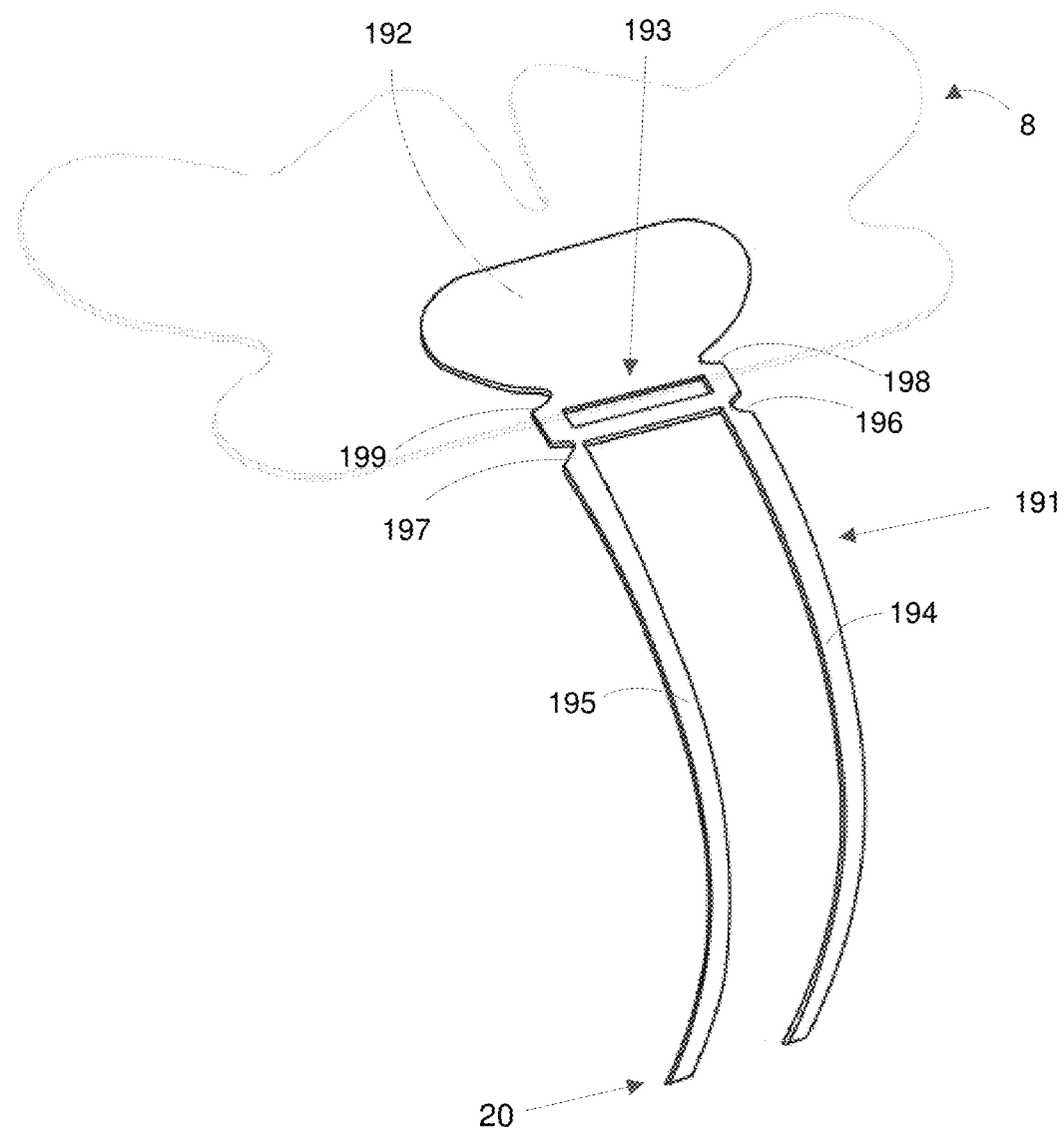
FIG. 19 illustrates a perspective view of an example embodiment of a frame of a urine removal device.

Some frame examples may have a strain relief at the junction of the base where the branches emanate, examples of which are illustrated in FIGS. 18 and 19. FIG. 18 shows a frame 181 having reliefs 186 and 187 extending parallel with each branch 184 and 185, respectively, up into the base 182. The reliefs 187 and 186 may provide added flexibility and reduced stresses at the joint where the branches 184 and 185 meet the base 182 while providing another design variable to tune the flexibility of the branches. As the reliefs are at the root of the beam-like branches, geometrical changes in this region can have a significant effect on the stiffness of the branches. The example shown in FIG. 19 illustrates a frame 191 having a pair of notches near the base of each branch. The first branch 194 has a first notch 196 and a second notch 198 proximal to the first notch 196 while the second branch 195 has a symmetrically placed pair of notches 197 and 199. In between the notches a cutout 193 is provided across the base 192. The cutout combined with the notches provide additional design variables to tune the stiffness of the frame as well as to adjust the stress distribution of the frame at the region where the branches meet the base. One skilled in the art would recognize that there are many combinations of cutouts, reliefs, and notches that may be incorporated to a frame, including the frame examples disclosed herein, to achieve a desired stiffness and stress distribution and such examples are within the scope of this disclosure.

Example materials for frames 171, 181, and 191 include, high-carbon steel, oil-tempered low-carbon, chrome silicon, chrome vanadium, and stainless steel, stainless steel, titanium, copper, aluminum, or various alloys like beryllium copper alloy, phosphor bronze, etc. that provides the required flexibility. The overall base and inner beam may be made of a single stamped, molded, die cut, or laser cut form. Polymeric frame material examples include nylon, polyethylene, polyprphelene, ABS, or other suitable polymers. Alternatively, natural materials such as wood, bamboo, cellulose, may be used.

Figure 20:
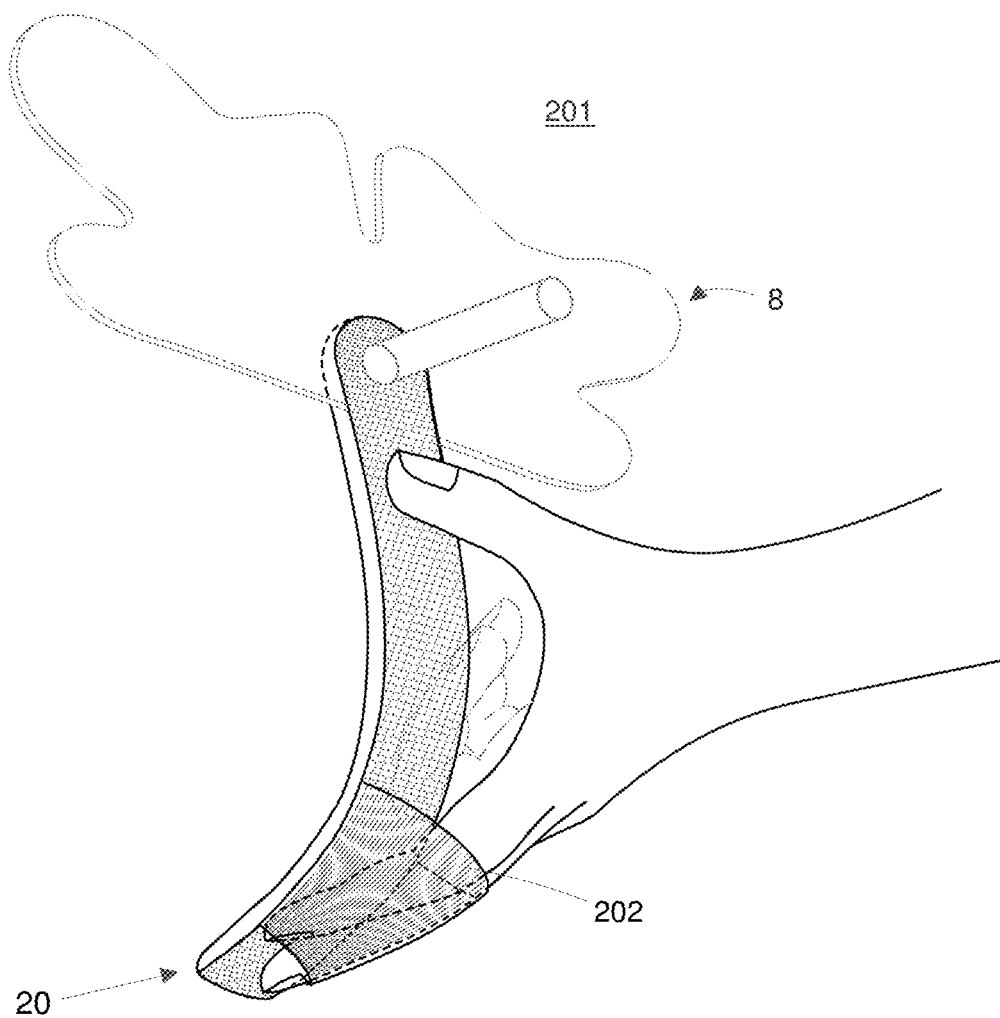
FIG. 20 illustrates an example embodiment of a frame of a urine removal device having a finger strap for locating the device.

When a urine removal device is placed on a user by a practitioner (or the user) it is placed between the legs and onto the vaginal region with some pressure to seat it against the body. When seating the device, the user may reposition the device by pulling it back or rotating it. In order to aid in controlling the positioning of the device, a grasping feature may be attached to the device. FIG. 20 illustrates an example of a grasping feature in the form of a finger strap integrated onto simplified urine removal device for purposes of illustration, although the grasping device may be integrated with any urine removal device. The device 201 has a finger strap 202 attached near the distal end to encircle one or more of the fingers of the hand installing the device 201. In use, the adhesive patch 8 may be attached to the body first, and then the distal end 20 of the device 201 is articulated into place, or the adhesive patch 8 may be attached after the device 201 is placed in the vaginal region. Alternatively, the adhesive patch 8 may be attached to the body while the device 201 is placed in the vaginal region.

Figure 21:
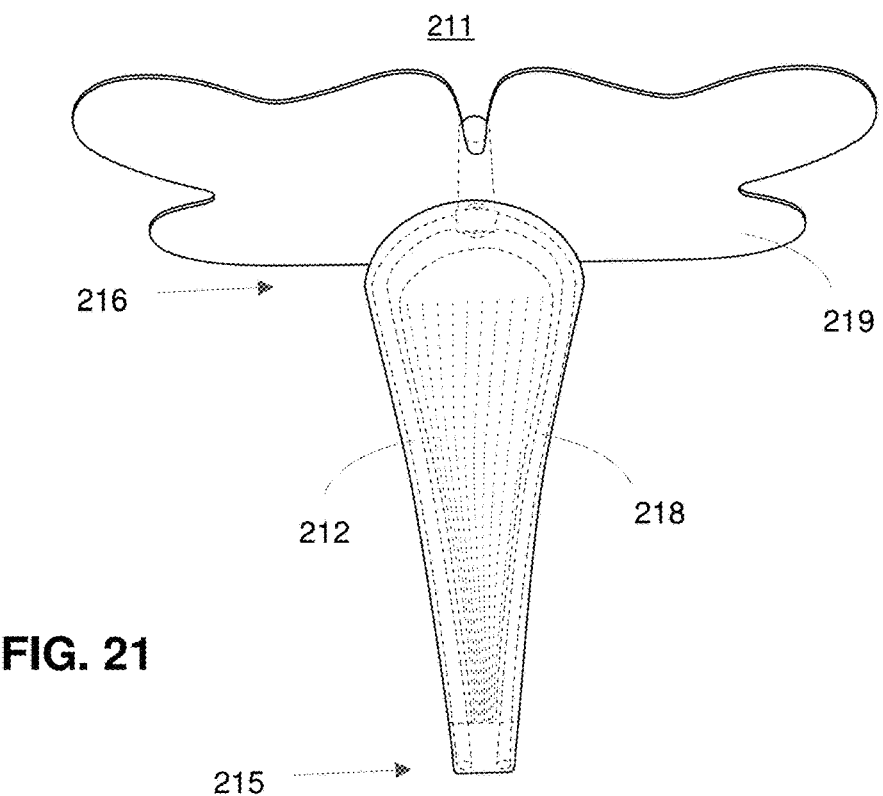
FIG. 21 illustrates another embodiment of a urine removal device.
Figure 22:
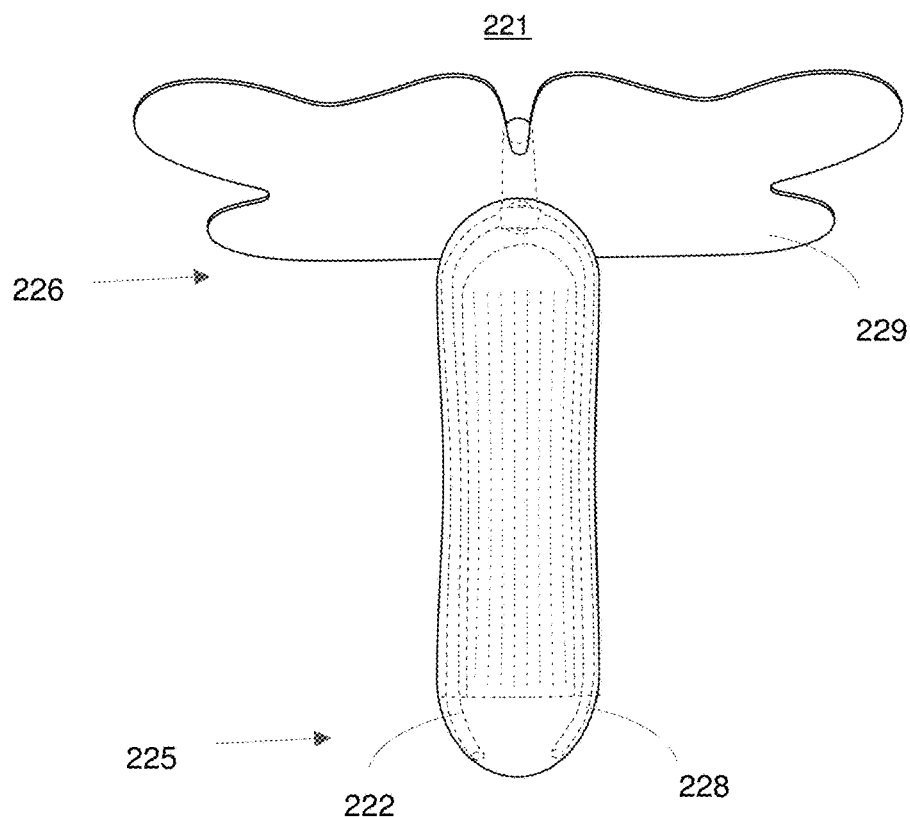
FIG. 22 illustrates another embodiment of a urine removal device.

Urine removal devices may have different overall shapes to conform to the anatomy to aid in catching urine and to offer a comfortable feel to the user. FIGS. 21 and 22 illustrate two additional examples having different overall shapes. The urine removal device 211 shown in FIG. 21 has a tapered shape that is narrower at the distal end 215 where the conduits 218 and 212 terminate than at the proximal end 216 near the adhesive patch 219. The urine removal device 221 shown in FIG. 22 has a linear shape with rounded ends at both the distal end 225 and proximal end 226 near the adhesive patch 229. In some examples, the conduits 228 and 222 may conform to the end of the device as shown; i.e., the conduits 228 and 222 at least partially follow the end curvature. In some illustrations shown herein, such as in examples shown in FIGS. 21 and 22, some elements and details are not shown, shown lightly, or not numbered to highlight the features being described, but it will be understood that other elements, such as a suction conduit or connector, may optionally be included in these examples.

The action of air passing through the layers is integral to the function of the system with respect to the removal of liquid and remnant moisture from the layers comprising the device. More specifically, the system may be arranged such that the air flow through the layers assists transferring urine out of the device.

One function of vacuum is to drain "pooling volumes" of urine received by the device more quickly into the conduit system; this reduces the amount of time that the weight of the urine inside the device can act to pull the device downward via gravity. During use, the adhesive patch is coupled with the body on one side and attached to the layered section on the other side. Any weight acting on the adhesive increases stress on the coupling between the adhesive patch and the body, subsequently increasing the risk of dislodgement of the system from its intended location. Furthermore, excess fluid in the device may lead to leakage and discomfort for the user. Transfer of fluid into the conduit system and out of the device reduces these undesirable effects.

Effective vacuum also removes any remnant moisture from the layer section. Pressure and concomitant air flow ultimately cause the removal of remnant liquid and moisture from the layer section into the conduit system. This occurs via two independent mechanisms.

The first mechanism is physical, where negative pressure and the action of air moving across the inside surface of the device layers pushes smaller urine droplets that have clung to the surface towards the conduit system. This mechanism is effective when air is pulled through the device via the conduit system and flows over layers which may have flow directors. The pressure exerted by the air flow on the droplets to create a force that is greater than the attractive forces between the liquid and the surface of the layer, which acts to hold the droplets to the surface. As the size of the water droplet decreases, the cross-section area upon which the air flow has to act decreases, which in turn decreases the exertion force of the air. There will be a balance of forces that eventually results in some small droplets and remnant moisture unable to be moved into the conduit system, which is where the second mechanism is important.

The second mechanism is physical, where the air moving across the inside surface of the device wall causes small water droplets and remnant moisture to evaporate and be removed along with the air itself. Evaporation is dependent on many variables; however with respect to variables such as volumetric air flow rate, surface area and air velocity are relevant. All of these variables are proportional to the rate of evaporation. Furthermore, in examples having flow directors, to increase the removal of moisture via this mechanism, the size and orientation of the flow directors with respect to the conduit system may be balanced to adequately expose the urine droplets to the air velocity across different areas within the enclosed space.

Figure 23A:
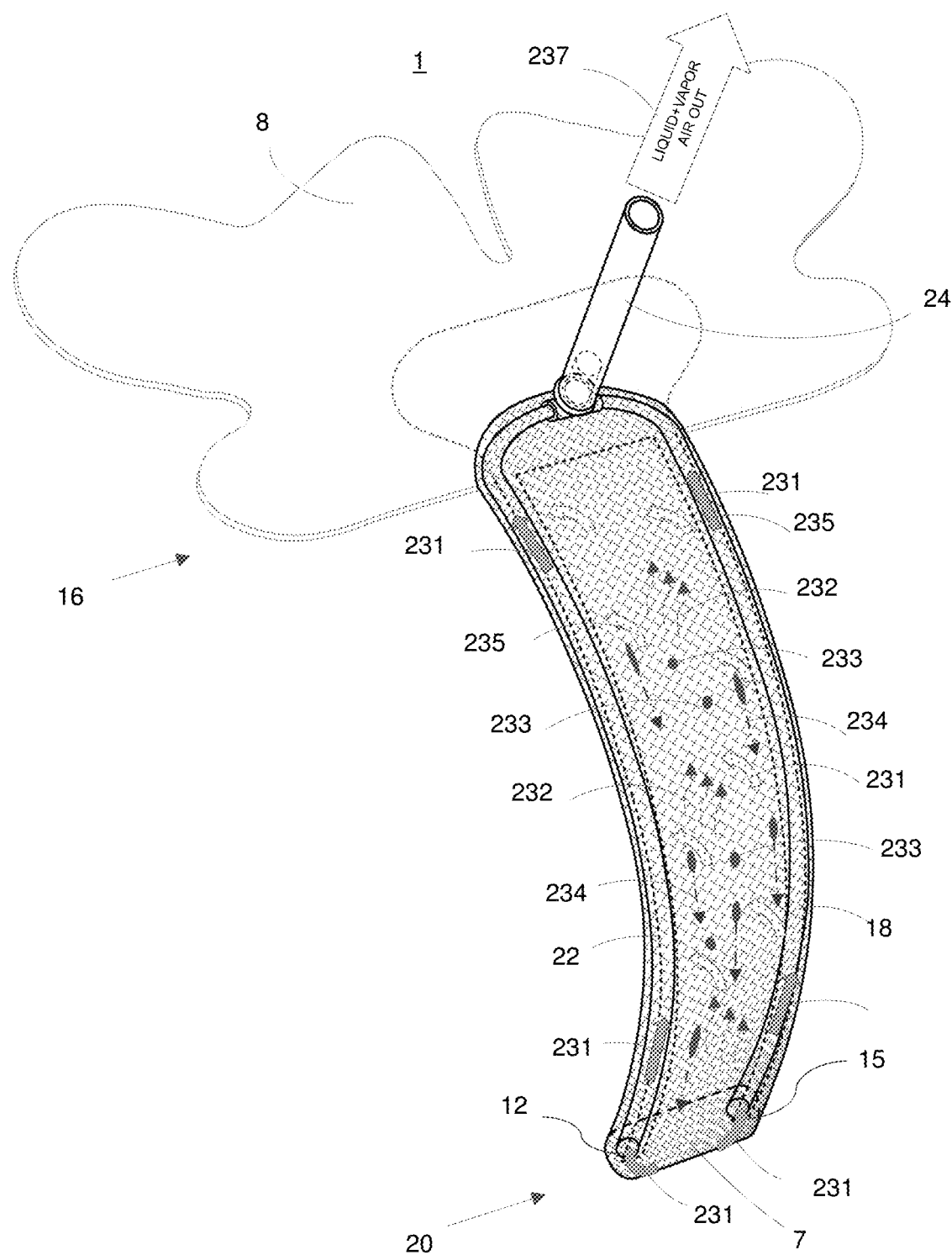
FIG. 23A illustrates the air flow and urine flow paths of a urine removal device according to an example embodiment.
Figure 23B:
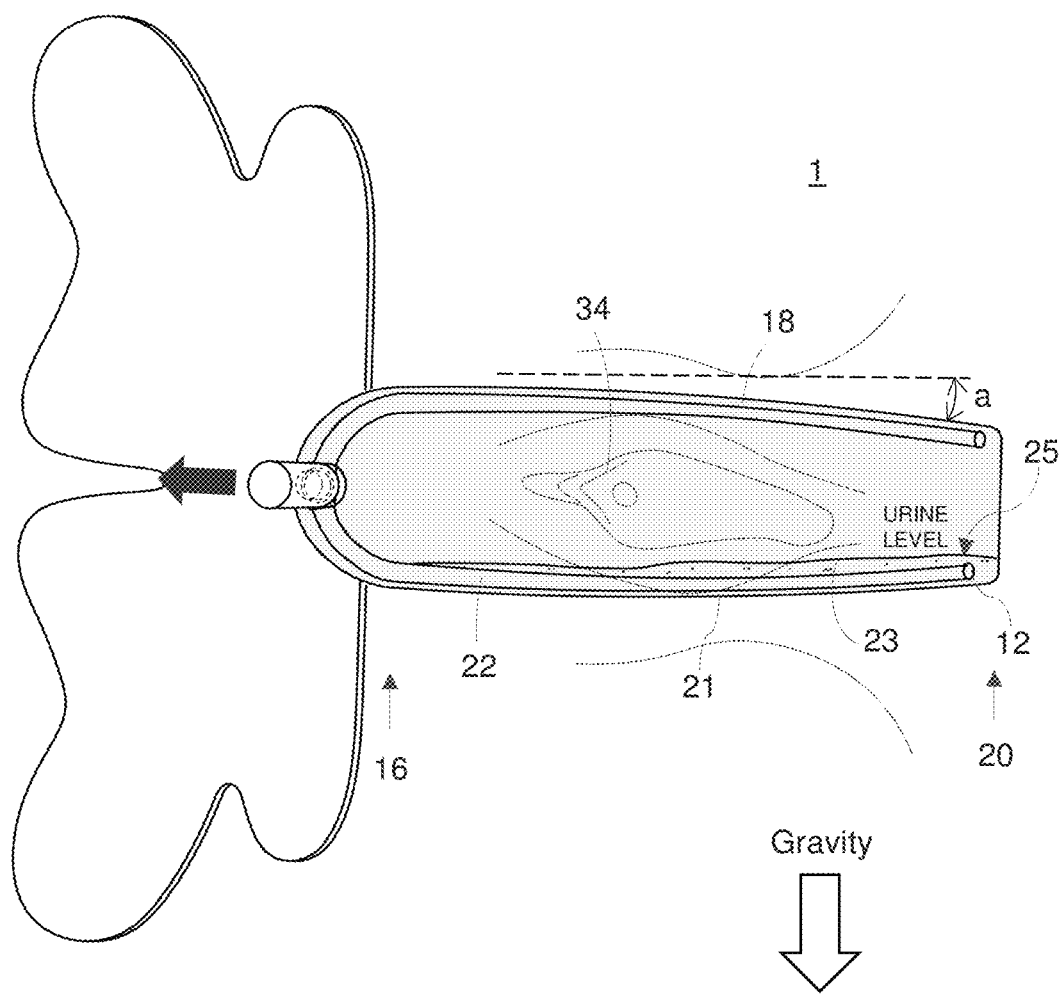
FIG. 23B illustrates a urine removal device oriented on a side showing urine temporarily pooling to one side of the device according to an example embodiment.

FIGS. 23A-23B show the urine removal device 1, previously described herein, in three different scenarios of use to illustrate the flow of urine, air, and moisture. Now with reference to FIG. 23A, which shows bottom perspective view of a device 1 in an arrangement that is otherwise the same as that in FIG. 1A, except that urine is present in the device 1. The dampness is a result of urine in or on the device 1 and/or sweat from the patient. Arrows 235 (unshaded) depict air flowing in through a semi-permeable layer, such as the outer layer 7. Next, the air is entrained into the device 1 as it flows from the proximal end 16 toward the distal end 20 of the device 1. In doing so, the air flows across the damp surfaces and through the damp air resulting in evaporation as depicted by arrows 232; the evaporation is enhanced by the forced convection of the air flowing through the device 1. Fluid droplets 233 are also pulled toward the distal end 20 as indicated by arrows 234. Near the distal end 20, the air and urine vapor are pulled in through the first conduit 18 and the second conduit 22 through the fluid inlets 15 and 12 respectively, as indicated by arrows 231 (shaded) where the mixture travels through the conduits 18 and 22 as indicated by arrows 231. Finally, the air/urine vapor mixture is drawn out through the suction source tube 24 as indicated by arrow 237. Thus, the air and urine vapor flow from the proximal end 16 to the distal end 20 of the device 1 is driven by the conduits 18 and 22 through their inlet at the distal end of the device 1.

This flow conduit arrangement tends to pull the urine away from the vagina, resulting in a more comfortable experience for the patient because the urine does not pool or otherwise reside around the body for an excessive amount of time. Additionally, as a result of the airflow within device 1, the air/microclimate within and on the device 1 is quickly dehumidified, and as a consequence the discomfort felt by the patient is minimized.

Furthermore, if flow directors and other materials inside of the device are made of nonabsorbent materials, drying may be further accelerated, resulting in a lightweight system with little or no accumulated urine inside. For example, if one or more layers comprise a nonwoven fiber surface made of a material that is nonabsorbent, liquids will tend not to absorb or adhere to the layer making the liquids easily propelled by the air flow, leading to faster drying.

In some examples, air may also flow into the device through the perforations or apertures in outer layer. In some examples, the entire layer may be perforated, while in others only one section, such as the proximal end may be perforated. In other examples, the outer layer may comprise a small number of apertures (e.g., one or two apertures). The apertures may reside near the proximal end of the device and, since in some examples the net flow rate in the device is away from the proximal end, the flow may ensue in much the same manner as if air is drawn in through a semi-permeable layer. However, if the perforations or apertures are very large, they may permit leakage of urine in the proximal direction onto the patient. Furthermore, in some examples, air ports may not be necessary because the air gaps may exist around the periphery where the layers attach which may provide adequate ventilation. One skilled in the art will recognize that there are other ways for providing air to the device, such as through ports and valves or through gaps, voids, between layers; all of such variations are within the scope of this disclosure.

Figure 23C:
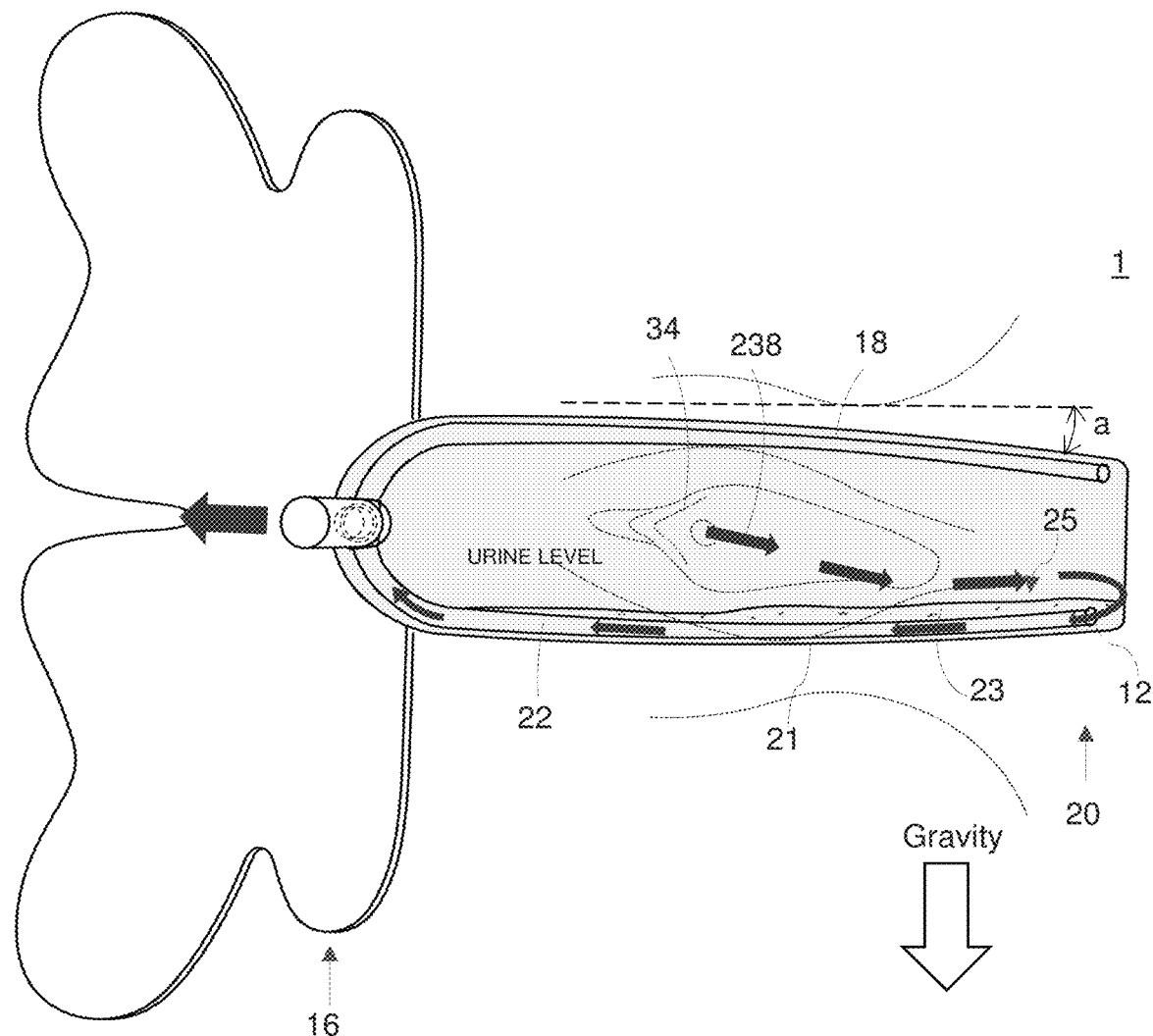
FIG. 23C illustrates a urine removal device oriented on a side showing urine flowing into a conduit.

FIG. 23B shows the device 1 sideways as if a user is lying on her side in the orientation indicated by the gravity arrow. In such orientation, the urine may settle more to the bottom of the device. The shape of the device 1 (at least the layer portion) is generally rectangular with a proximal end 16 that has rounded corners and a distal end 20 that is relatively blunt, as illustrated in a top view in FIG. 23B. The device 1 of FIG. 23B is filled partially with urine 23 and it is lying on its side such that the urine 23 settles to one side of the device 1. The fluid inlet 12 of the conduit 22 resides near to but before the distal end 20 of the device 1 so that it cannot become blocked by the end of the device 1 where the layers meet. In addition, the fluid inlet 12 of the conduit 22 lies adjacent to the side 21 so that it is below the urine 25 that accumulates in the distal end 20 of the device 1. Thus, even in this sideways orientation, the side 21 of the device 1, being relatively horizontal, allows the conduit 22 to reside relatively flat so that even when the fluid level decreases, the conduit 22 will still be able to aspirate most of the urine 23 that has accumulated to the side 21 of the device 1. FIG. 23C shows the flow of urine (indicated by arrows 238) into the conduit 22 that is lower and exposed to urine. In examples, the taper angle "a" of the device 1, may be as little as 0 degrees or larger, such as 15 degrees. Having two conduits positioned on opposing sides of the device can accommodate suction while the device/user is lying sideways in either direction.

When the device is tilted, as in FIGS. 23B-23C, the urine level may be so low that the fluid inlet 12 is not submerged in urine. This can cause the conduit to suck in air leaving a pool of urine towards the proximal end of the device 1. As such, in some examples, a conduit may have multiple inlets along its length providing fluid communication with the layer(s). Having multiple inlets along the length of the conduit may reduce the amount of pooled urine and the rate of evacuation because there is a greater chance of having one of the inlets submerged in urine when the device sits at various device orientations. In other examples, a conduit may be multi-lumen with each lumen having side openings at various lengths along the lumen mitigate pooling at various device orientations. In yet other examples, there may be multiple conduits of different lengths adjacent to each other such that the tip of each conduit presents a different inlet along the side of the device, again, to mitigate the chance of missing pooled fluid when the device resides in various tilted positions. Alternatively, FIGS. 6A-6B illustrate a device 61 having a substantially continuous connection between the conduits 65 and 66 and the layer portion. That is, the lumens 67 and 68 of the conduits 65 and 66, respectively are exposed to the layer 63 along the length of the layer 63 rather than solely at the end. Such a configuration would tend to evacuate even small amounts of urine accumulating toward the lower side when the device 61 when tilted because urine can be drawn into the conduit anywhere along its length where the layer(s) intersect.

In some examples, urine evacuation may be improved by having one conduit blocked so that suction is preferentially diverted to another conduit member. With reference to FIG. 23B again, which shows the urine removal device 1 tilted sideways during use; the overall orientation is indicated by the arrow depicting gravity. Since the first conduit 18 is not exposed to much urine, if any, the conduit 18 will suck in predominantly air which may reduce the suction of the second conduit 22 which is exposed to more urine due to the gravitational settling of the liquid. A conduit system having a valve that automatically blocks the upper conduit while allowing the lower conduit to maintain suction may increase the efficacy of the evacuation. One such valve example is illustrated in FIGS. 24A-24B.

Figure 24A:
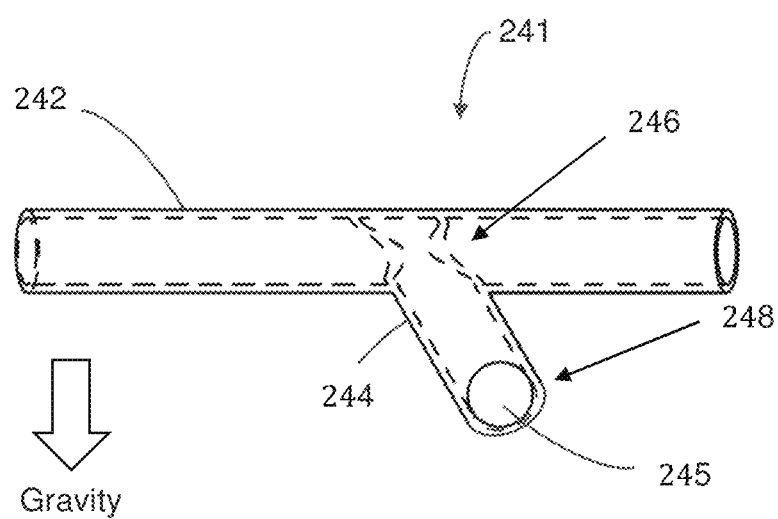
FIG. 24A illustrates an example of a section of a conduit having a valve, wherein the valve is in the open configuration.

FIG. 24A illustrates an example of a valve 241 for blocking flow in a conduit. The valve 241 comprises a section of a main conduit 242 for evacuating urine, a branch 244 extending from the conduit 242, and a ball 245 captive inside of the branch 244. The ball 245 is constrained to move between the end 248 of the branch and a retainer 246 inside of the lumen of the conduit 242. The retainer 246 prevents the ball 245 from migrating along the conduit 242 and also provides an interface for the ball 245 to settle against to block flow. As shown in FIG. 24A the valve 241 is in the open position such that flow is permitted through the conduit 242.

Figure 24B:
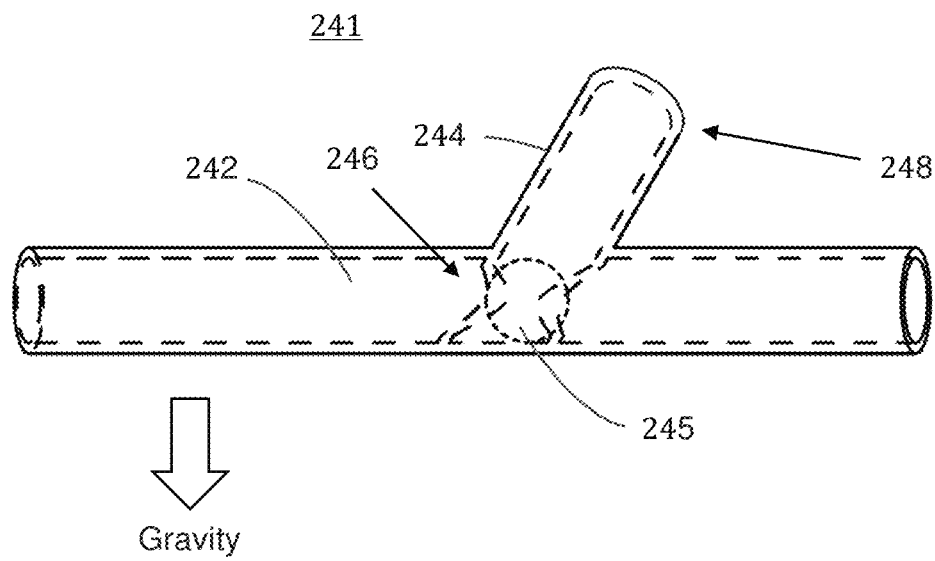
FIG. 24B illustrates an example of a section of a conduit having a valve, wherein the valve is in the closed configuration.

FIG. 24B shows the valve 241 in the opposite (inverted) position wherein the flow in the conduit 242 is blocked. When the branch 244 is substantially aligned with gravity, the ball 245 falls until it is stopped by the retainer 246, such that the ball 245 resides in the lumen of the conduit 242 thus blocking or partially blocking fluid (air or liquid) flow past the ball 245. One skilled in the art would recognize that the ball 245 should be sized so that it fits into the retainer 246 at least partially blocking the conduit 242 while still being free to translate back into the branch 244 when the orientation of the valve 241 changes. In examples, a valve section may be integral to the conduit member, or it may be a modular joint, like a "T" joint that can be attached in-line to a conduit.

Figure 25A:
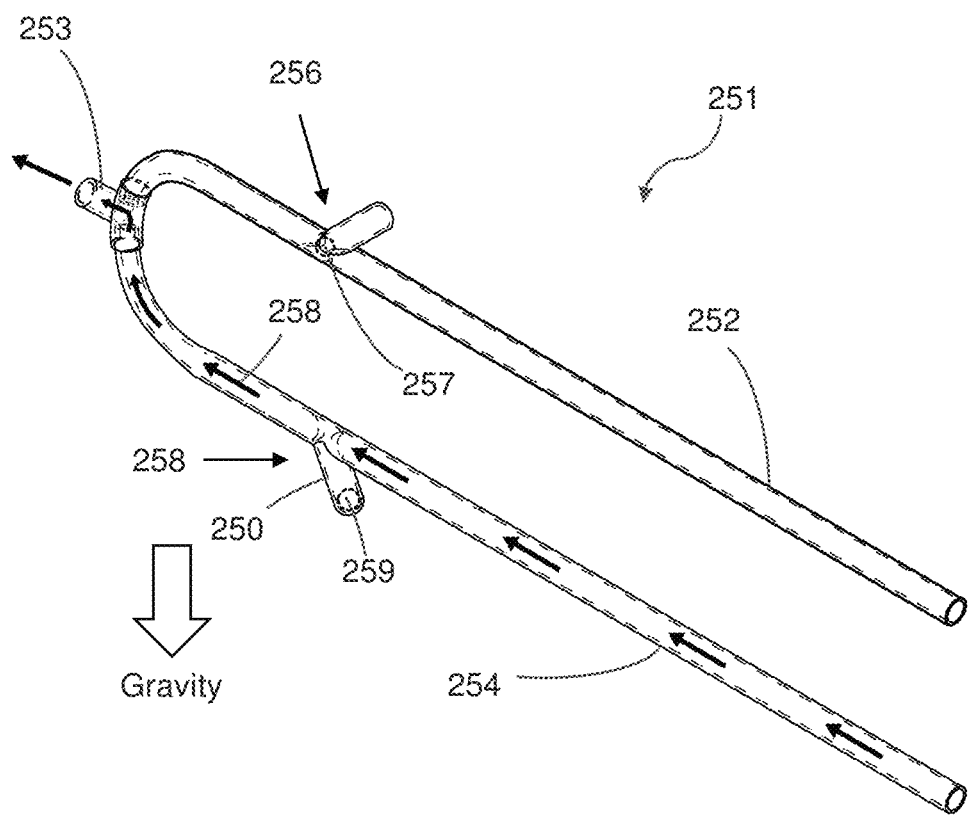
FIG. 25A illustrates an example of a conduit system oriented on an angle with respect to gravity.
Figure 25B:
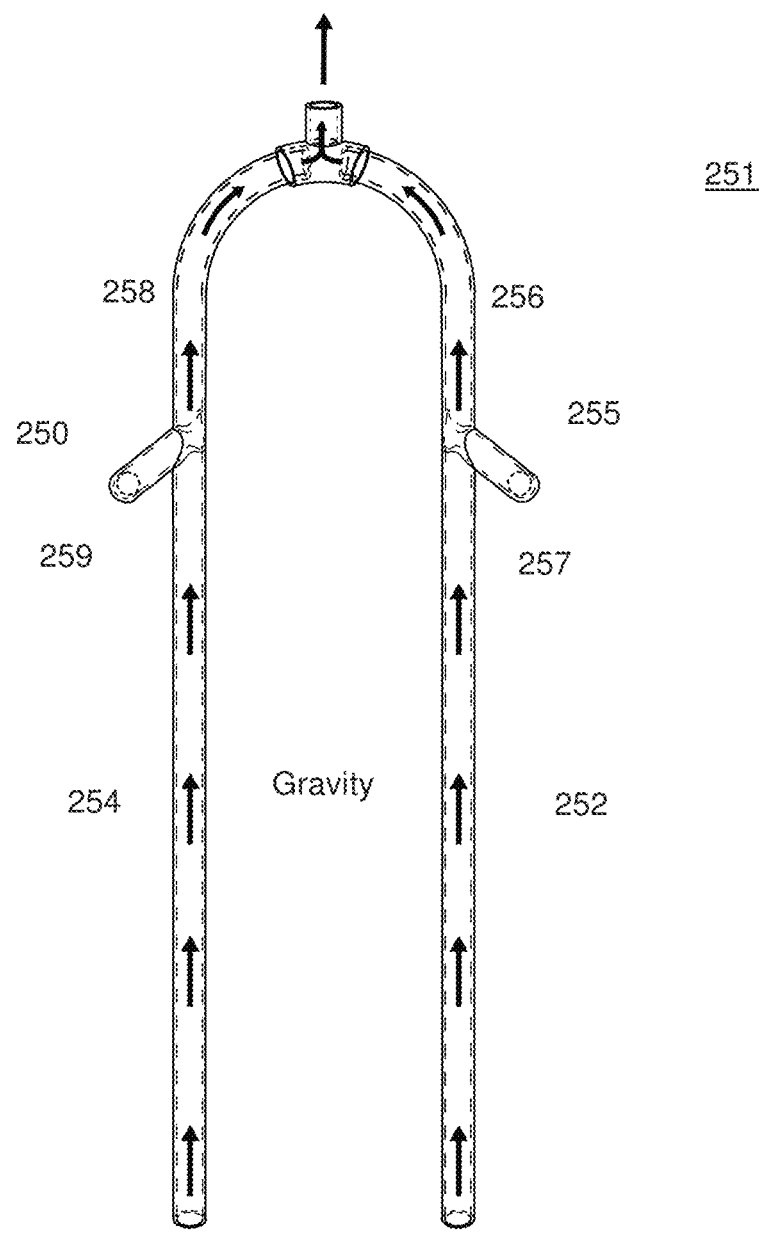
FIG. 25B illustrates an example of a conduit system oriented vertically with respect to gravity.

FIGS. 25A and 25B illustrate a conduit system 251 having a first valve 256 and a second valve 258, located on a first conduit 252 and a second conduit 254, respectively. In this example, each valve is similar to that shown in FIGS. 24A and 24B, however, the valves 256 and 258 have opposing orientations (facing away from the centerline of the conduit system 251) on each conduit 252 and 254 such that only one valve closes when the system 251 tilts. In the orientation shown, the second valve 258 is in an open condition such that the ball 259 captive at the end of the branch 250, i.e., away from the lumen of the second conduit 254. The flow through the conduit is indicated by the arrows (e.g., arrow 258) through the second conduit 254 and out of the suction conduit 253. In contrast, the first valve 256 is in the closed state because the ball 257 has fallen into the lumen of the first conduit 252, thus partially or full blocking air flow and resulting in a stronger suction through the second conduit 254 that is exposed to urine (not shown).

Now with reference to FIG. 25B, which shows the conduit system 251 of FIG. 24A in an upright orientation as if looking at a patient who is standing—gravity is pointing downward. The conduit system 251 shown in FIGS. 24A-24B has straight conduits for simplicity, but the conduits may be shaped in any manner when embodied in a device, for example, they may be curved in a manner similar to the urine removal devices disclosed herein. In this orientation, the branches 255 and 250 of the first and second valves 256 and 258, respectively, are oriented laterally outward and pointing somewhat downward from each conduit 252 and 254, respectively. In the state shown, the conduit system 251 is open in both branches so that flow may ensue, as both conduits 252 and 254 are open to fluid flow as indicated by the arrows. Thus, to accommodate both scenarios where the patient is standing and lying in bed with the conduit system on an angle, the branches may be tilted downward and outward. One skilled in the art would recognize that conduit systems may comprise various shapes, and valves may be placed at various places along the conduits and in various orientations. The placement and orientation of the valves shall be such that they are clear of the anatomy and that they provide the desired valving function when the system is tilted to a trigger angle. In this sense, the system may be tailored to restrict flow to one conduit based at a desired angle.

One skilled in the art will recognize that there are many types of tilt activated valves that may be used for the purpose of substantially blocking one conduit when a urine capture device tilts such that urine pools to one side of a urine removal device. The examples shown in FIGS. 26-28B provide further examples, and other valve examples accomplishing this function are within the scope and contemplated by this disclosure.

Figure 26:
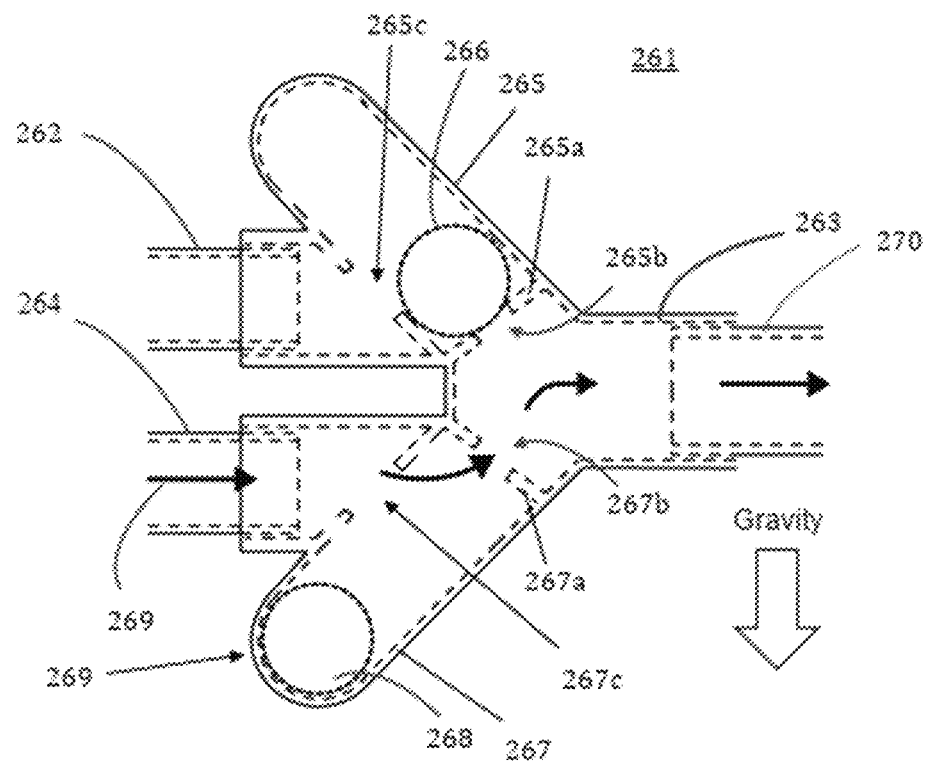
FIG. 26 illustrates an example of a ball valve system oriented on a side, wherein one valve is opened and one is closed.

FIG. 26 shows another valve system 261 having a modular design wherein first and second conduits 262 and 264 attach at a first end, and an exit conduit 270 attaches at the opposite end 263. The valve system 261 is shown in a sideways orientation as indicated by the "gravity" arrow. The valve system 261 comprises a first branch 265, which houses a first ball 266, and a retainer 265a to stop the first ball 266 when tilted to a certain degree, as shown. When the first ball 266 is stopped as shown, it blocks an end aperture 265b in the retainer 265a to prevent flow of fluid (liquid or air) which would otherwise flow through the pathway which originates at the first conduit 262, through a side aperture 265c, into the first branch 265, and through the end aperture 265b which leads to an exit conduit 270. In contrast, the second branch 267 of the valve system 261 has a second ball 268 which is disposed in the distal end 269 of the second branch 267 due to the force of gravity, leaving the retainer 267a unblocked. As such, the second branch 267 is open, thus allowing fluid to flow from the second conduit 264, through a side aperture 267c, through an end aperture 267b and out through the exit conduit 270, which may be a suction source conduit or another segment of conduit.

Figure 27:
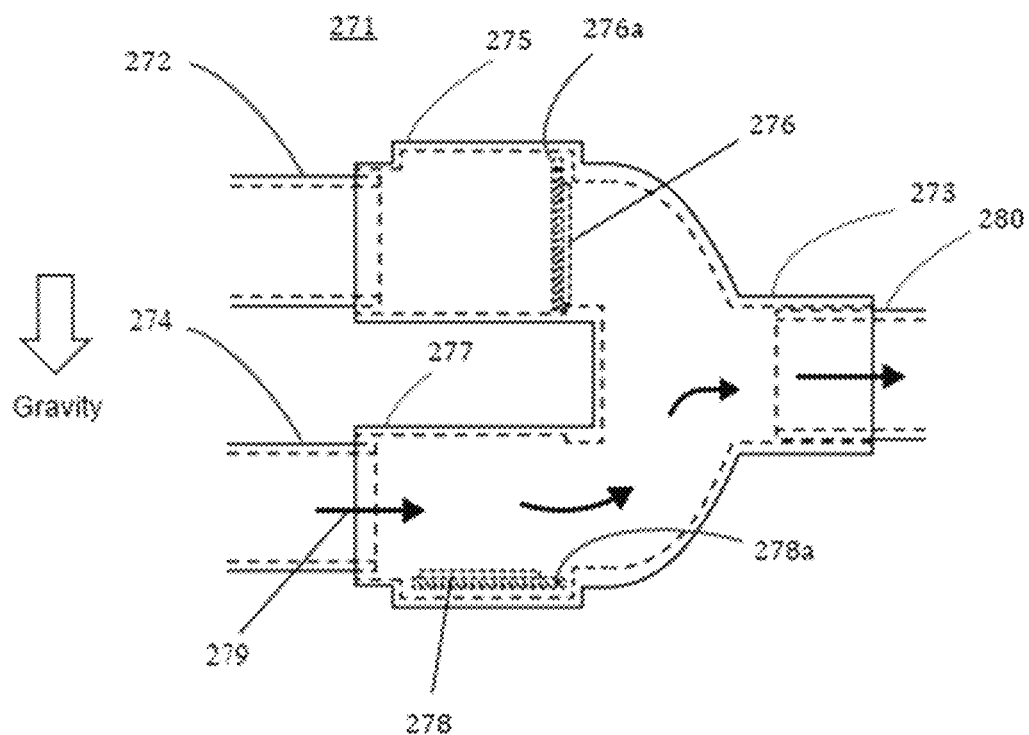
FIG. 27 illustrates an example of a flap valve system oriented on a side, wherein one valve is opened and one is closed.

Yet another valve system 271 is shown in FIG. 27. This system 271 comprises a pair of flap valves 276 and 278 that rotate under gravity and is shown in a sideways configuration indicated by the "gravity" arrow. The valve system 271 comprises a first branch 275 in fluid communication with a first conduit 272 and a second branch 277 in fluid communication with a second conduit 274. As shown, the first branch 275 has a blocked flow path and the second branch 277 has an open flow path to the outlet 273 which connects to another conduit 280. The branches 275 and 277 comprise flap valves 276 and 278, respectively, that can open and close based on the orientation of the valve system 271 with respect to gravity. The first flap valve 276 has a hinge 276a where it attaches to the first branch 275 and, as shown, the weight of the valve 276 has pulled it down into a closed position. In contrast, the second flap valve 278 has a hinge 278a at its base where it contacts the second branch 277 and resides in the nominal or open position as shown. Thus, in this configuration fluid may flow, as designated by the solid arrows (e.g., arrow 279) from the second conduit 274, through the second branch 277, out of the outlet 273 and into the conduit 280 that is downstream. Both valve systems 261 and 271 shown in FIG. 26 and FIG. 27, respectively, are modular in that they may be connected to conduits by press fitting, bonding, or any other method of joining plastic parts. In some examples, the valve systems may be made integral to the conduits in a single molded part or an insert mold, for example.

Figure 28A:
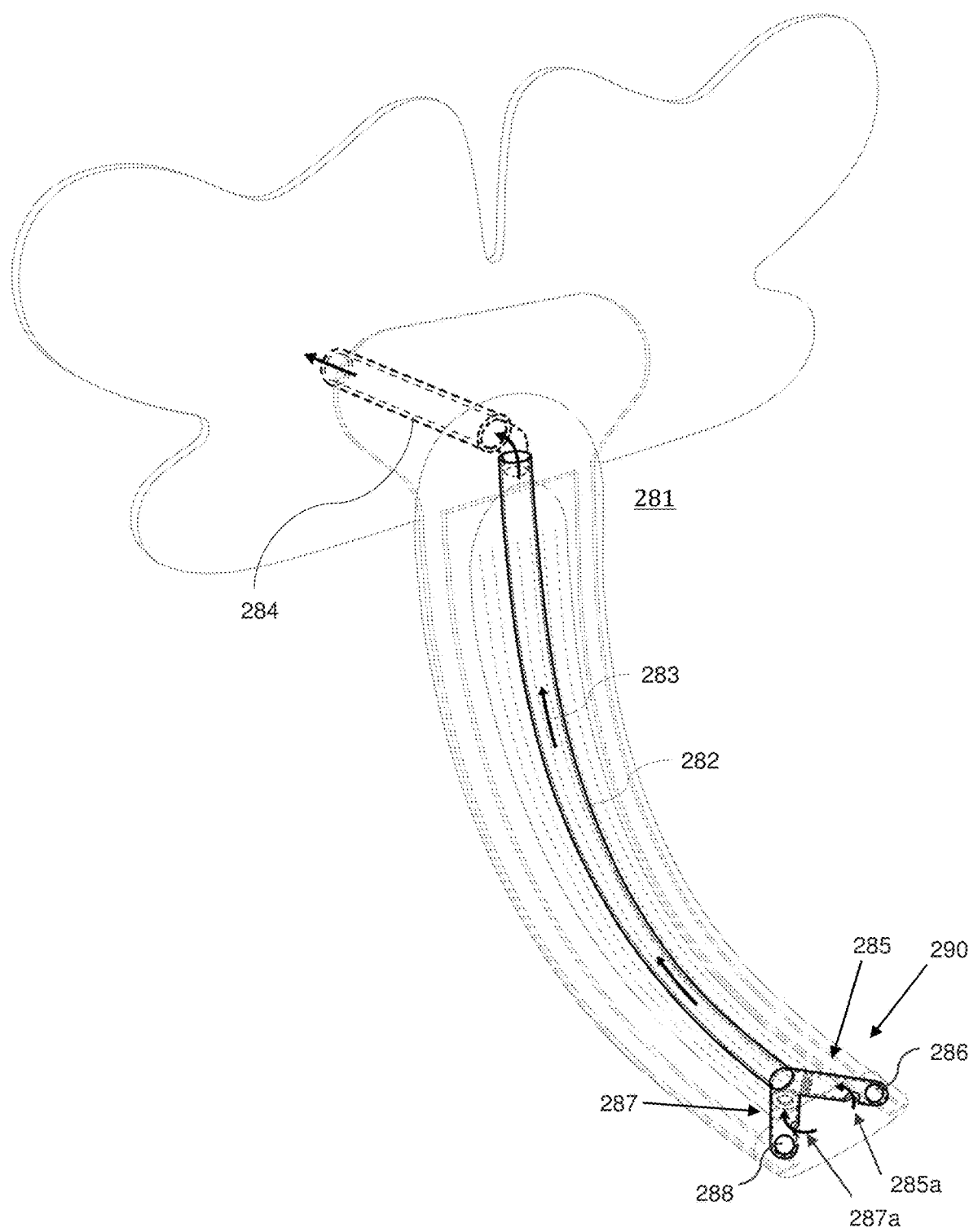
FIGS. 28A-28C illustrate an example of a conduit system having single conduit and a valve system disposed at the distal end of the conduit.
Figure 28B:
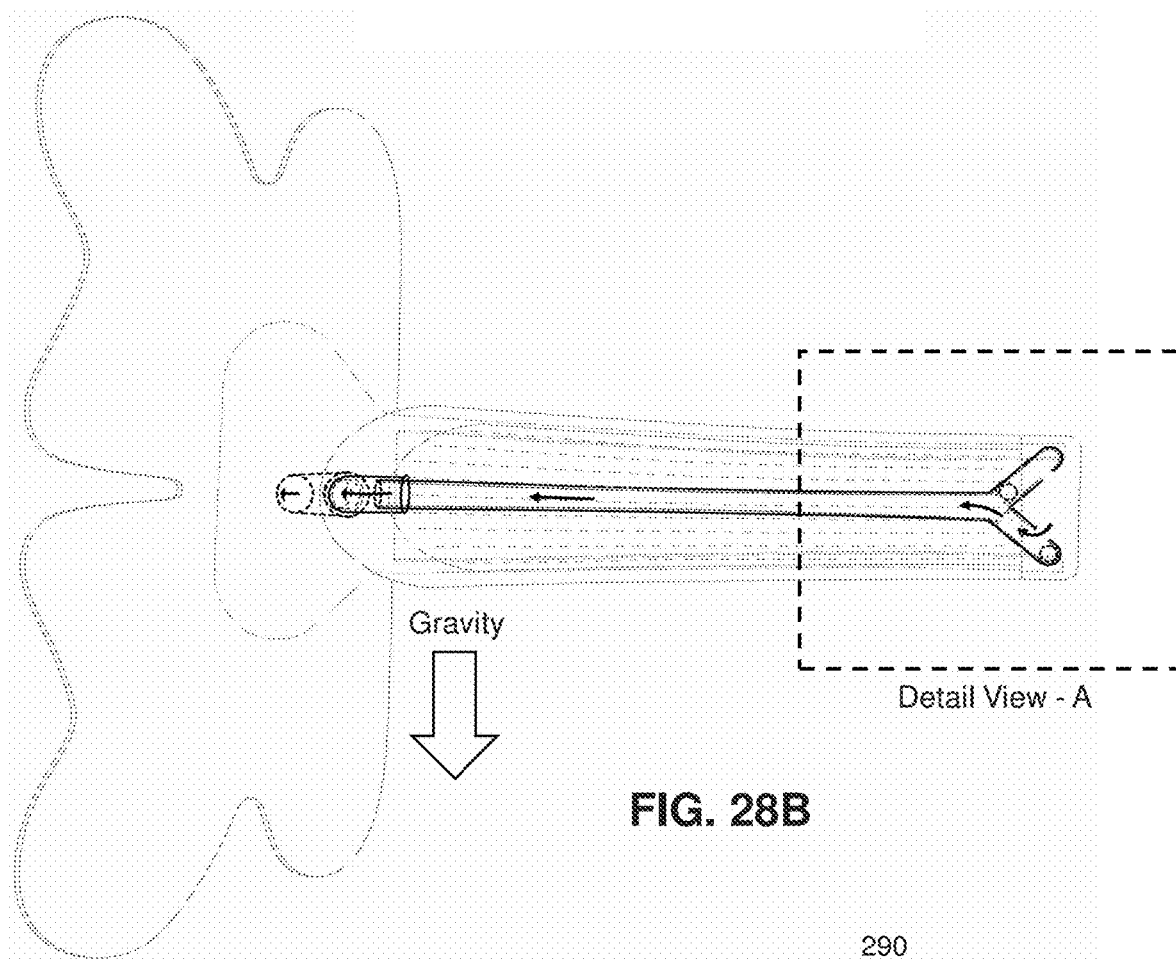
Figure 28C:
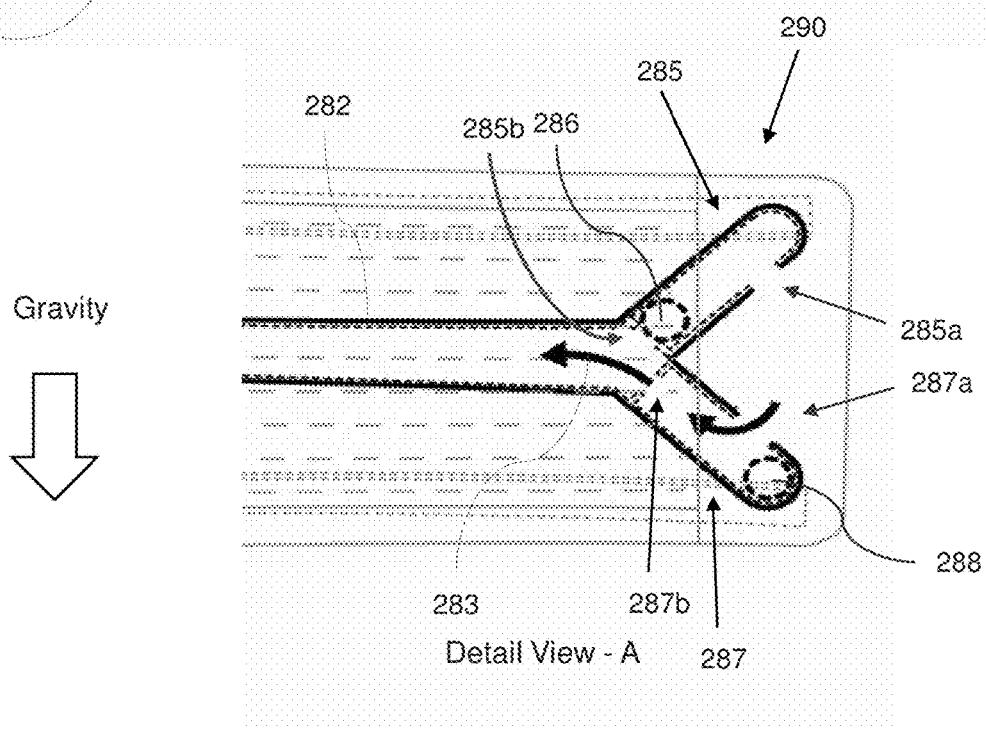

Another configuration of a conduit system 281 having a valve arrangement is shown in FIGS. 28A-28C. A single conduit 282 connects between a suction source tube 284 and a valve system 290. The valve system 290 comprises a first branch 285 and a second branch 287, each having a fluid inlet 285a and 287a, respectively. The fluid inlets 285a and 287a are located on a side of each branch 285 and 287 and they are in direct fluid communication with the space between the layers that is exposed to urine. That is, the urine is directly drawn into the fluid inlets 285a and 287a. In the configuration shown in FIG. 28A, the valve system 290 is fully open, since it is not tilted to a trigger angle, and the ball 286 of the first branch 285 is disposed at the distal end of the branch; similarly, the ball 288 of the second branch is disposed at the distal end of the second branch 287, leaving the retainer 287b unblocked. Thus, fluid may be drawn through the fluid inlets 285a and 287a, into the conduit 282, and out through the suction source tube 284 as shown by the solid arrows (e.g., arrow 283).

FIG. 28C shows the conduit system 281 in a sideways orientation indicated by the "gravity" arrow and depicts the detail view-A taken for FIG. 28B. FIG. 28C. illustrates the valve system 290 oriented on a side. In this orientation, the first conduit 285 is closed because the ball 286 is pressed against aperture 285b (retainer), thus closing off flow through inlet 285a to fluid (i.e., air since it may not be exposed to liquid). In contrast, the second branch 287 is open because the ball 288, forced by gravity, is displaced toward the distal end of the branch 287 thus allowing fluid to flow into the conduit 282, as indicated by the solid arrows.

Figure 29A:
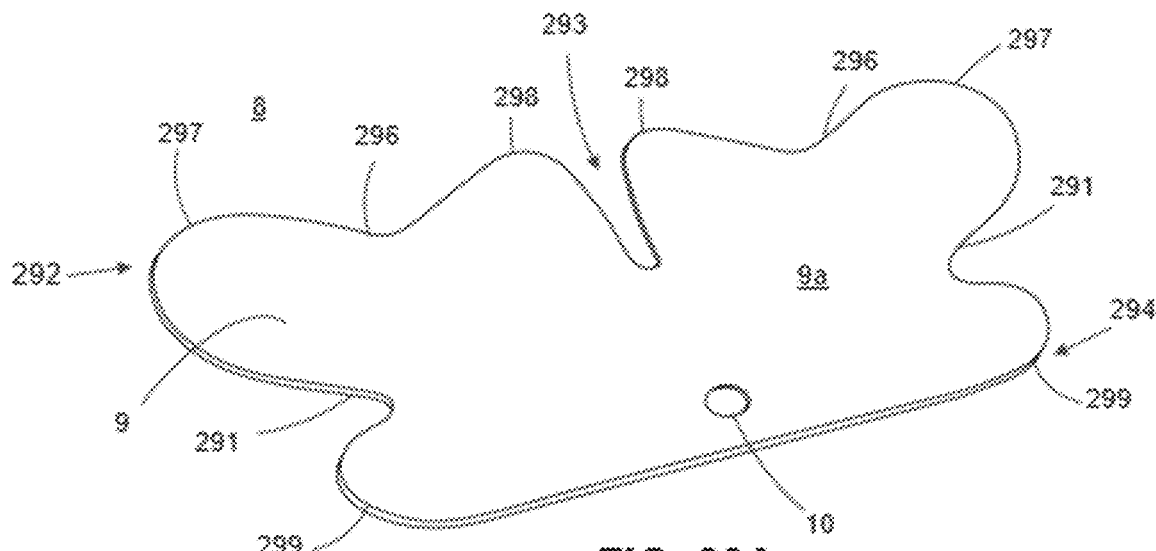
FIG. 29A illustrates a perspective view of an adhesive patch according to an example.

There are many shapes and configurations of adhesive patches that are suitable for the devices disclosed herein. The example of an adhesive patch 8 illustrated in FIGS. 1A-1B, and other figures in this disclosure, is further illustrated in FIGS. 29A and 29B. The adhesive patch 8 has an aperture 10 suitable to accommodate a conduit, a wide proximal end 292, and a wide distal end 294 which attach to the lower abdomen and suprapubic region respectively, as also shown for example, in FIG. 4B. In examples, the adhesive patch 8 may have a narrowed central section defined by concave sidewalls 291 as shown in FIG. 29A. The wide proximal end 292 provides a large surface area to improve adhesion to the body while stabilizing against twisting motions where it attaches to the abdominal region. The width of the proximal end 292 may be approximately 15 cm across or between 2 and 30 cm across in examples. The proximal end 292 may have a central slit 293 and one or more recesses 296 dividing the adhesive patch 8 into proximal tabs 297 and medial tabs 298. The slit 293 and recesses 296 can reduce tension or compression of the adhesive patch 8 during body movement by providing a relief between each section of attached skin that is deforming, thus allowing the adhesive patch 8 to deform with the body without excessively resisting the motion, which can cause discomfort or lead to dislodgement. The slit 293 and recesses 296 may be straight cuts, curves, or they may be approximately "v" shaped or any other shape providing reliefs so that different portions of the patch may deform with the skin without significant resistance.

The distal end 294 may be narrower than the proximal end 292 because the suprapubic region may narrow relative to the abdomen. The width of the distal end 294 may be approximately 14 cm across or, for example, from 2 cm to 30 cm in some examples.

The central section 291 may be approximately 9 cm across or from 5 cm to about 20 cm in some examples. The anatomical topology consists of rather variable surfaces in the region of the central section so the reduced width can lessen the contact, and therefore the forces transferred, due to movement of the skin, which can reduce the incidence of dislodgment of the adhesive patch 8.

Figure 29B:
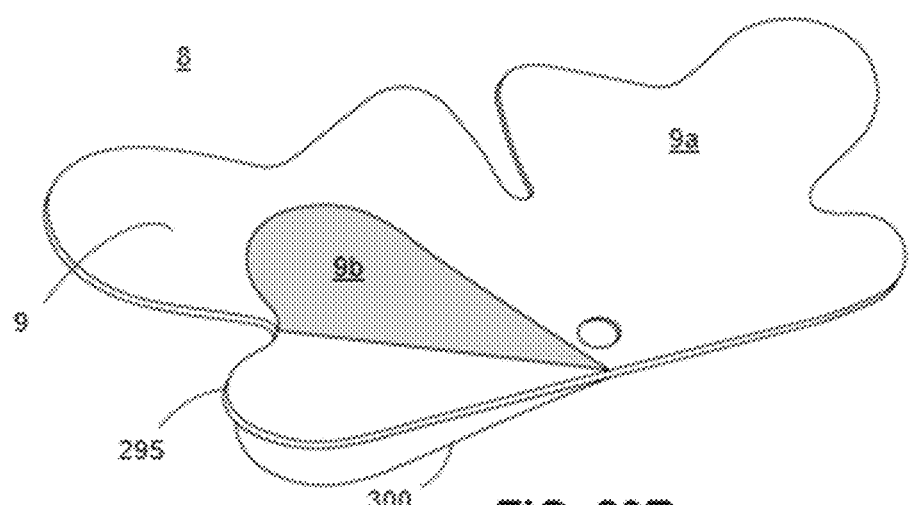
FIG. 29B illustrates a perspective view of the adhesive patch of FIG. 29A showing various layers according to an example embodiment.

FIG. 29B shows the adhesive patch 8 with the layers separated on a corner to more clearly show the different layers in this example. The substrate layer 9 is a fixed layer in that it is permanently attached to the layers (not shown, but see FIG. 1B), for example on its outer surface 9*a* and it is attached to the adhesive layer 295 on its inner surface 9*b*. The adhesive layer 295 may comprise a single adhesive layer or a layup of a plurality of layers configured to conform with skin on one side and the substrate layer 9 on the other side. The substrate layer 9 may be coupled to the layers or the base of the frame by thermal welding (heat staking), bonding with solvents or adhesives, or any other method for attaching thin layers. The substrate layer 9 is generally provided coupled to the layers and/or base so that the adhesive patch 8 is already in place, but, in some examples, it may be provided uncoupled so that the operator attaches it to the remainder of the device before use. The substrate layer 9 may be made of any material that allows it to adhere to both the adhesive layer 295 and the layers or base; examples include but are not limited to a single or a mixture of a natural or thermoplastic or thermoset polymer in sheet, film, woven or non-woven fabric form; example materials include polyethylene, polypropylene, thermoplastic elastomer (TPE), polyurethane, EVA (ethylene-vinyl acetate), nylon, rayon, etc. In some examples, the substrate layer 9 may have a peel strength (relative to the adhesive layer 295) greater than 0.1N/cm.

The adhesive layer 295 is sandwiched between the substrate layer 9 and the release liner 300. The inner surface (not shown) of the adhesive layer 295 is suitable for attachment to the body in the abdomen and suprapubic area. The adhesive layer 8 is amenable to adhesion and removal from skin even with hairs emanating from the skin, while being flexible enough to move and deform with the skin without peeling off. The peel strength with respect to steel can be approximately 0.1-5 N/cm in some examples. One skilled in the art will recognize that there many candidate materials that will adhere to the skin for the wearable duration of urine capturing, adhere to the substrate layer 9, be easily removable without excessively pulling on the skin and hair, and leave behind little or no residue on the skin. For example, porous or nonporous silicone adhesives may be particularly suitable as they are comfortable to the patient and may leave no perceptible residue. Other candidate materials include pressure-sensitive adhesives, namely a variety of rubber-based materials, gel-matrix type adhesives like hydrocolloids and hydrogels, and thermoplastic-based adhesives including polyurethanes and acrylics, as well as natural adhesive obtained from various plants or animals.

The release liner 300 covers and protects the adhesive layer 295 before use, that is, during manufacturing, shipping, and handling. The release liner 300 releases relatively easily from the adhesive layer 295 so that the adhesive does not stretch and rebound when the operator peels the layers apart, as this may cause the adhesive patch 8 to fold and stick to itself. The release liner 300 should have a peel strength away from the adhesive that is less than both the peel strength between the adhesive layer 295 and the substrate layer 9, and less than the peel strength between the substrate layer 9 and the layer or base where the substrate layer attaches. One skilled in the art will recognize that there are many candidate materials that are suitable to protect the adhesive layer 295 in such a way, such as, for example, paper-based liners including different combinations of coated and densified kraft papers and laminated papers, or film-based liners such as high-density polyethylene and polyester thermoplastics. Additionally, the use of release agents along with the release liners may be used.

Figure 30:
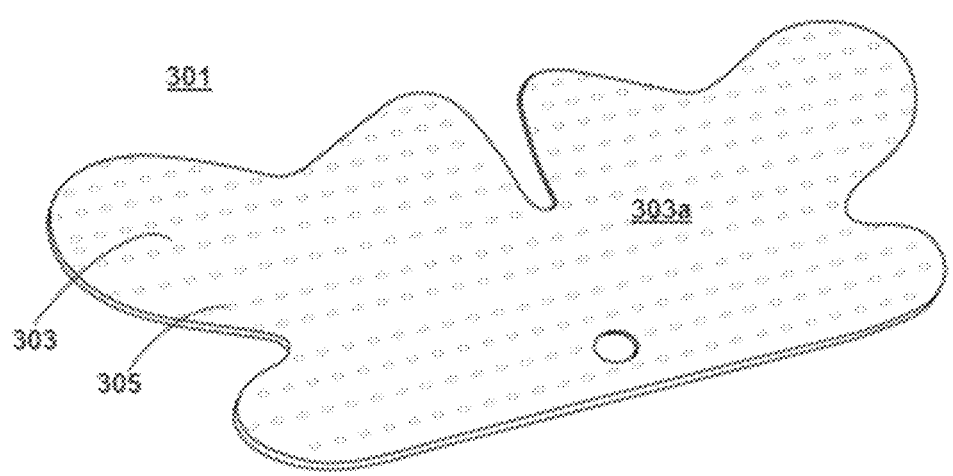
FIG. 30 illustrates a perspective view of an adhesive patch.
Figure 31:
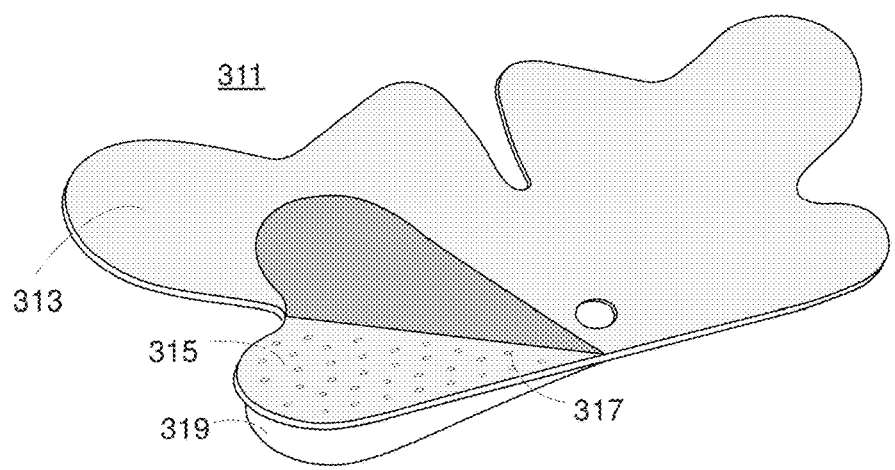
FIG. 31 illustrates a perspective view of an adhesive patch having perforations according to another example embodiment.
Figure 32:
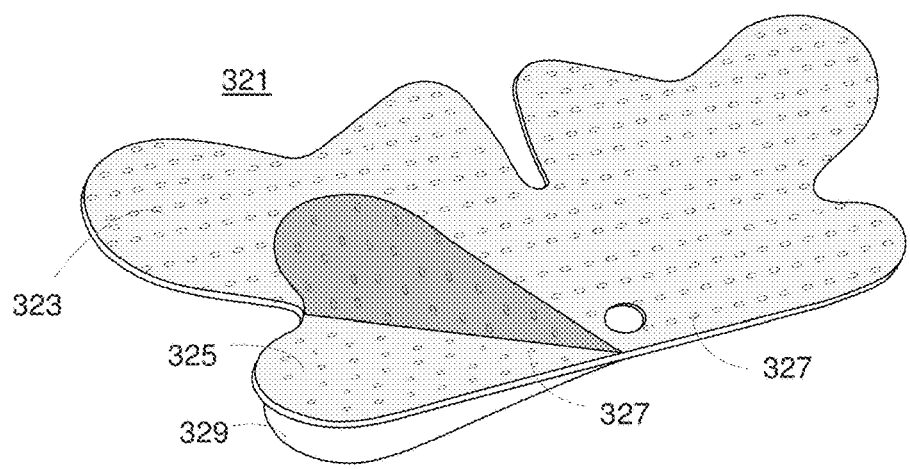
FIG. 32 illustrates a perspective view of an adhesive patch having perforations showing various layers according to another example embodiment.

One or more of the layers in the adhesive patch may be perforated to allow sweat to evaporate to reduce skin maceration. With reference to FIG. 30, an adhesive patch 301 is shown having a substrate layer 303 with perforations 305 shown in the outer surface 303*a*. In this and the following figures, while the reference numeral points to one perforation, it pertains to the entire array of perforations shown. The perforations 305 may channel through the entire thickness of the substrate layer 303. Alternatively, as shown in FIG. 31, only the adhesive layer 315 may have perforations 317 for improving sweat evaporation. In this adhesive patch 311, the substrate layer 313 is not perforated and the release liner 319 need not be perforated. Finally, as shown in FIG. 32, the adhesive patch 321 both the substrate layer 323 and the adhesive layer 325 have perforations 327 to further enhance sweat evaporation from the skin, while the release liner 329 is not perforated.

Figure 33:
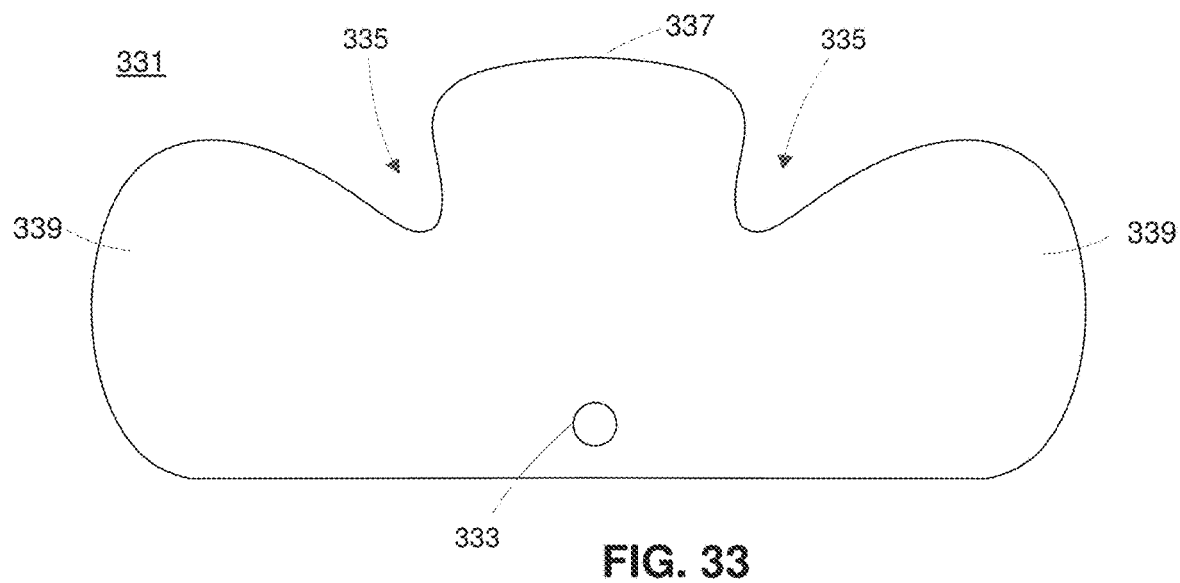
FIG. 33 illustrates an adhesive patch shape according to an example embodiment.
Figure 34:
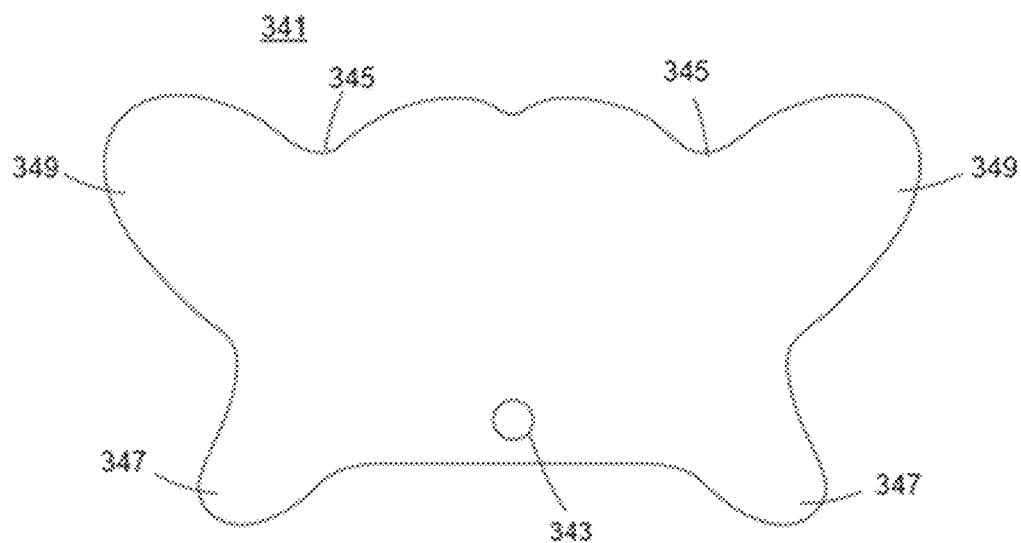
FIG. 34 illustrates an adhesive patch shape according to another example embodiment.
Figure 35:
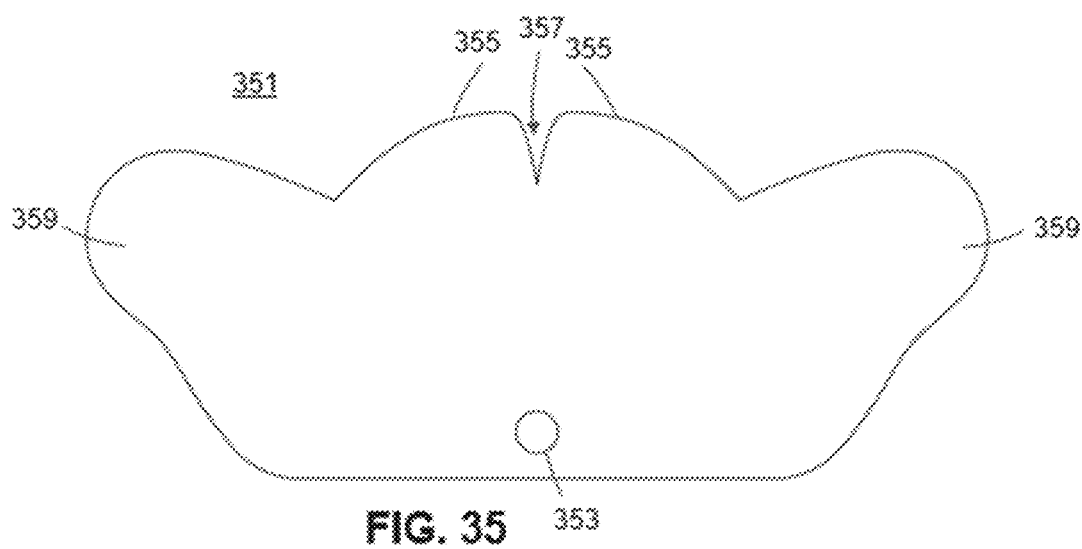
FIG. 35 illustrates an adhesive patch shape according to another example embodiment.
Figure 36:
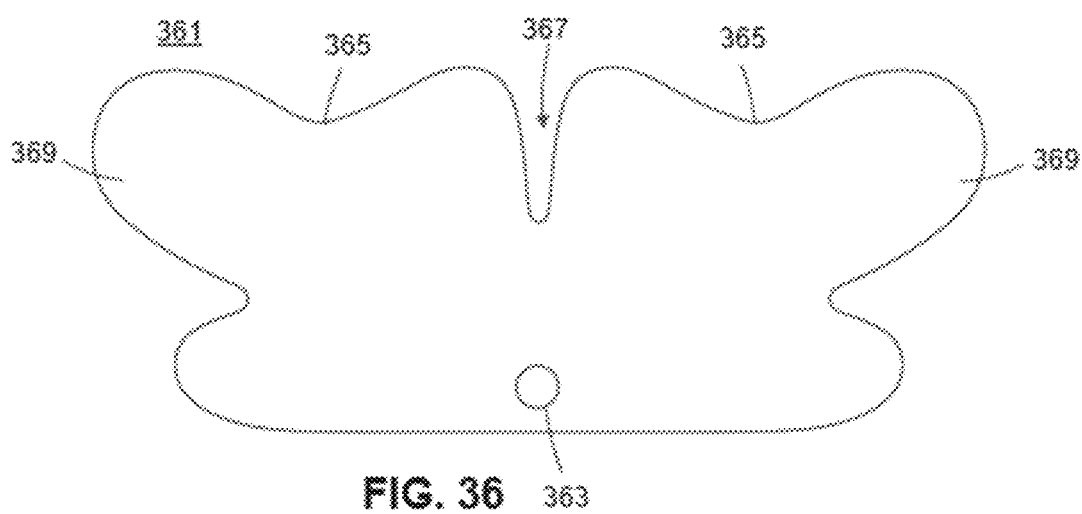
FIG. 36 illustrates an adhesive patch shape according to another example embodiment.

One skilled in the art will recognize that there are many different shapes of the adhesive patch that can be effective to fit within the anatomy around the abdomen and suprapubic area while being flexible to conform to deforming skin. FIGS. 33-36 illustrate several examples having various shapes as nonlimiting examples; in the examples, the aperture identified designates the region through which a conduit is placed and proximal is upward on each figure. FIG. 33 shows an adhesive patch 331 having an aperture 333 near the distal end and a pair of recesses 335 along the proximal side separating the proximal side into a broad central tab 337 and two side lobes 339. FIG. 34 shows an adhesive patch 341 having an aperture 343 and small flanges 347 along the distal end. The adhesive patch 341 further comprises a pair of large flanges 349 at the corners of the proximal end and two small recesses 345 along the proximal edge. The adhesive patch 351 of FIG. 35 has an aperture 353 near a flat distal edge and large flanges 359 at the corners of the proximal end. The proximal end further comprises a slit 357 separating two prominences 355. Another example is shown in FIG. 36; the adhesive patch 361 having an aperture 363 near a flat distal end and a pair of large flanges 369 at the corners of the proximal end. The adhesive patch 361 further comprises a relatively large slit 367 separating small prominences 365 along the proximal edge.

Figure 37:
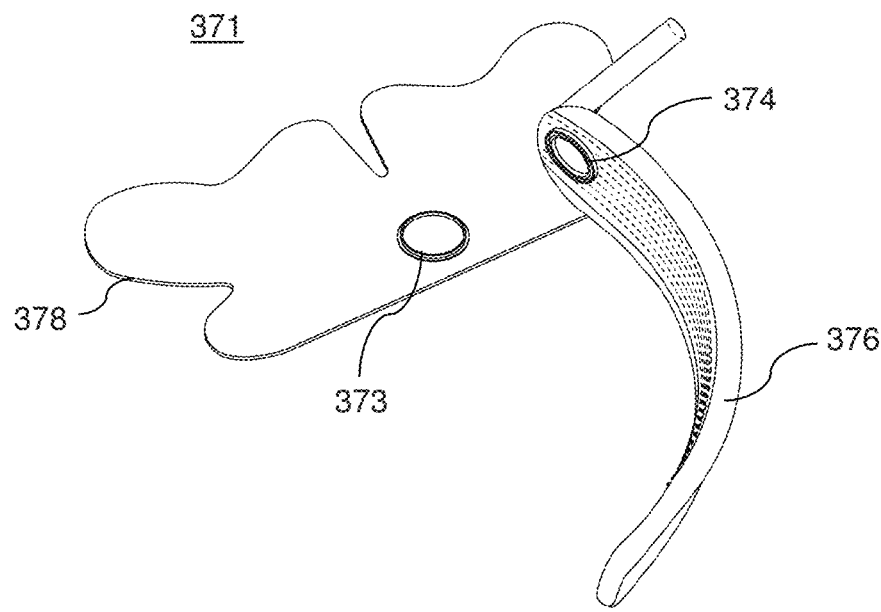
FIG. 37 illustrates a device having a removable attachment for the device.

In some examples (for example, the urine removal device 371 of FIG. 37), an adhesive patch 378 may be removably attached to the layer portion 376. That is, the adhesive patch 378 may be connected to the layer portion 376 via an interface that may use threads, a twist-lock (¼ or ½ turn for example), an interfacing male/female flange pair, or any suitable interfacing component pair (comprising first and second interfacing components configured to interface with each other). The layer portion 376 may have a corresponding interfacing member or receiving member 374 such as a flange to match a connector 373 on the adhesive patch 378. A detachable interface of this kind allows the operator to remove the device for cleaning or replacement while leaving the patch 378 secured via adhesive on the body, which may save the operator time and effort while preventing any discomfort to the user that may be incurred while removing and applying the adhesive patch.

Figure 38:
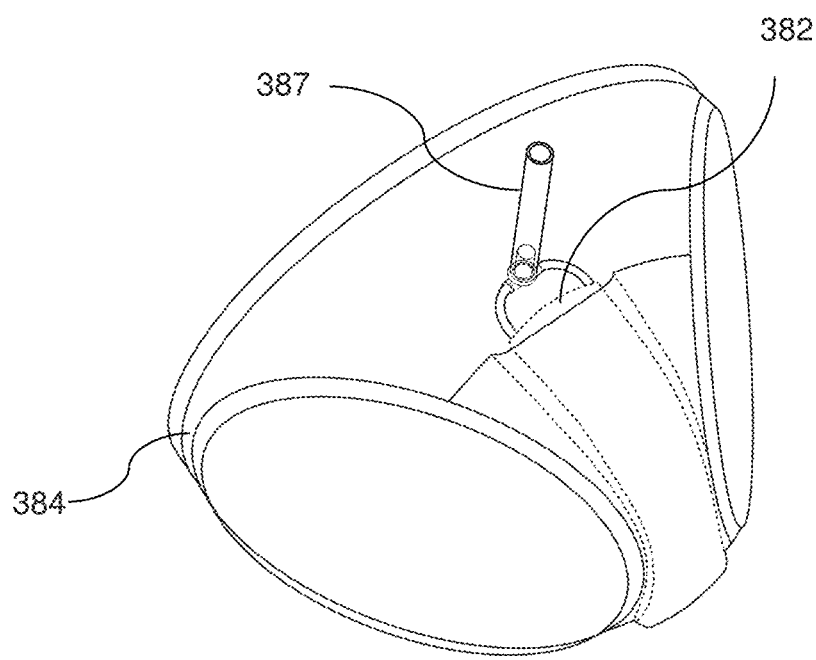
FIG. 38 illustrates a device having a removable attachment from an undergarment.

FIG. 38 illustrates an example of the urine removal device 382 that is capable of being affixed to clothing (for example, a diaper or undergarment 384 worn by a user). As would be apparent from FIG. 38 this example may be incorporate the interfacing mechanism described in connection with FIG. 37. In the example illustrated in FIG. 38, the undergarment 384 to which the urine removal device 382 is affixed is provided with one of an interfacing component pair, or any other suitable interface, while the urine removal device 382 may have the other of the interfacing component pair (comprising first and second interfacing components configured to interface with each other) which enables the urine removal device 382 and the undergarment 384 to be removably interfaced. While the interfacing components are hidden in FIG. 38, they may be similar to the examples shown and described with respect to the example shown in FIG. 37, namely, the first interfacing component may be affixed to urine removal device 382. The undergarment 384 may have an aperture or otherwise be configured to pass a suction source tube 387 that emits from the device 382. The interfacing component pair of FIGS. 37 and 38 may be configured to provide a fluid tight interference between the components.

Method of Use

With respect to the general use of examples of this disclosure, for clarity, a reader should refer to FIGS. 1A-1B, which show an example of a device, FIGS. 4A-4C, which provide a depiction of an example during use on a user, FIGS. 5A-5B which show a depiction of an example during use along with vacuum source, FIG. 29A-29B, which details an exemplar layering of an adhesive patch, and FIG. 38, which represents a flowchart of a use scenario in some examples. The order of operations is for illustration only and is not meant to be limiting, as some operators may prefer an alternate sequence of steps, additional steps, or fewer steps. Such variations and modifications are within the scope and spirit of the inventions and examples contemplated herein.

Figure 39:
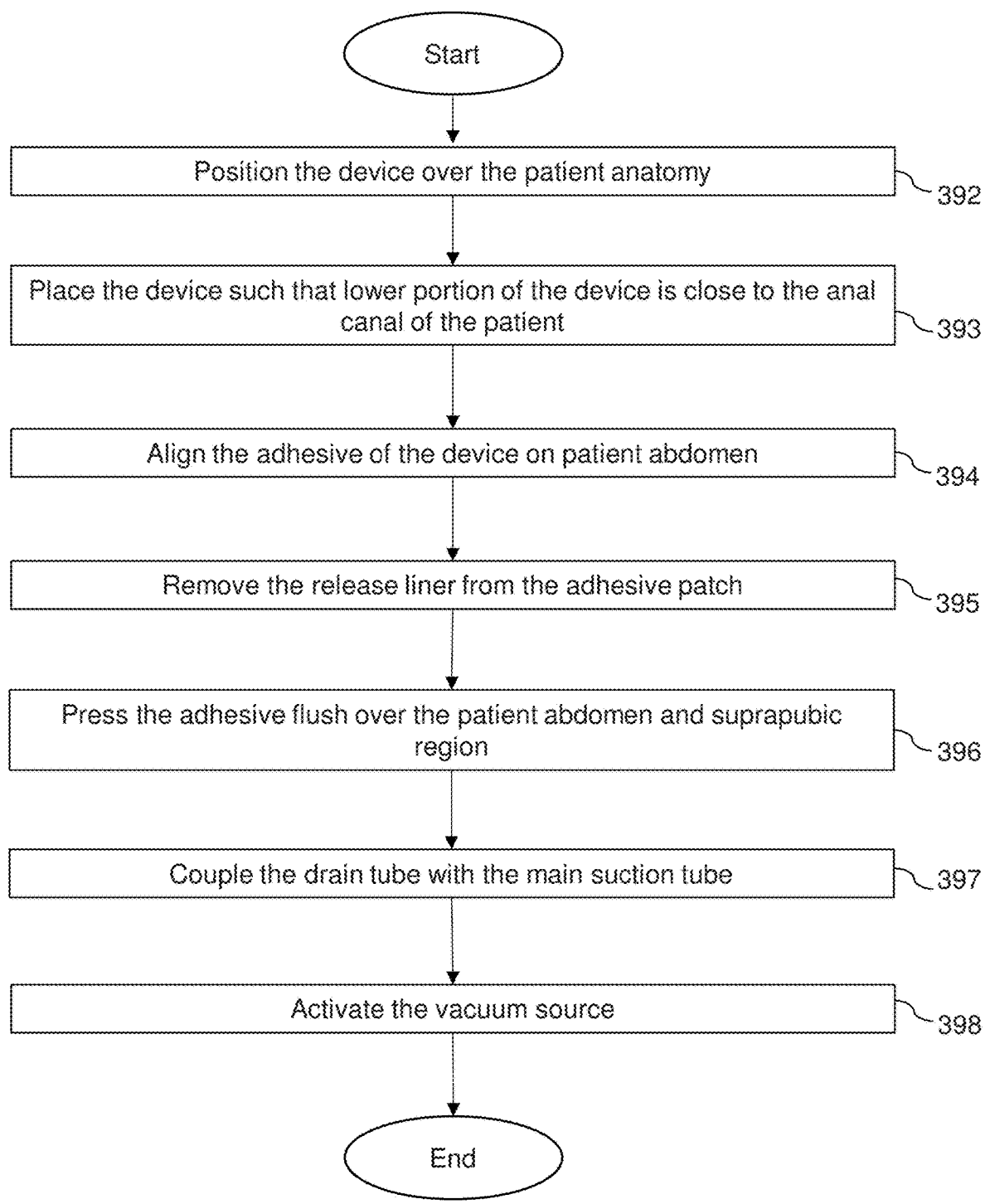
FIG. 39 is a flow chart illustrating the method of using a urine removal device according to an example embodiment.

Referring to FIG. 39 (and FIGS. 1A-1B, FIGS. 4A-4C, and FIGS. 29A-29B) first, a user may position the device 1 over the patient anatomy (step 392), then place the device 1 such that lower portion of the device is close to the anal canal of the patient (step 393). The adhesive patch 8 of the device 1 may be aligned over the patient's abdomen (step 394). The release liner 300 may be removed from the adhesive layer 295 (step 395) to expose the inner surface of the adhesive layer 295 which is sticky or tacky, and press the adhesive patch 8 against the skin such that it adheres the inner surface of the adhesive layer 295 such that it resides flush with the user (step 396). If required, the proximal tabs 297 and distal tabs 299 may be maneuvered either during adhesion or afterward to assist in customizing the adhesive fit with the user. Next, a drain tube 43 may be temporarily and removably coupled with suction source tube 24 (step 397), after which the vacuum source may be activated (step 398). With reference to the flowchart of FIG. 39, as previously noted, it would not be necessary for each step to occur in the illustrated sequence; for example, step 397 may be performed at a number of earlier stages.

The devices described in examples herein provide for urine removal devices that may be used by patients or other users in the prone position, lying sideways, or sitting because the designs are effective at removing urine without leaking and evacuating urine quickly away from the anatomy.

While the invention disclosed herein has been particularly shown and described with references to example examples thereof, it will be understood by those skilled in the art that various changes in form and details may be made therein without departing from the scope of the invention encompassed by the appended claims. Furthermore, while several examples are described, the scope of the examples should not be construed to be limited to those set forth herein. While the above is a description of certain examples, various alternatives, modifications, and equivalents may be used. The various features of the examples disclosed herein may be combined or substituted with one another. That is, each of the components of the various examples may be combined with each other and that the components of one example may be used with the components of another example. Therefore, the above description should not be taken as limiting the scope of the invention which is defined by the appended claims.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for removing urine discharged from a body of a user, the device comprising:
    a frame comprising a base region and at least one branch extending from the base region along a proximal to distal length of the device, wherein the at least one branch is curved to conform to the body of the user;
    a fluid collection region extending distally from the base region, the fluid collection region comprising:
        an inner layer that is permeable to urine and air, and is configured to be placed adjacent to the body of the user such that urine and air enters the fluid collection region through the inner layer,
        an outer layer that is substantially impermeable to urine and permeable to air, and
        a transfer layer disposed between the inner layer and the outer layer;
    a first suction tube extending along a right side of the fluid collection region between the inner layer and the outer layer and ending in a first fluid inlet at a distal end region of the right side of the fluid collection region; and
    a second suction tube extending along a left side of the fluid collection region between the inner layer and the outer layer and ending in a second fluid inlet at the distal end region of the left side of the fluid collection region, wherein the device is configured such that when suction is applied within the fluid collection region from the first fluid inlet at the distal end region of the right side and/or the second fluid inlet at the distal end region of the left side, air entering the device through the inner layer and/or the outer layer is entrained along the proximal to distal length of the device to enhance evaporation and removal of urine within the fluid collection region.

2. The device of claim 1, wherein the at least one branch has a variable stiffness along its length.

3. The device of claim 1, wherein the at least one branch has a variable thickness along its length.

4. The device of claim 1, wherein the at least one branch has a stepped thickness along its length.

5. The device of claim 1, wherein each branch of the at least one branch tapers laterally along its length.

6. The device of claim 1, wherein the at least one branch of the frame is biased with a spring force to curve in a C-shape to conform to the body of the user.

7. The device of claim 1 wherein the at least one branch of the frame is configured as a leaf spring comprising a plurality of curved layers that are coupled together.

8. The device of claim 1, wherein the inner layer and the outer layer are attached at an outer periphery of the fluid collection region.

9. The device of claim 1, further comprising an overhang layer extending over a periphery of the inner layer, wherein the overhang layer is at least partially unattached where it overlaps the inner layer.

10. The device of claim 1 wherein the transfer layer comprises a plurality of flow directors oriented substantially longitudinally along the fluid collection region.

11. The device of claim 1, wherein the transfer layer is formed of a polymeric material having a thickness of 2 mm or less.

12. The device of claim 1 wherein the fluid collection region tapers distally such that a width of a distal end of the fluid collection region is narrower than a width of a proximal end of the fluid collection region.

13. The device of claim 1 wherein the frame comprises a malleable material capable of being conformably fit to the user's anatomy.

14. The device of claim 1 further comprising a finger strap attached near a distal end of the device configured to encircle one or more of the fingers of a hand installing the device.

15. The device of claim 1 further comprising an adhesive patch attached to the base region for attaching to the device to a patient.

16. The device of claim 1 further comprising a suction source tube in fluid communication with the first suction tube and the second suction tube.

17. The device of claim 1, further comprising an air gap between the outer layer and the transfer layer.

18. The device of claim 1, wherein the inner layer comprises a non-absorbing, porous, urine-permeable, hydrophobic layer.

19. The device of claim 1, wherein the outer layer is breathable, substantially impermeable to urine, non-absorbing, and hydrophobic.

20. The device of claim 1, wherein the inner layer, the outer layer and the transfer layer are air permeable.

21. A device for removing urine discharged from a body of a user, the device comprising:

a base region comprising an adhesive patch to secure to the device to the user;

a fluid collection region extending proximally to distally from the base region, the fluid collection region comprising:
  an inner layer that is permeable to urine and air, wherein the inner layer is configured to be placed adjacent to the body of the user such that the urine and air enters the fluid collection region through the inner layer,
  an outer layer that is substantially impermeable to urine and permeable to air, and
  a transfer layer disposed between the inner layer and the outer layer;

a first suction tube extending from the base region and extending along a right side of the fluid collection region between the inner layer and the outer layer and ending in a first fluid inlet at a distal end region of the right side of the fluid collection region;

a second suction tube extending from the base region of the device and extending along a left side of the fluid collection region between the inner layer and the outer layer and ending in a second fluid inlet at the distal end region of the left side of the fluid collection region; and at least one branch extending distally from the base region along a proximal to a distal length of the device and curved to conform to the body of the user, wherein the device is configured such that when suction is applied within the fluid collection region from the first fluid inlet at the distal end region of the right side and/or the second fluid inlet at the distal end region of the left side, air entering the device through the inner layer and/or the outer layer is entrained along the proximal to distal length of the device to enhance evaporation and removal of urine within the fluid collection region.

22. A device for removing urine discharged from a body of a user, the device comprising:

a frame comprising a base region and at least one branch extending from the base region along a proximal to distal length of the device, wherein the at least one branch is curved to conform to the body of the user;

a fluid collection region extending distally from the base region and supported by the at least one branch, the fluid collection region comprising:

an inner layer that is permeable to urine, an outer layer that is substantially impermeable to urine, and a transfer layer disposed between the inner layer and the outer layer;

a first suction tube extending from a suction source tube on the base region and extending along a right side of the fluid collection region between the inner layer and the outer layer and ending in a first fluid inlet at a distal end region of the right side of the fluid collection region; and a second suction tube extending from the suction source tube and extending along a left side of the fluid collection region between the inner layer and the outer layer and ending in a second fluid inlet at the distal end region of the left side of the fluid collection region, wherein the device is configured such that when suction is applied within the fluid collection region from the first fluid inlet at the distal end region of the right side and/or the second fluid inlet at the distal end region of the left side, air entering the device through the inner layer and/or the outer layer is entrained along the proximal to distal length of the device to enhance evaporation and removal of urine within the fluid collection region.

\* \* \* \* \*